US008114874B2

(12) United States Patent
Zou et al.

(10) Patent No.: US 8,114,874 B2
(45) Date of Patent: Feb. 14, 2012

(54) SUBSTITUTED ACETYLENIC IMIDAZO[1,2-B]PYRIDAZINE COMPOUNDS AS KINASE INHIBITORS

(75) Inventors: Dong Zou, Concord, MA (US); Wei-Sheng Huang, Acton, MA (US); R. Mathew Thomas, Waltham, MA (US); Jan Antionette C. Romero, Cambridge, MA (US); Jiwei Qi, West Roxbury, MA (US); Yihan Wang, Newton, MA (US); Xiaotian Zhu, Newton, MA (US); William C. Shakespeare, Southborough, MA (US); Rajeswari Sundaramoorthi, Chennai (IN); Chester A. Metcalf, III, Needham, MA (US); David C. Dalgarno, Brookline, MA (US); Tomi K. Sawyer, Southborough, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/644,849

(22) Filed: Dec. 22, 2006

(65) Prior Publication Data

US 2007/0191376 A1    Aug. 16, 2007

(51) Int. Cl.
*A61K 31/495*    (2006.01)
(52) U.S. Cl. ......... 514/248; 544/236; 544/402; 548/518
(58) Field of Classification Search .................. 514/248; 544/236, 402; 548/518
See application file for complete search history.

(56) References Cited

U.S. PATENT DOCUMENTS

| 6,635,641 | B2 | 10/2003 | Bender et al. |
| 2003/0207885 | A1 | 11/2003 | Hutchinson et al. |
| 2004/0092747 | A1 | 5/2004 | Bender et al. |
| 2006/0217380 | A1 | 9/2006 | Chaffee et al. |
| 2009/0149471 | A1 | 6/2009 | Shakespeare et al. |
| 2009/0176781 | A1 | 7/2009 | Wang et al. |

FOREIGN PATENT DOCUMENTS

| WO | WO 01/81311 A1 | 11/2001 |
| WO | WO 2004/058776 A1 | 7/2004 |
| WO | WO 2005/060969 A1 | 7/2005 |
| WO | WO 2005/060970 A1 | 7/2005 |
| WO | WO 2006/082404 A1 | 8/2006 |
| WO | WO 2006/103449 A2 | 10/2006 |
| WO | WO 2007/013673 A1 | 2/2007 |
| WO | WO 2007/021937 A2 | 2/2007 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, p. 18.*
Definition of isomer. The Merriam-Webster Online Dictionary. http://www.merriam-webster.com/dictionary/isomer. Accessed Dec. 4, 2008.*
Cee, Victor J. et al., Alkynylpyrimidiine Amide Derivatives as Potent, Selective, and Orally Active Inhibitors of Tie-2 Kinase, J. Med. Chem. (2007), 50:4, 627-640.
Acevedo et al, "Inducible FGFR-1 Activiation Leads to Irreversible Prostate Adenocarcinoma and an Epithelial-to-Mesenchymal Transition", Cancer Cell, 2007, pp. 559-571, vol. 12.
Finn, "Targeting Src in Breast Cancer", Annals of Oncology, 2008, pp. 1379-1386, vol. 19(8).
Hiscox et al, "Src as a therapeutic target in anti-hormone/anti growth factor-resistant breast cancer", Endocrine-Related Cancer, 2006, pp. S54-S59, vol. 13.
Kendall et al., "Vascular Endothelial Growth Factor Receptor . . . Loop Tyrosine Residues", Journall of Biological Chemistry, 1999, pp. 6453-6460, vol. 274, No. 10.
Koziczak et al., "Blocking of FGFR signaling inhibits breast cancer cell proliferation through downregulatoin of D-type cyclins", Oncogene, 2004, pp. 3501-3508, vol. 23.
O'Hare et al., "AP24534, a Pan-BRC-ABL Inhibitor for Chronic Myeloid Leukemia, . . . Mutation-Based Resistance", Cancer Cell, 2009, pp. 401-412, vol. 16.
Okamoto et al., "Identification of c-Src . . . Resistance to C-Src Inhibition", Molecular Cancer Therapeutics, 2010, pp. 1188-1197, vol. 9(5).
Zhou et al., "Tumor Angiogenesis Collerlated with bFGF and FGFR-1 in Lung Cancer", Chinese-German Journal of Clinical Oncology, 2005, pp. 93-98, vol. 4(2).
International Search Report for PCT/US06/48758 filed Dec. 22, 2006.
EP Search Report for EP Appl. No. 06845939.5 (Feb. 10, 2010).
Cortes et al., "A Phase 1 Trial of Oral Ponatinib . . . Clinical Response Findings", American Society of Hematology (ASH), 2010, Abstract No. 210.

(Continued)

*Primary Examiner* — James O Wilson
*Assistant Examiner* — Douglas M Willis
(74) *Attorney, Agent, or Firm* — David L. Berstein; Christopher J. Verni

(57) ABSTRACT

This invention relates to compounds of the general formula:

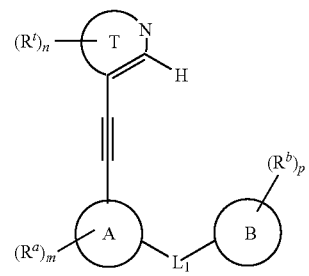

in which the variable groups are as defined herein, and to their preparation and use. In particular, the compounds include embodiments in which Ring T is an imidazo[1,2-b]pyridazine ring system, Rings A and B are each aryl and $L^1$ is —C(O)NR$^1$— or —NR$^1$C(O)—. Uses for the compounds and for compositions containing them include treatment of cancer and other diseases mediated by protein kinases.

55 Claims, No Drawings

OTHER PUBLICATIONS

Gozgit et al., "The Orally Active Kinase Inhibitor AP24534 . . . In Multiple Cancer Models", American Assoc. for Cancer Research (AACR), 2009, Poster Abstract No. 1739.

Gozgit et al., "Ponatinib (AP24534), . . . Distinct Mechanisms of Activation" American Assoc. for Cancer Research (AACR), 2011, Poster Abstract No. 3560.

Gozgit et al., "Potent Activity of Ponatinib (AP24534) . . . and Other Hematologic Malignancies", Molecular Cancer Therapeutics, 2011, pp. 1028-1035, vol. 10 (6).

Huang et al., "Discovery of 3- . . . Including the T315I Gatekeeper Mutant", Journal of Medicinal Chemistry, 2010, pp. 4701-4719, vol. 53.

O'Hare et al., "AP24534, a Pan-BRC-ABL Inhibitor for Chronic Myeloid Leukemia, . . . Mutation-Based Resistance", Cancer Cell, 2009, Supplemental Data, vol. 16.

Rivera et al., "Pharmacodynamics (PD) . . . Chronic Myeloid Leukemia (CML) and Hematologic Malignancies" European School of Haematology (ESH), 2010, Poster Abstract No. 42.

Talpaz et al., "Phase 1 Trial of AP24534 . . . (CML) and Hematologic Malignancies", American Society of Clinical Oncology (ASCO), 2010, Poster Abstract No. 6511.

Talpaz et al., "Ponatinib in Patients . . . Phase 1 Study in Hematologic Malignancies", American Society of Clinical Oncology (ASCO), 2011, Poster Abstract No. 6518.

Zhou et al., "Structural Mechanism . . . Overcoming Kinase Inhibitor Resistance", Chem Biol Drug Des, 2011, pp. 1-11, vol. 77.

Zhu et al., "Structural Analysis . . . T315I Gatekeeper Mutation", American Assoc. for Cancer Research (AACR), 2010, Poster Abstract No. 2671.

* cited by examiner

SUBSTITUTED ACETYLENIC IMIDAZO[1,2-B]PYRIDAZINE COMPOUNDS AS KINASE INHIBITORS

BACKGROUND OF THE INVENTION

The protein kinases are a large family of proteins which play a central role in the regulation of a wide variety of cellular processes. A partial, non limiting, list of such kinases includes abl, Akt, bcr-abl, Blk, Brk, c-kit, c-met, c-src, CDK1, CDK2, CDK3, CDK4, CDK5, CDK6, CDK7, CDK8, CDK9, CDK10, cRaf1, CSK, EGFR, ErbB2, ErbB3, ErbB4, Erk, Pak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK and Zap70. Abnormal protein kinase activity has been related to several disorders, ranging from non-life threatening diseases such as psoriasis to extremely serious diseases such as cancers.

In view of the large number of protein kinases and associated diseases, there is an ever-existing need for new inhibitors selective for various protein kinases which might be useful in the treatment of related diseases.

This invention concerns a new family of acetylenic heteroaryl compounds and their use in treating cancers, bone disorders, metabolic disorders, inflammatory disorders and other diseases.

DESCRIPTION OF THE INVENTION

1. General Description of Compounds of the Invention

The compounds of this invention have a broad range of useful biological and pharmacological activities, permitting their use in pharmaceutical compositions and methods for treating a variety of diseases, including e.g., metabolic disorders, bone diseases (e.g., osteoporosis, Paget's Disease, etc.), inflammation (including rheumatoid arthritis, among other inflammatory disorders) and cancer (including solid tumors and leukemias, especially those mediated by one or more kinases such as Src or kdr, or by dysregulation of a kinase such as Abl and mutant variants thereof), including, among others, advanced cases and cases which are resistant or refractory to one or more other treatments.

Included are compounds of Formula I:

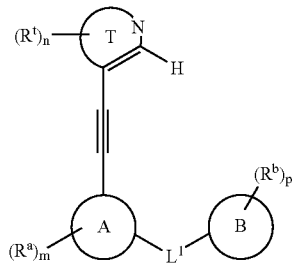

Formula I or a tautomer or an individual isomer or a mixture of isomers thereof in which:

Ring T is a 5-membered heteroaryl ring containing 1-2 nitrogens with the remaining ring atoms being carbon, substituted on at least two ring atoms (each of which may be C or N) with $R^t$ groups, at least two of which being located on adjacent ring atoms, and, together with the atoms to which they are attached, forming a saturated, partially saturated or unsaturated 5- or 6-membered ring (Ring E), containing 0-3 heteroatoms selected from O, N, and S and being optionally substituted with 1-4 $R^e$ groups;

Ring A represents a 5- or 6-membered aryl or heteroaryl ring and is optionally substituted with 1-4 $R^a$ groups;

Ring B represents a 5- or 6-membered aryl or heteroaryl ring and is optionally substituted with 1-5 $R^b$ goups;

$L^1$ is selected from $NR^1C(O)$, $C(O)NR^1$, $NR^1C(O)O$, $NR^1C(O)NR^1$, and $OC(O)NR^1$;

each occurrence of $R^a$, $R^b$ and $R^t$ is independently selected from the group consisting of halo, —CN, —NO$_2$, —R$^4$, —OR$^2$, —NR$^2$R$^3$, —C(O)YR$^2$, —OC(O)YR$^2$, —NR$^2$C(O)YR$^2$, —SC(O)YR$^2$, 13 NR$^2$C(=S)YR$^2$, —OC(=S)YR$^2$, —C(=S)YR$^2$, —YC(=NR$^3$)YR$^2$, —YP(=O)(YR$^4$)(YR$^4$), —Si(R$^2$)$_3$, —NR$_2$C(=S)YR$^2$, —OC(=S)YR$^2$, —C(=S)YR$^2$, —YC(=NR$^3$)YR$^2$, —YP(=O)(YR$^4$)(YR$^4$), —Si(R$^2$)$_3$, NR$^2$SO$_2$R$^2$, —S(O),R$^2$, —SO$_2$NR$^2$R$^3$ and —NR$^2$SO$_2$NR$^2$R$^3$, wherein each Y is independently a bond, —O—, —S— or —NR$^3$—;

$R^e$, at each occurrence, is independently selected from the group consisting of halo, =O, —CN, —NO$_2$, —R$^4$, —OR$^2$, —NR$^2$R$^3$, —C(O)YR$^2$, —OC(O)YR$^2$, —NR$^2$C(O)YR$^2$, —SC(O)YR$^2$, —NR$^2$C(=S)YR$^2$, —OC(=S)YR$^2$, —C(=S)YR$^2$, —YC(=NR$^3$)YR$^2$, —YP(=O)(YR$^4$)(YR$^4$), —Si(R$^2$)$_3$, —NR$^2$SO$_2$R$^2$, —S(O),R$^2$, —SO$_2$NR$^2$R$^3$ and —NR$^2$SO$_2$NR$^2$R$^3$, wherein each Y is independently a bond, —O—, —S— or —NR$^3$—;

$R^1$, $R^2$ and $R^3$ are independently selected from H, alkyl, alkenyl, alkynyl, cycloalkyl, cycloalkenyl, cycloalkynyl, aryl, heterocyclic and heteroaryl;

alternatively, $R^2$ and $R^3$, taken together with the atom to which they are attached, form a 5- or 6- membered saturated, partially saturated or unsaturated ring, which can be optionally substituted and which contains 0-2 heteroatoms selected from N, O and S(O)$_r$;

each occurrence of $R^4$ is independently selected from alkyl, alkenyl, alkynyl, cycloalkyl, cycloalkenyl, cycloalkynyl, aryl, heterocyclic and heteroaryl;

each of the alkyl, alkenyl, alkynyl, cycloalkyl, cycloalkenyl, cycloalkynyl, aryl, heterocyclic and heteroaryl moieties in this Section 1 is optionally substituted;

m is 0, 1, 2, 3 or 4;

n is 2 or 3;

p is 0, 1, 2, 3, 4 or 5; and, r is 0, 1 or 2;

or a pharmaceutically acceptable salt, solvate or hydrate thereof.

The foregoing definitions are further elaborated upon and exemplified below and apply to all subsequent occurrences except to the extent otherwise specified.

2. Featured Classes of Compounds and their Use, Generally

Compounds of this invention include those in which Ring T has the following structure:

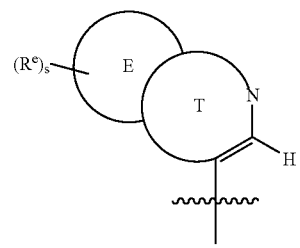

where Ring E is a 5- or 6-membered unsaturated ring (formed by two $R^f$ groups together with the Ring T atoms to which they are attached, as described above) and s is 0, 1, 2, 3 or 4. These are illustrated by the compounds of formula I in which the fused Ring T ring system is one of the following (in which one of the optional $R^e$ substituents is depicted):

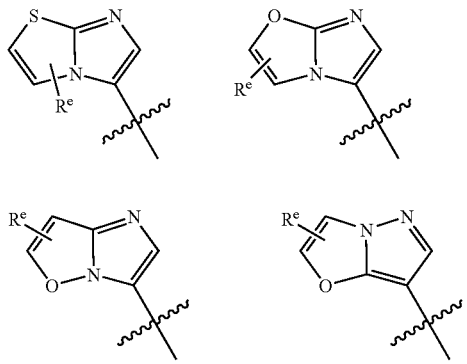

Other classes of particular interest are compounds of Formula I, as described in Part 1, in which Ring E is a 6-membered ring, otherwise as described above. Illustrative examples of such compounds include compounds of Formula I in which Ring T (with its attached Ring E) is a fused bicyclic heteroaryl of the following types:

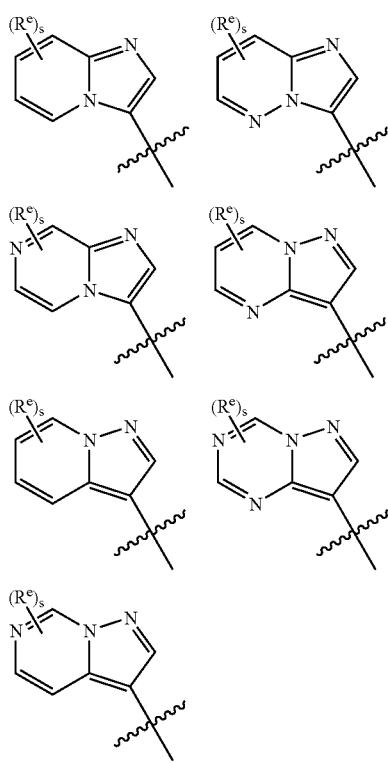

For the previously described class and subclasses of compounds, as in all compounds of this invention, Ring A and Ring B are as previously defined in Part 1.

Illustrative examples of substituted Ring A groups are:

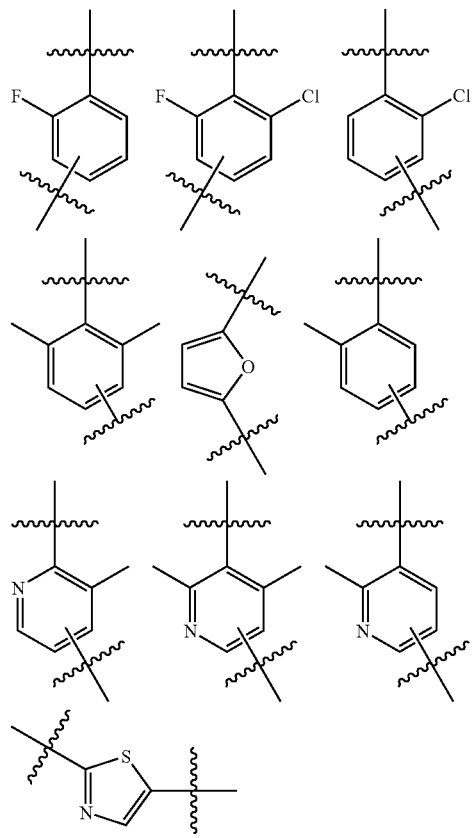

Ring B represents a 5 or 6-membered aryl or heteroaryl ring as defined above in Part 1.

Illustrative examples of substituted Ring B groups include:

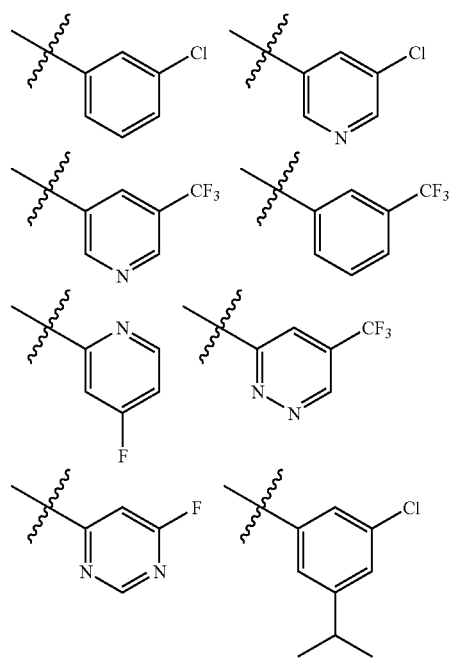

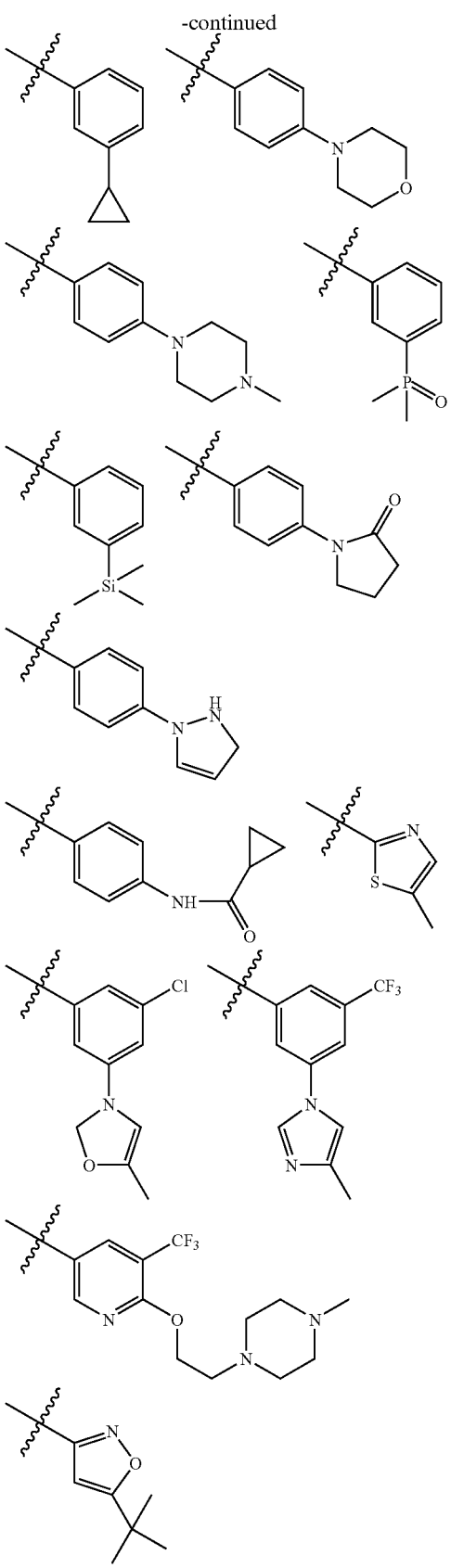

ents is a 5- or 6-membered ring (Ring C), which may be heteroaryl or heterocyclic, comprising carbon atoms and 1-3 heteroatoms independently selected from O, N and S(O)$_r$, and Ring C being optionally substituted on carbon or heteroatom(s) with 1 to 5 substituents R$^c$.

This class is represented by Formula II:

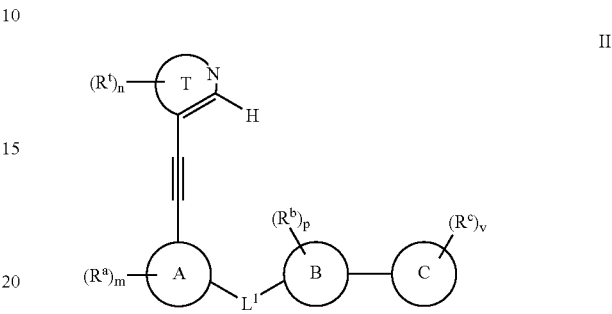

in which the previously defined variables, e.g., n, m, p, A, B, T, L$^1$, R$^1$, R$^t$, R$^a$ and R$^b$, are as defined above in part 1, and R$^c$, at each occurrence, is independently selected from halo, =O, —CN, —NO$_2$, —R$^4$, —OR$^2$, —NR$^2$R$^3$, —C(O)YR$^2$, —OC(O)YR$^2$, —NR$^2$C(O)YR$^2$, —Si(R$^2$)$_3$, —SC(O)YR$^2$, —NR$^2$C(=S)YR$^2$, —OC(=S)YR$^2$, —C(=S)YR$^2$, —YC(=NR$^3$)YR$^2$, —YP(=O)(YR$^4$)(YR$^4$), —NR$^2$SO$_2$R$^2$, —S(O)$_r$R$^2$, —SO$_2$NR$^2$R$^3$ and —NR$^2$SO$_2$NR$^2$R$^3$, wherein each Y is independently a bond, —O—, —S— or —NR$^3$— and r, R$^2$, R$^3$ and R$^4$, are as defined previously in Part 1; and, v is 0, 1, 2, 3, 4 or 5.

Illustrative examples of Ring C systems include but are not limited to the following types:

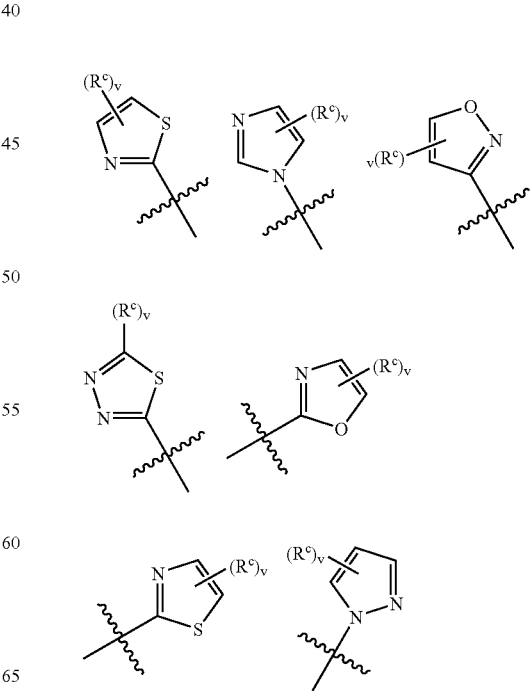

Of special interest is the class of compounds of Formula I as described above in Part 1, in which one of the R$^b$ substitu-

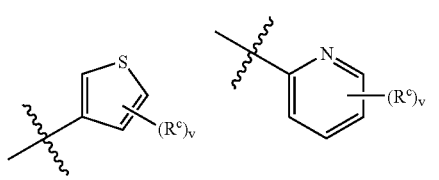

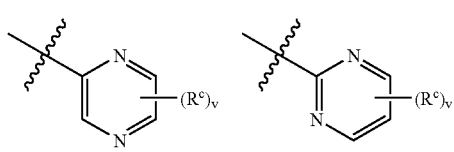

in which $R^c$ and v are as defined above.

Of special interest is the class of compounds of formula II in which Ring T has the following structure:

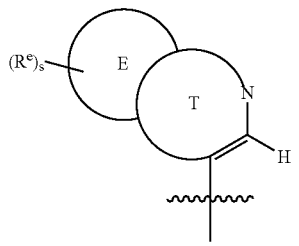

in which the indicated variables, e.g., $R^e$, s and Ring E, are as defined previously.

Illustrative subsets of such compounds include those having the following structures:

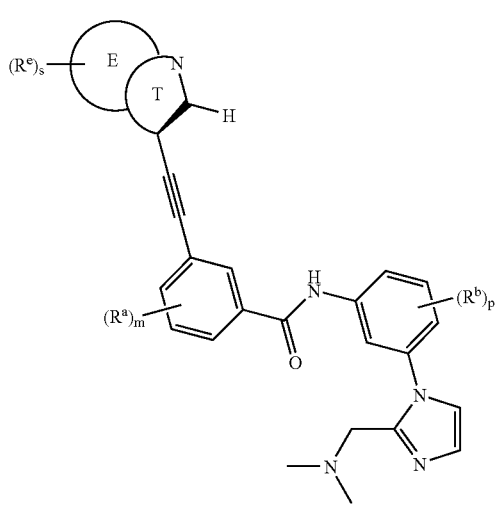

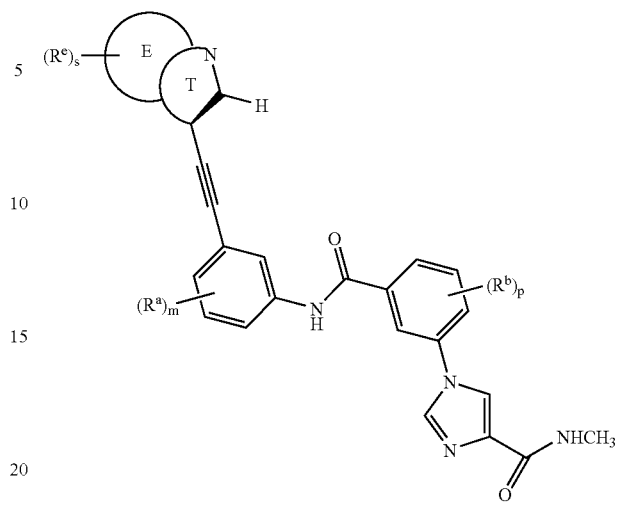

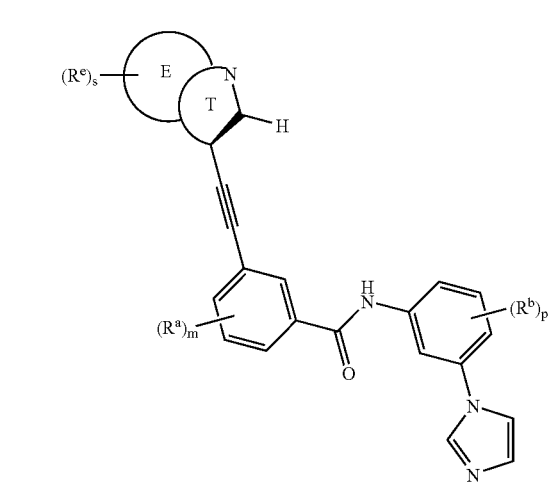

as embodied by the following non-limiting illustrative examples:

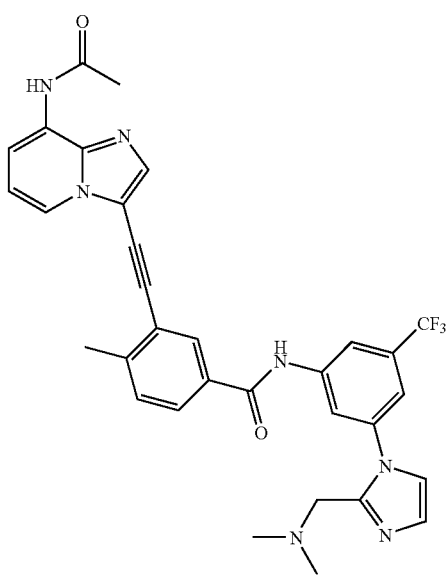

-continued

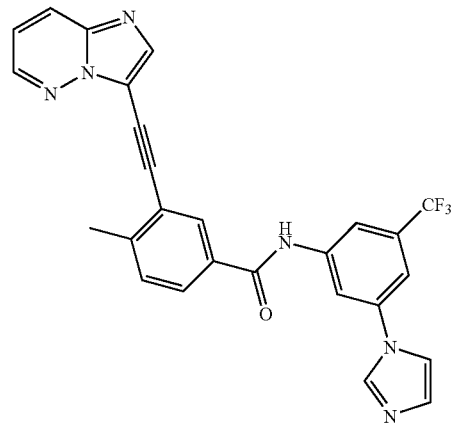

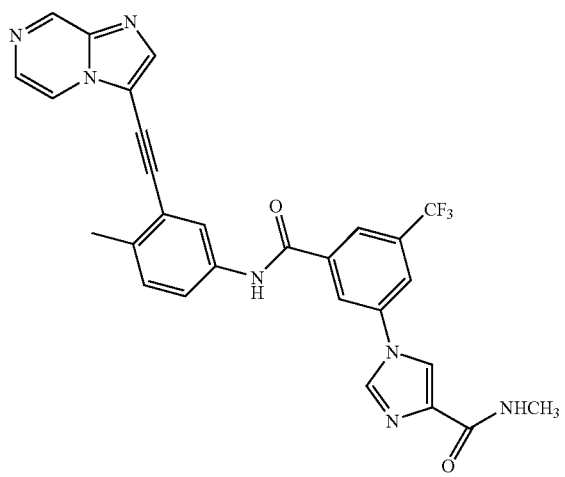

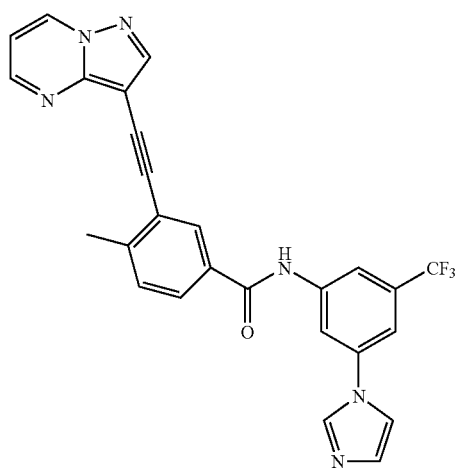

in which several illustrative -[Ring A]-[$L^1$]-[Ring ]-[Ring C]-portions are depicted.

Compounds of interest include among others, compounds of Formula II in which Ring C is an imidazole ring, optionally substituted with one or more $R^c$ groups. Of particular interest, are compounds of this subclass in which Ring C bears a single lower alkyl (e.g., methyl) $R^c$ group.

A further feature of the invention relates to compounds of Formula I as described in Part 1, in which one $R^b$ substituent is -[$L^2$]-[Ring D]. This class is represented by Formula III:

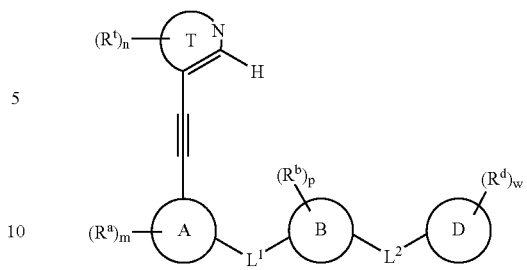

in which the previously defined variables, e.g., n, m, p, Ring T, Ring A, Ring B, $L^1$, $R^1$, $R^1$, $R^t$, $R^a$ and $R^b$, are defined above in part 1, and $L^2$ is selected from $(CH_2)_z$, $O(CH_2)_x$, $NR^3(CH_2)_x$, $S(CH_2)_x$, and $(CH_2)_xNR^3C(O)(CH_2)_x$, and the linker moiety $L^2$ can be included in either direction;

Ring D represents a 5- or 6-membered heterocyclic or heteroaryl ring comprising carbon atoms and 1-3 heteroatoms independently selected from O, N and $S(O)_r$, and Ring D is optionally substituted on carbon or heteroatom(s) with 1-5 $R^d$ groups;

$R^d$, at each occurrence, is independently selected from halo, =O, —CN, —$NO_2$, —$R^4$, —$OR^2$, —$NR^2R^3$, —$Si(R^2)_3$, —$C(O)YR^2$, —$OC(O)YR^2$, —$NR^2C(O)YR^2$, —$SC(O)YR^2$, —$NR^2C(=S)YR^2$, —$OC(=S)YR^2$, —$C(=S)YR^2$, —$YC(=NR^3)YR^2$, —$YP(=O)(YR^4)(YR^4)$, —$NR^2SO_2R^2$, —$S(O)_rR^2$, —$SO_2NR^2R^3$ and —$NR^2SO_2NR^2R^3$, wherein each Y is independently a bond, —O—, —S— or —$NR^3$— and r, $R^2$, $R^3$ and $R^4$ are as previously defined in Part 1;

w is 0, 1, 2, 3, 4 or 5;
x is 0, 1, 2 or 3; and,
z is 1, 2, 3 or 4,

Non-limiting, illustrative examples of -[Ring B]-[$L^2$]-[Ring D] moieties in compounds of Formula III include among others:

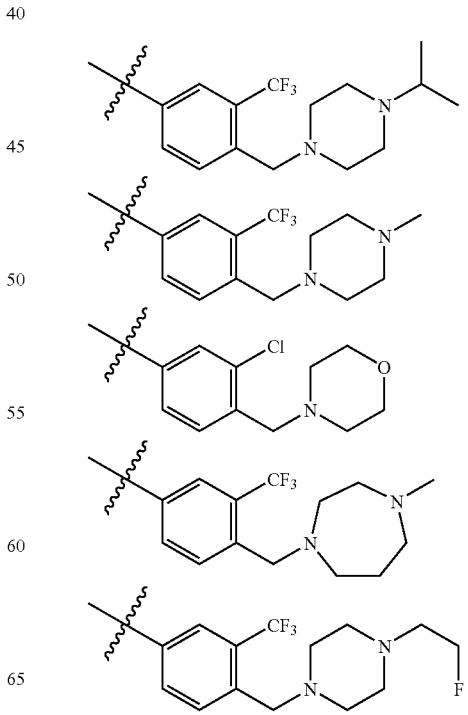

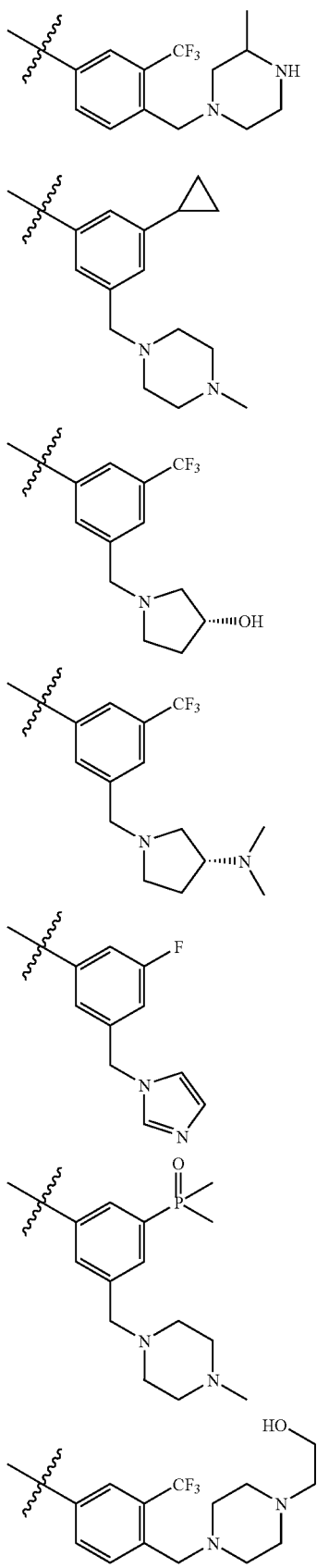
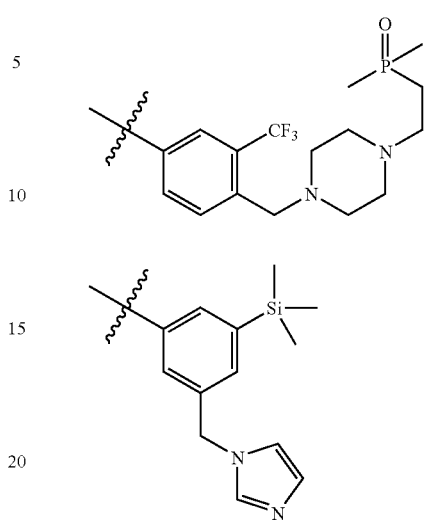
Of special interest is the class of compounds of formula III in which Ring T has the following structure:
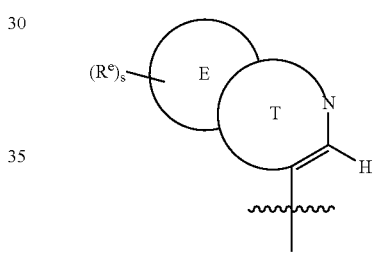
in which the previously defined variables, e.g., $R^e$, s, and Ring E, are as defined previously.
Non-limiting examples of such compounds include those having the following structures:
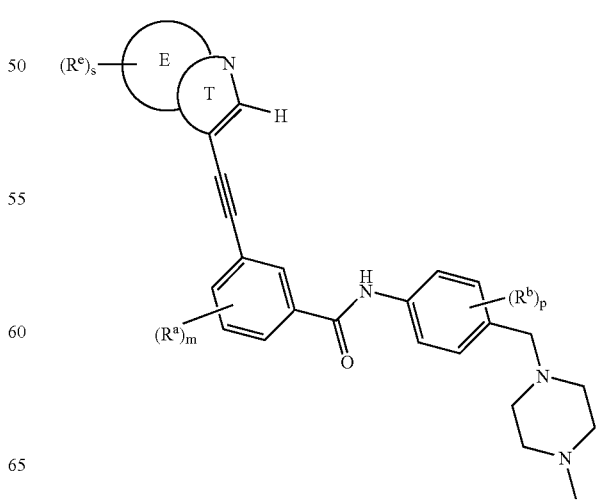

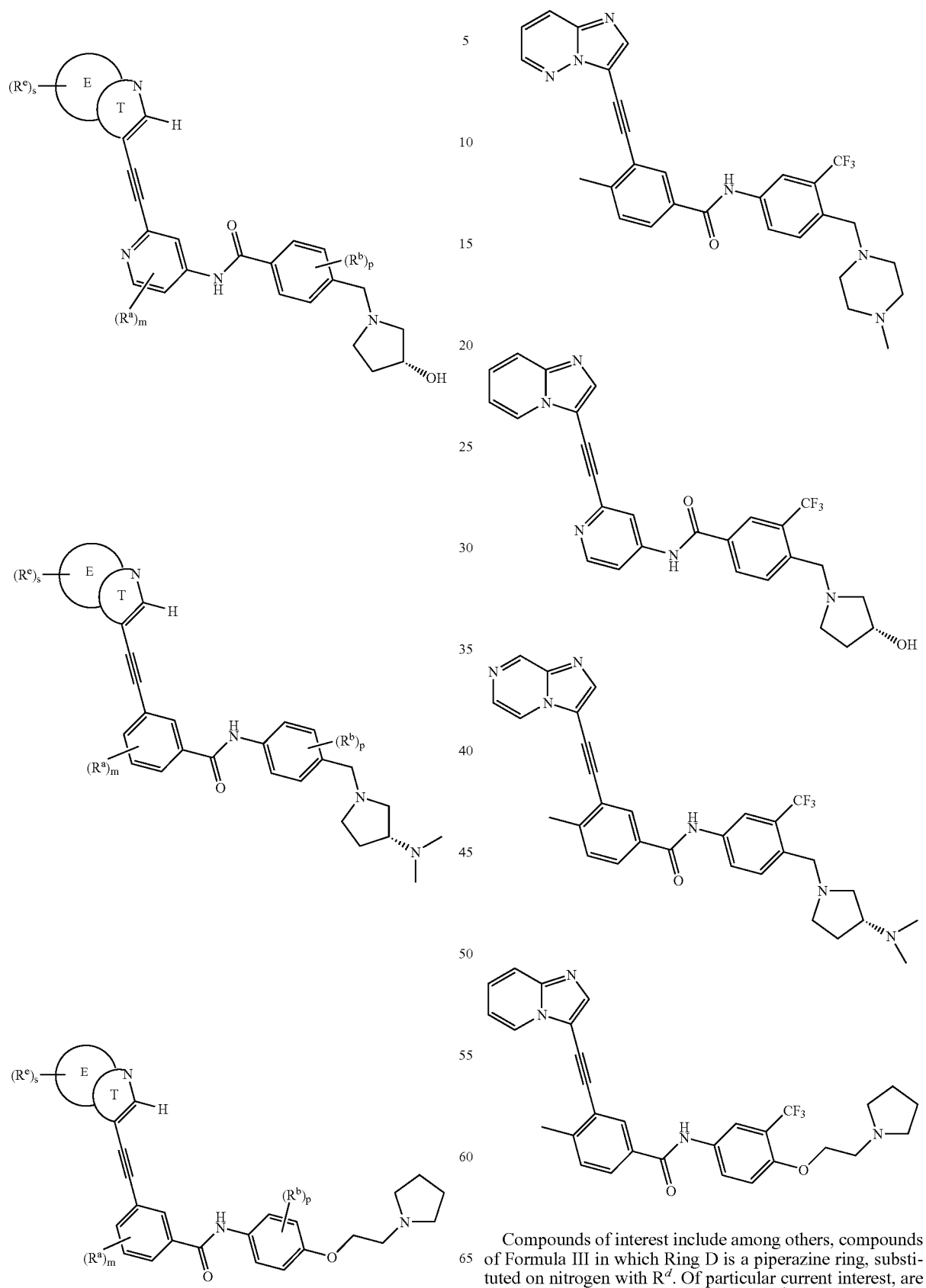
Compounds of interest include among others, compounds of Formula III in which Ring D is a piperazine ring, substituted on nitrogen with $R^d$. Of particular current interest, are compounds of this subclass in which $R^d$ is a substituted or unsubstituted lower (i.e., 1-6 carbon) alkyl as illustrated by N-methylpiperazine moieties in some of the foregoing examples.

Of special interest are compounds of formula II and formula III in which Ring T is an optionally substituted imidazo[1,2-a]pyridine, imidazo[1,2-b]pyridazine, imidazo[1,2-a]pyrazine, pyrazolo[1,5-a]pyrimidine, pyrazolo[1,5-a]pyridine, pyrazolo[1,5-c]pyrimidine, and pyrazolo[1,5-a][1,3,5]triazine.

Also of interest are compounds of formula II and formula III in which Rings A and B are aryl.

Another subclass of interest are compounds of Formulas II and III, in which Ring T is any 6/5 fused heteroaryl ring system, optionally substituted with up to three $R^e$ groups. Of particular interest are compounds in which s is 0, Also of interest are those in which s is 1-3 and at least one $R^e$ is halo, lower alkyl, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocycle, —NH(CH$_2$)$_x$-aryl or —(CH$_2$)$_x$C(O)NH$_2$, in which x is 0, 1, 2 or 3 and "alkyl" includes straight (i.e., unbranched and acyclic), branched and cyclic alkyl groups and in which aryl, heteroaryl, heterocyclyl rings are optionally substituted. Illustrative, non limiting, examples of the foregoing include compounds of formulas II and III in which Ring T is one of the following:

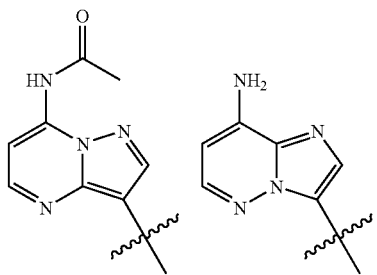

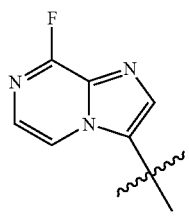

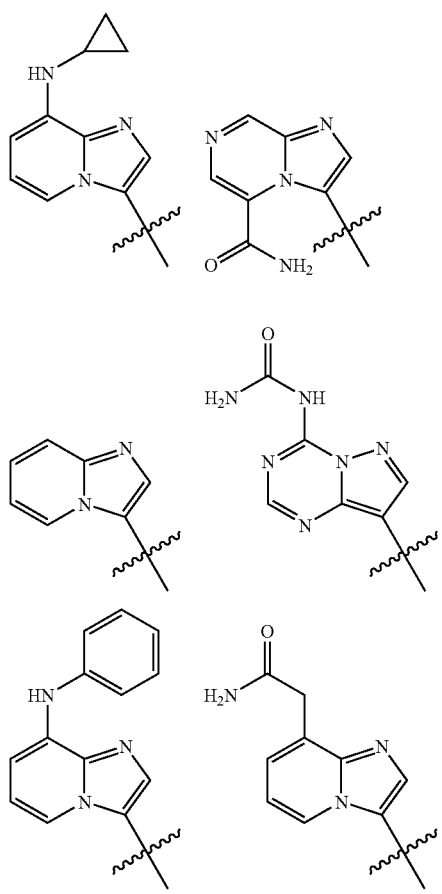

Illustrative, non limiting examples of this subclass include compounds of formulas IIa, IIb, IIc, IIIa, IIIb and IIIc:

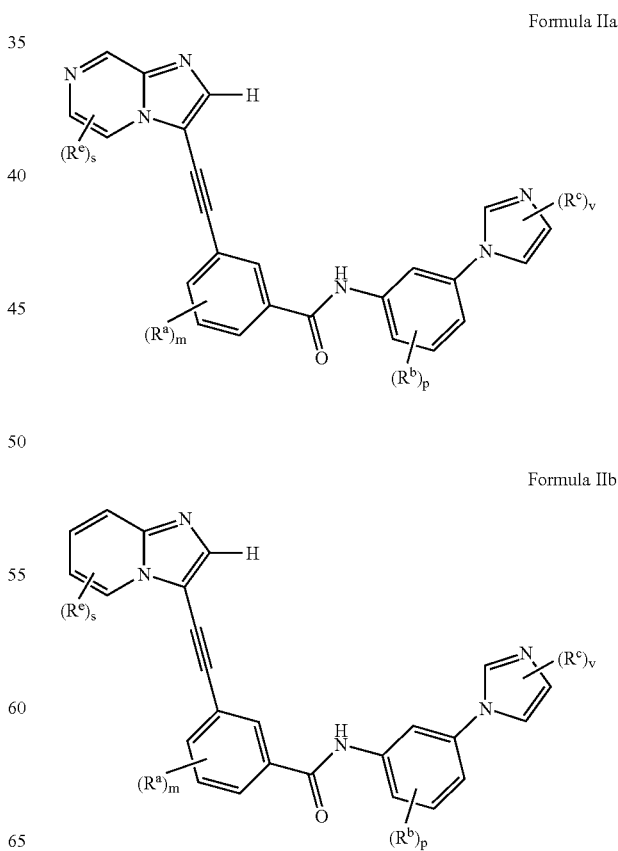

Formula IIa

Formula IIb

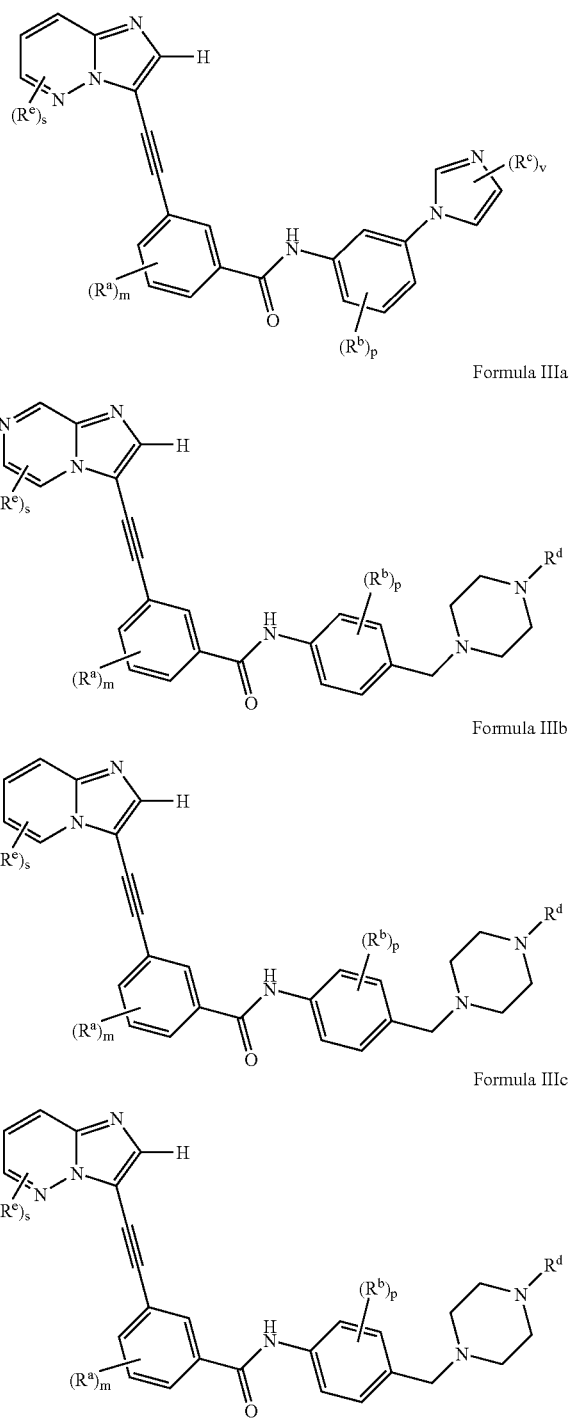

Formula IIc

Formula IIIa

Formula IIIb

Formula IIIc in which the previously defined variables, e.g., $R^a$, $R^b$, $R^c$, $R^d$, $R^e$, m and p, are as previously defined, e.g., in part 1, and s is an integer from 0 to 4.

One subset of interest includes compounds of Formulas IIa, IIb and IIc in which s is 0; m, p and v are 1; and, $R^a$ is $CH_3$, $R^b$ is $CF_3$ and $R^c$ is methyl.

Another includes compounds of Formulas IIIa, IIIb, IIIc in which s is 0; m and p are 1; and, $R^a$ is $CH_3$, $R^b$ is $CF_3$ and $R^d$ is $CH_3$ or $CH_2CH_2OH$.

Compounds of this invention of particular interest include those with one or more of the following characteristics:

a molecular weight of less than 1000, preferably less than 750 and more preferably less than 600 mass units (not including the weight of any solvating or co-crystallizing species, of any counter-ion in the case of a salt); or inhibitory activity against a wild type or mutant (especially a clinically relevant mutant) kinase, especially a Src family kinase such as Src, Yes, Lyn or Lck; a VEGF-R such as VEGF-R1 (Flt-1), VEGF-R2 (kdr), or VEGF-R3; a PDGF-R; an Abl kinase or another kinase of interest with an IC50 value of 1 µM or less (as determined using any scientifically acceptable kinase inhibition assay), preferably with an IC50 of 500 nM or better, and optimally with an IC50 value of 250 nM or better; or inhibitory activity against a given kinase with an IC50 value at least 100-fold lower than their IC50 values for other kinases of interest; or inhibitory activity against both Src and kdr with a 1 µM or better IC50 value against each; or a cytotoxic or growth inhibitory effect on cancer cell lines maintained in vitro, or in animal studies using a scientifically acceptable cancer cell xenograft model, (especially preferred are compounds of the invention which inhibit proliferation of cultured K562 cells with a potency at least as great as Gleevec, preferably with a potency at least twice that of Gleevec, and more preferably with a potency at least 10 times that of Gleevec as determined by comparative studies.).

Also provided is a composition comprising at least one compound of the invention or a salt, hydrate or other solvate thereof, and at least one pharmaceutically acceptable excipient or additive. Such compositions can be administered to a subject in need thereof to inhibit the growth, development and/or metastasis of cancers, including solid tumors (e.g., breast, colon, pancreatic, CNS and head and neck cancers, among others) and various forms of leukemia, including leukemias and other cancers which are resistant to other treatment, including those which are resistant to treatment with Gleevec or another kinase inhibitor, and generally for the treatment and prophylaxis of diseases or undesirable conditions mediated by one or more kinases which are inhibited by a compound of this invention.

The cancer treatment method of this invention involves administering (as a monotherapy or in combination with one or more other anti-cancer agents, one or more agents for ameliorating side effects, radiation, etc) a therapeutically effective amount of a compound of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by one or more kinases inhibited by one of the disclosed compounds or a pharmaceutically acceptable derivative thereof. "Administration" of a compound of this invention encompasses the delivery to a recipient of a compound of the sort described herein, or a prodrug or other pharmaceutically acceptable derivative thereof, using any suitable formulation or route of administration, as discussed herein. Typically the compound is administered one or more times per month, often one or more times per week, e.g. daily, every other day, 5 days/week, etc. Oral and intravenous administrations are of particular current interest.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue (MW>300) thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention.

Particularly favored derivatives and prodrugs of a parent compound are those derivatives and prodrugs that increase the bioavailability of the compound when administered to a mammal (e.g., by permitting enhanced absorption into the blood following oral administration) or which enhance delivery to a biological compartment of interest (e.g., the brain or lymphatic system) relative to the parent compound. Preferred prodrugs include derivatives of a compound of this invention with enhanced aqueous solubility or active transport through the gut membrane, relative to the parent compound.

One important aspect of this invention is a method for treating cancer in a subject in need thereof, which comprises administering to the subject a treatment effective amount of a composition containing a compound of this invention. Various cancers which may be thus treated are noted elsewhere herein and include, among others, cancers which are or have become resistant to another anticancer agent such as Gleevec, Iressa, Tarceva or one of the other agents noted herein. Treatment may be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF) to name a few), hyperthermia, cryotherapy, agents to attenuate any adverse effects (e.g., antiemetics), and other cancer chemotherapeutic drugs. The other agent(s) may be administered using a formulation, route of administration and dosing schedule the same or different from that used with the compound of this invention.

Such other drugs include but not limited to one or more of the following: an anti-cancer alkylating or intercalating agent (e.g., mechlorethamine, chlorambucil, Cyclophosphamide, Melphalan, and Ifosfamide); antimetabolite (e.g., Methotrexate); purine antagonist or pyrimidine antagonist (e.g., 6-Mercaptopurine, 5-Fluorouracil, Cytarabile, and Gemcitabine); spindle poison (e.g., Vinblastine, Vincristine, Vinorelbine and Paclitaxel); podophyllotoxin (e.g., Etoposide, Irinotecan, Topotecan); antibiotic (e.g., Doxorubicin, Bleomycin and Mitomycin); nitrosourea (e.g., Carmustine, Lomustine); inorganic ion (e.g., Cisplatin, Carboplatin, Oxaliplatin or oxiplatin); enzyme (e.g., Asparaginase); hormone (e.g., Tamoxifen, Leuprolide, Flutamide and Megestrol); mTOR inhibitor (e.g., Sirolimus (rapamycin), Temsirolimus (CC1779), Everolimus (RAD001), AP23573 or other compounds disclosed in U.S. Pat. No. 7,091,213); proteasome inhibitor (such as Velcade, another proteasome inhibitor (see e.g., WO 02/096933) or another NF-kB inhibitor, including, e.g., an IkK inhibitor); other kinase inhibitors (e.g., an inhibitor of Src, BRC/Abl, kdr, flt3, aurora-2, glycogen synthase kinase 3 ("GSK-3"), EGF-R kinase (e.g., Iressa, Tarceva, etc.), VEGF-R kinase, PDGF-R kinase, etc); an antibody, soluble receptor or other receptor antagonist against a receptor or hormone implicated in a cancer (including receptors such as EGFR, ErbB2, VEGFR, PDGFR, and IGF-R; and agents such as Herceptin, Avastin, Erbitux, etc.); etc. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference. Examples of other therapeutic agents are noted elsewhere herein and include among others, Zyloprim, alemtuzmab, altretamine, amifostine, nastrozole, antibodies against prostate-specific membrane antigen (such as MLN-591, MLN591RL and MLN2704), arsenic trioxide, bexarotene, bleomycin, busulfan, capecitabine, Gliadel Wafer, celecoxib, chlorambucil, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, exemestane, fludarabine, 5-FU, fulvestrant, gemcitabine, gemtuzumab-ozogamicin, goserelin acetate, hydroxyurea, idarubicin, idarubicin, Idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, 2C4 (or other antibody which interferes with HER2-mediated signaling), tretinoin, ATRA, valrubicin, vinorelbine, or pamidronate, zoledronate or another bisphosphonate.

This invention further comprises the preparation of a compound of any of Formulas I, II, III, IIa, IIb, IIc, IIIa, IIIb, IIIc or of any other of the compounds of this invention.

The invention also comprises the use of a compound of the invention, or a pharmaceutically acceptable derivative thereof, in the manufacture of a medicament for the treatment either acutely or chronically of cancer (including leukemias and solid tumors, primary or metastatic, including cancers such as noted elsewhere herein and including cancers which are resistant or refractory to one or more other therapies). The compounds of this invention are useful in the manufacture of an anti-cancer medicament. The compounds of the present invention are also useful in the manufacture of a medicament to attenuate or prevent disorders through inhibition of one or more kinases such as Src, kdr, abl. etc.

Other disorders which may be treated with a compound of this invention include metabolic disorders, inflammatory disorders and osteoporosis and other bone disorders. In such cases the compound of this invention may be used as a monotherapy or may be administered in conjunction with administration of another drug for the disorder, e.g., a bisphosphonate in the case of osteoporosis or other bone-related illnesses.

This invention further encompasses a composition comprising a compound of the invention, including a compound of any of the described classes or subclasses, including those of any of the formulas noted above, among others, preferably in a therapeutically-effective amount, in association with a least one pharmaceutically acceptable carrier, adjuvant or diluent.

Compounds of this invention are also useful as standards and reagents for characterizing various kinases, especially but not limited to kdr and Src family kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

3. Definitions

In reading this document, the following information and definitions apply unless otherwise indicated. In addition, unless otherwise indicated, all occurrences of a functional group are independently chosen, as the reader is in some cases reminded by the use of a slash mark or prime to indicate simply that the two occurrences may be the same or different (e.g., R, R', R", or Y, Y', Y" etc.).

The term "Alkyl" is intended to include linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_{1-6}$ alkyl, is intended to include $C_1$, $C_2$, $C_3$, $C_4$, $C_5$, and $C_6$ alkyl groups. Lower alkyl refers to alkyl groups containing 1 to 6 carbon atoms. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The term "Alkoxy" represent a subset of alkyl in which an alkyl group as defined above with the indicated number of carbons attached through an oxygen bridge. For example, "alkoxy" refers to groups —O-alkyl, wherein the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

"Haloalkyl" is intended to include both branched and linear chain saturated hydrocarbon having one or more carbon substituted with a Halogen. Examples of haloalkyl, include, but are not limited to, trifluoromethyl, trichloromethyl, pentafluoroethyl and the like.

The term "alkenyl" is intended to include hydrocarbon chains of linear, branched, or cyclic configuration having one or more unsaturated Carbon-carbon bonds that may occur in any stable point along the chain or cycle. Unless otherwise specified, "alkenyl" refers to groups usually having two to eight, often two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. Furthermore, alkenyl groups may be substituted or unsubstituted.

The term "alkynyl" is intended to include hydrocarbon chains of either linear or branched configuration, having one or more carbon-carbon triple bond that may occur in any stable point along the chain. Unless otherwise specified, "alkynyl" groups refer refers to groups having two to eight, preferably two to six carbons. Examples of "alkynyl" include, but are not limited to prop-2-ynyl, but-2-ynyl, but-3-ynyl, pent-2-ynyl, 3-methylpent-4-ynyl, hex-2-ynyl, hex-5-ynyl, etc. Furthermore, alkynyl groups may be substituted or unsubstituted.

Cycloalkyl is a subset of alkyl and includes any stable cyclic or polycyclic hydrocarbon groups of from 3 to 13 carbon atoms, any of which is saturated. Examples of such cycloalkyl include, but are not limited to cyclopropyl, norbornyl, [2.2.2]bicyclooctane, [4.4.0]bicyclodecane, and the like, which, as in the case of other alkyl moieties, may optionally be substituted. The term "cycloalkyl" may be used interchangeably with the term "carbocycle".

Cycloalkenyl is a subset of alkenyl and includes any stable cyclic or polycyclic hydrocarbon groups of from 3 to 13 carbon atoms, preferably from 5 to 8 carbon atoms, which contains one or more unsaturated carbon-carbon double bonds that may occur in any point along the cycle. Examples of such cycloalkenyl include, but are not limited to cyclopentenyl, cyclohexenyl and the like.

Cycloalkynyl is a subset of alkynyl and includes any stable cyclic or polycyclic hydrocarbon groups of from 5 to 13 carbon atoms, which contains one or more unsaturated carbon-carbon triple bonds that may occur in any point along the cycle. As in the case of other alkenyl and alkynyl moieties, cycloalkenyl and cycloalkynyl may optionally be substituted.

"Heterocycle", "heterocyclyl", or "heterocyclic" as used herein refers to non-aromatic ring systems having five to fourteen ring atoms, preferably five to ten, in which one or more ring carbons, preferably one to four, are each replaced by a heteroatom such as N, O, or S. Non-limiting examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "aryl" used alone or as part of a larger moiety as in "aralkyl", "aralkoxy", or "aryloxy-alkyl", refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 5-14 ring atoms. Heteroaryl groups may be substituted or unsubstituted and may comprise one or more rings. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). Further specific examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Heteroaryl groups further include a group in which a heteroaromatic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl, imidazo[1,2-a]pyrimidyl, imidazo[1,2-a]pyrazinyl, imidazo[1,2-a]pyridinyl, imidazo[1,2-c]pyrimidyl, pyrazolo[1,5-a][1,3,5]triazinyl, pyrazolo[1,5-c]pyrimidyl, imidazo[1,2-b]pyridazinyl, imidazo[1,5-a]pyrimidyl, pyrazolo[1,5-b][1,2,4]triazine, quinolyl, isoquinolyl, quinoxalyl, imidazotriazinyl, pyrrolo[2,3-d]pyrimidyl, triazolopyrimidyl, pyridopyrazinyl. The term "heteroaryl" also refers to rings that are optionally substituted. The term "heteroaryl" may be used interchangeably with the term "heteroaryl ring" or the term "heteroaromatic".

An aryl group (including the aryl portion of an aralkyl, aralkoxy, or aryloxyalkyl moiety and the like) or heteroaryl group (including the heteroaryl portion of a heteroaralkyl or heteroarylalkoxy moiety and the like) may contain one or more substituents. Examples of suitable substituents on the unsaturated carbon atom of an aryl or heteroaryl group include halogen (F, Cl, Br or I), —CN, —$R^4$, —$OR^2$, —S(O)$_r$ $R^2$, (wherein r is an integer of 0, 1 or 2), —$SO_2NR^2R^3$, —$NR^2R^3$, —CO)$YR^2$, —O(CO)$YR^2$, —$NR^2$(CO)$YR^2$, —S(CO)$YR^2$, —$NR^2C(=S)YR^2$, —OC(=S)$YR^2$, —C(=S)$YR^2$, wherein each occurrence of Y is independently —O—, —S—, —$NR^3$—, or a chemical bond; —(CO)$YR^2$ thus encompasses —C(=O)$R^2$, —C(=O)$OR^2$ and —C(=O)$NR^2R^3$. Additional substituents include —YC(=$NR^3$)Y'$R^2$, —$COCOR^2$, —$COMCOR^2$ (where M is a 1-6 carbon alkyl group), —YP(=O)($YR^4$)($YR^4$) (including among others —P(=O)($R^4$)$_2$), —S($R^2$)$_3$, —$NO_2$, —$NR^2SO_2R^2$ and —$NR^2SO_2NR^2R^3$. To illustrate further, substituents in which Y is —$NR^3$ thus include among others, —$NR^3C(=O)R^2$, —$NR^3C(=O)NR^2R^3$, —$NR^3C(=O)OR^2$ and —$NR^3C(=NH)NR^2R^3$. $R^2$ and $R^3$ substituents at each occurrence are independently selected from hydrogen, alkyl, alkenyl, alkynyl, cycloalkyl, cycloalkenyl, cycloalkynyl, aryl, heteroaryl, heterocyclyl, and $R^2$ and $R^3$ (and $R^4$) substituents may themselves be substituted or unsubstituted. Examples of substituents allowed on $R^2$, $R^3$ and $R^4$ include, among others amino, alkylamino, dialkylamino, aminocarbonyl, halogen, alkyl, alkenyl, alkynyl, aryl, heteroaryl, carbocycle, heterocycle, alkylaminocarbonyl, dialkylaminocarbonyl, alkylaminocarbonyloxy, dialkylaminocarbonyloxy, nitro, cyano, carboxy, alkoxycar-bonyl, alkylcarbonyl, hydroxy, alkoxy, haloalkoxy groups. Additional illustrative examples include protected OH (such as acyloxy), phenyl, substituted phenyl, —O-phenyl, —O-(substituted)phenyl, -benzyl, substituted benzyl, —O-phenethyl (i.e., —$OCH_2CH_2C_6H_5$), —O-(substituted)phenethyl. Non-limiting illustrations of a substituted $R^2$, $R^3$ or $R^4$ moiety include haloalkyl and trihaloalkyl, alkoxyalkyl, halophenyl, -M-heteroaryl, -M-heterocycle, -M-aryl, -M-$OR^2$, -M-$SR^2$, -M-$NR^2R^3$, -M-$OC(O)NR^2R^3$, -M-$C(=NR^2)NR^2R^3$, -M-C(=$NR^2$)$OR^3$, -M-P(O)$R^2R^3$, Si($R^2$)$_3$, -M-$NR^2C(O)R^3$, -M-$NR^2C(O)OR^2$, -M-C(O)$R^2$, -M-C(=S)$R^2$, -M-C(=S)$NR^2R^3$, -M-C(O)$NR^2R^3$, -M-C(O)$NR^2$-M-$NR^2R^3$, -M-$NR^2C(NR^3)NR^2R^3$, -M-$NR^2C(S)NR^2R^3$, -M-S(O)$_2R^3$, -M-C(O)$R^3$, -M-OC(O)$R^3$, -MC(O)$SR^2$, -M-S(O)$_2NR^2R^3$, —C(O)-M-C(O)$R^2$, -$MCO_2R^2$, -MC(=O)$NR^2R^3$, -M-C(=NH)$NR^2R^3$ and -M-OC(=NH)$NR^2R^3$ (wherein M is a 1-6 carbon alkyl group).

Some more specific examples include but are not limited to chloromethyl, trichloromethyl, trifluoromethyl, methoxyethyl, alkoxyphenyl, halophenyl, —$CH_2$-aryl, —$CH_2$-heterocycle, —$CH_2C(O)NH_2$, —C(O)$CH_2N(CH_3)_2$, —$CH_2CH_2OH$, —$CH_2OC(O)NH_2$, —$CH_2CH_2NH_2$, —$CH_2CH_2CH_2NEt_2$, —$CH_2OCH_3$, —C(O)$NH_2$, —$CH_2CH_2$-heterocycle, —C(=S)$CH_3$, —C(=S)$NH_2$, —C(=NH)$NH_2$, —C(=NH)OEt, —C(O)NH-cyclopropyl, C(O)$NHCH_2CH_2$-heterocycle, —C(O)$NHCH_2CH_3$, —C(O)$CH_2CH_2NHCH_3$, —$CH_2CH_2F$, —C(O)$CH_2$-heterocycle, —$CH_2C(O)NHCH_3$, —$CH_2CH_2P(O)(CH_3)_2$, Si($CH_3$)$_3$ and the like.

An aliphatic, i.e., alkyl, alkenyl, alkynyl, alkoxy, haloalkyl, cycloalkyl, cycloalkenyl, cycloalkynyl or non-aromatic heterocyclic, group may thus also contain one or more substituents. Examples of suitable substituents on such groups include, but are not limited to those listed above for the carbon atoms of an aryl or heteroaryl group and in addition include the following substituents for a saturated carbon atom: =O, =S, =NH, =$NNR^2R^3$, =NNHC(O)$R^2$, =$NNHCO_2R^2$, or =$NNHSO_2R^2$, wherein $R^2$ at each occurrence is independently H, alkyl, alkenyl, alkynyl, cycloalkyl, cycloalkenyl, cycloalkynyl, aryl, heteroaryl, heterocyclyl.

Illustrative examples of substituents on an aliphatic, heteroaliphatic or heterocyclic group include amino, alkylamino, dialkylamino, aminocarbonyl, halogen, alkyl, alkylaminocar-bonyl, dialkylaminocarbonyl, alkylaminocarbonyloxy, dialkylaminocarbonyloxy, alkoxy, nitro, —CN, carboxy, alkoxycarbonyl, alkylcarbonyl, —OH, haloalkoxy or haloalkyl groups.

Illustrative substituents on a nitrogen, e.g., in an aryl, heteroaryl or non-aromatic heterocyclic ring, include $R^4$, —$NR^2R^3$, —C(=O)$R^2$, —C(=O)$OR^2$, —C(=O)$SR^2$, —C(=O)$NR^2R^3$, —C(=$NR^2$)$NR^2R^3$, —C(=$NR^2$)$OR^2$, —C(=$NR^2$)$R^3$, —$COCOR^2$, —$COMCOR^2$, —CN, —$SO_2R^3$, S(O)$R^3$, —P(=O)($YR^2$)($YR^2$), —$NR^2SO_2R^3$ and —$NR^2SO_2NR^2R^3$, wherein each occurrence of $R^2$ and $R^3$ is independently hydrogen, alkyl, alkenyl, alkynyl, cycloakyl, cycloalkenyl, cycloalkynyl, aryl, heteroary, heterocyclyl.

This invention encompasses only those combinations of substituents and variables that result in a stable or chemically feasible compound. A stable compound or chemically feasible compound is one that has stability sufficient to permit its preparation and detection. Preferred compounds of this invention are sufficiently stable that they are not substantially altered when kept at a temperature of 40° C. or less, in the absence of moisture or other chemically reactive conditions, for at least a week.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diasteriomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound.

Optically active compounds of the invention can be obtained by using active starting materials. These isomers may be in the form of a free acid, a free base, an ester or a salt.

The compounds of this invention can exist in radiolabelled form, i.e., said compounds may contain one or more atoms containing an atomic mass or mass number different from the atomic mass or mass number: ordinarily found in nature. Radioisotopes of hydrogen, carbon, phosphorous, fluorine and chlorine include $^3H$, $^{14}C$, $^{32}P$, $^{35}S$, $^{43}F$ and $^{36}Cl$, respectively. Compounds of this invention which contain those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability.

Radiolabelled compounds of this invention can generally be prepared by methods well known to those skilled in the art. Conveniently, such radiolabelled compounds can be prepared by carrying out the procedures disclosed herein except substituting a readily available radiolabelled reagent for a non-radiolabelled reagent.

4. Synthetic Overview

The practitioner has a well-established literature of heterocyclic and other relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention, including compounds containing the various choices for the $R^t$, $R^a$, $R^b$, $R^c$, $R^d$, $R^e$ and Rings T, A, B, C and D. The following references, and the references cited therein, may be of particular interest: WO 01/27109, WO 02/066478, WO 02/30428, WO 02/080911, WO 02/080914, WO 2004/033453, WO 2004/035578, WO 2004/23972, WO 2005/105798, US 2003/0119842, US 2004/0023972, US 2004/0122044, US 2004/0142961, US 2005/0239822, U.S. Pat. Nos. 6,420,365 and 6,703,404 are referring to the preparation of imidazo[1,2-a]pyridines; WO 05/030218, WO 03/022850 are referring to imidazo[1,2-a]pyrimidines; WO 05/047290, WO 03/089434, U.S. Pat. No. 6,589,952 are referring to imidazopyrazines, WO 04/011466 and U.S. Pat. No. 5,145,850 are referring to the preparation of imidazo[1,2-b]pyridazines; and WO 05/070431, WO 96/35690, WO 04/089471 are referring to pyrazolo[1,5-a]pyrimidines.

Various synthetic approaches may be used to produce the compounds described herein, including those approaches depicted schematically below. The practitioner will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art. See, e.g., "Protective Groups in Organic Synthesis" Third Ed. Greene, T. W. and Wuts, P. G., Eds., John Wiley & Sons, New York: 1999. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). The entire contents of these references are hereby incorporated by reference.

Also, one may chose reagents enriched for a desired isotope, e.g. deuterium in place of hydrogen, to create compounds of this invention containing such isotope(s). Compounds containing deuterium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

The compounds of the this invention can be synthesized using the methods described below, together with synthetic methods known in the art of synthetic organic chemistry, or by a variation thereon as appreciated by those skilled in the art. Preferred methods include, but are not limited to those described below. The reactions are preformed in a solvent appropriate to the reagents and materials employed and suitable for the transformation being effected. It will be understood by those skilled in the art of organic synthesis that the functionality present on the molecule should be consistent the transformations proposed. This will sometimes required some judgment to modify the order of the synthetic steps or to select one particular process scheme over anotherin order to obtain a desired compound of the invention.

A compound of the present invention could be prepared as outlined in Scheme I to Scheme XIX and via standard methods known to those skilled in the art.

A palladium catalyzed Sonogashira coupling reaction is used to link the 'top' Ring T to the 'bottom' [Ring A]-[$L^1$]-[Ring B] moiety as illustrated in Scheme I and II. In Scheme I the Sonogashira coupling reaction is performed with an acetylenic 'top' Ring T and a' [Ring A]-[$L^1$]-[Ring B] moiety which has been activated by the presence of a reactive group, W, which is an I, a Br or another reactive group permitting the desired coupling reaction. The variables in the W-[Ring A]-[$L^1$]-[Ring B] are as defined previously, Rings A and B being substituted with permitted $R^a$ and $R^b$ groups, respectively.

Scheme I: Sonogashira Coupling Reaction

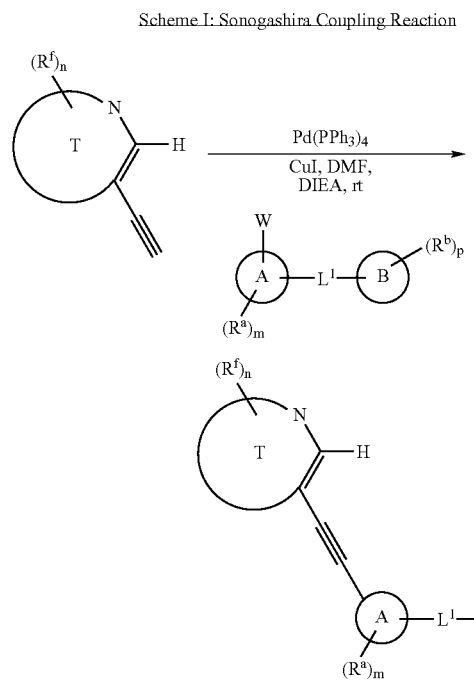

An alternative coupling reaction is described in Scheme II, in which Ring T is "activated" by the presence of a reactive group W (such as I or Br) and is coupled to the 'bottom' acetylenic [RingA]-$L^1$-[RingB] under similar Palladium catalyzed coupling conditions.

Scheme II: Alternative Sonogashira Coupling Reaction

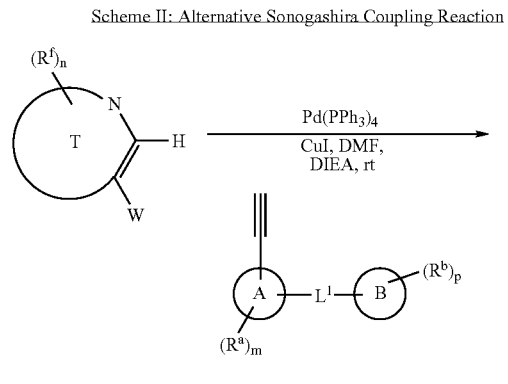

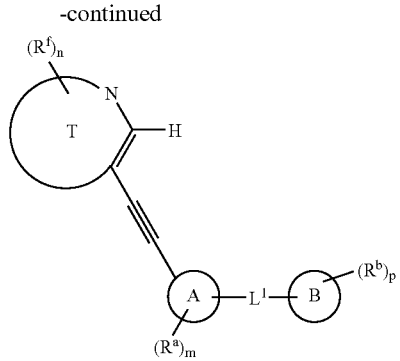

The Sonogashira coupling conditions described in Scheme I and II are applicable to all bicyclic heteroaryl Ring T's and useful to synthesize all compounds of this invention.

Several illustrative overall synthetic approaches to the preparation of the acetylenic Ring T moieties, based on known transformations, are illustrated below in Schemes III to VIII:

Scheme III: Preparation of 3-Ethynylimidazo[1,2-a]pyrazine

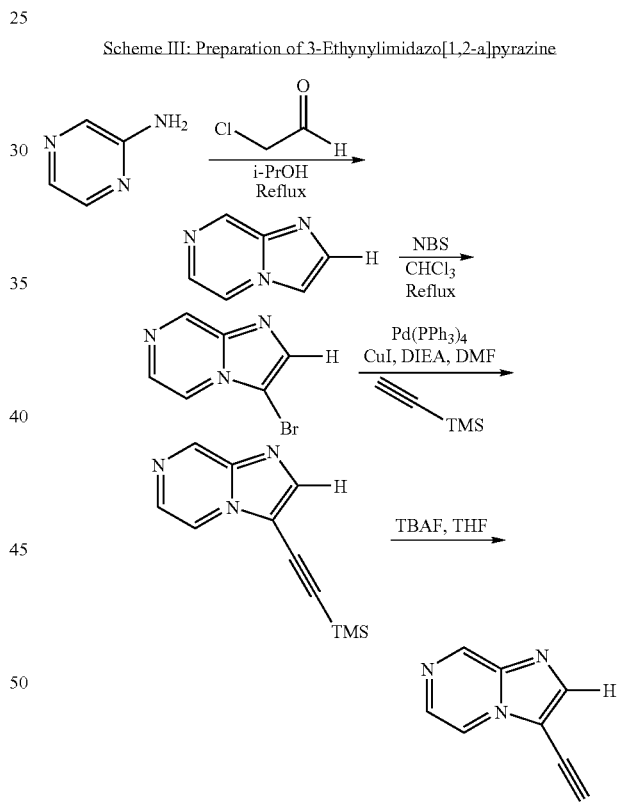

Scheme IV:
Preparation of C-8 Substituted 3-Ethynylimidazo[1,2-a]pyrazines

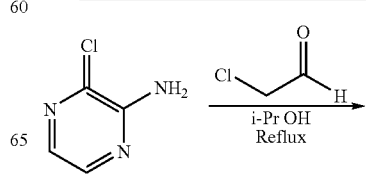

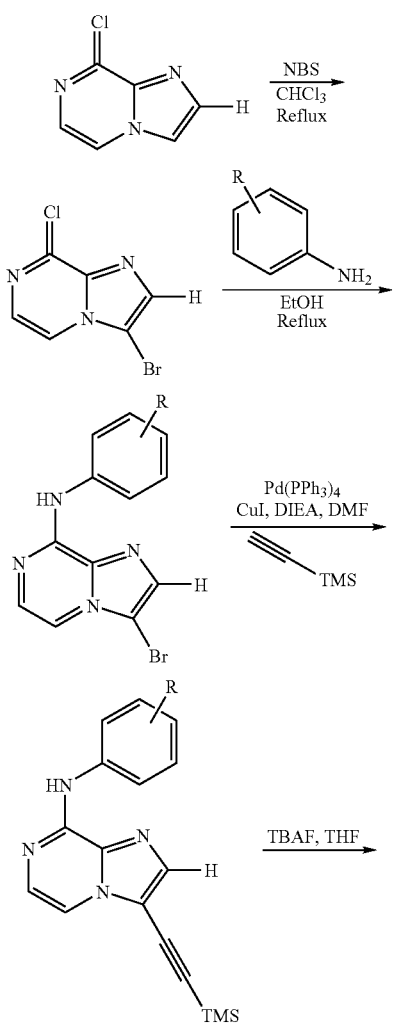
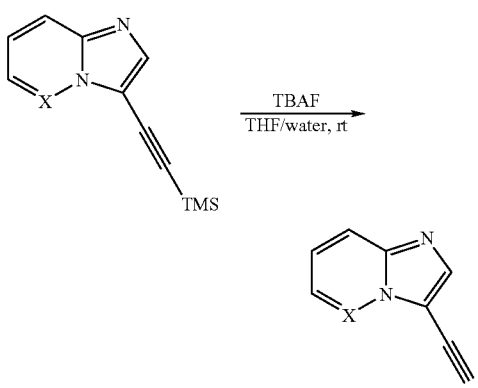
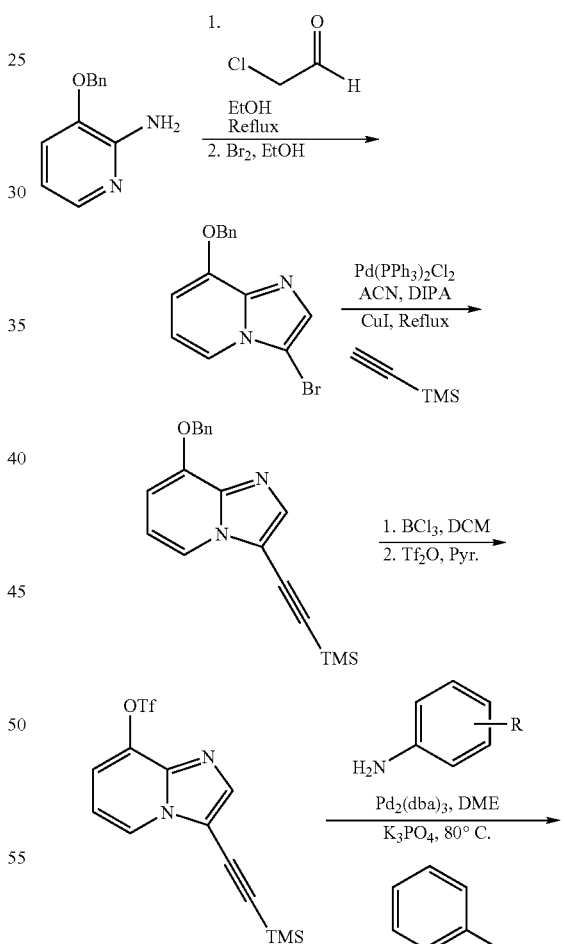
Scheme V:
Preparation of 3-Ethynylimidazo[1,2-a]pyridine
or 3-Ethynylimidazo[1,2-b]pyridazine
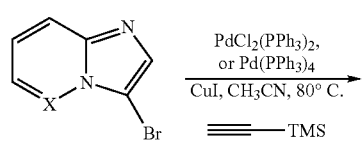
X = CH or N
Scheme VI:
Preparation of C-8 Amino Substituted
3-Ethynylimidazo[1,2-a]pyridines

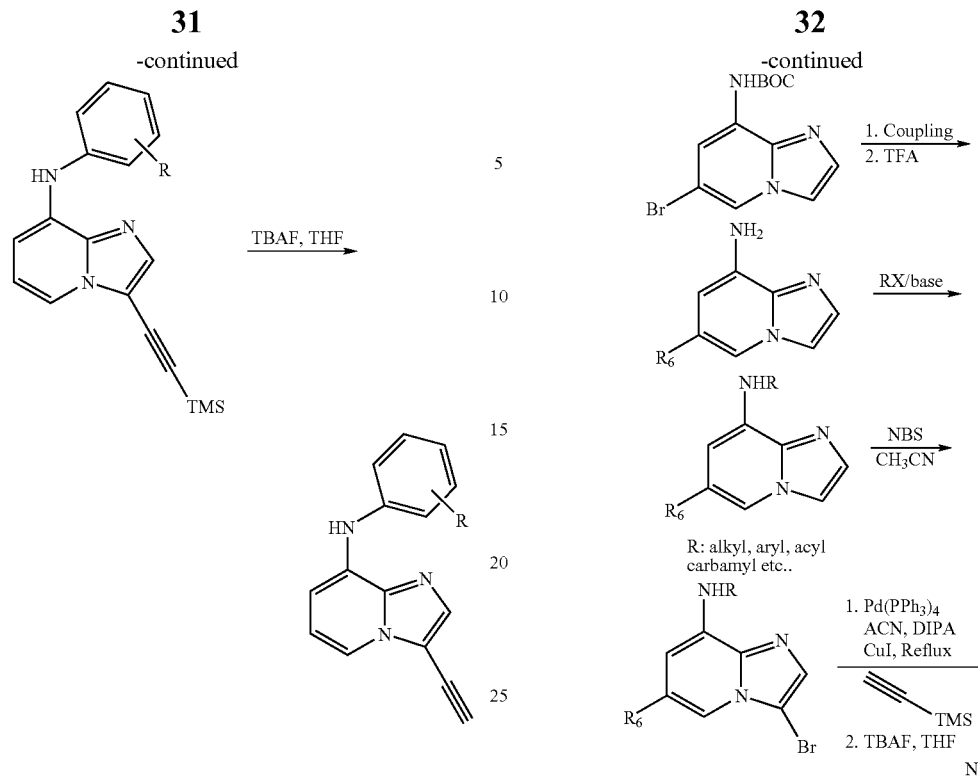

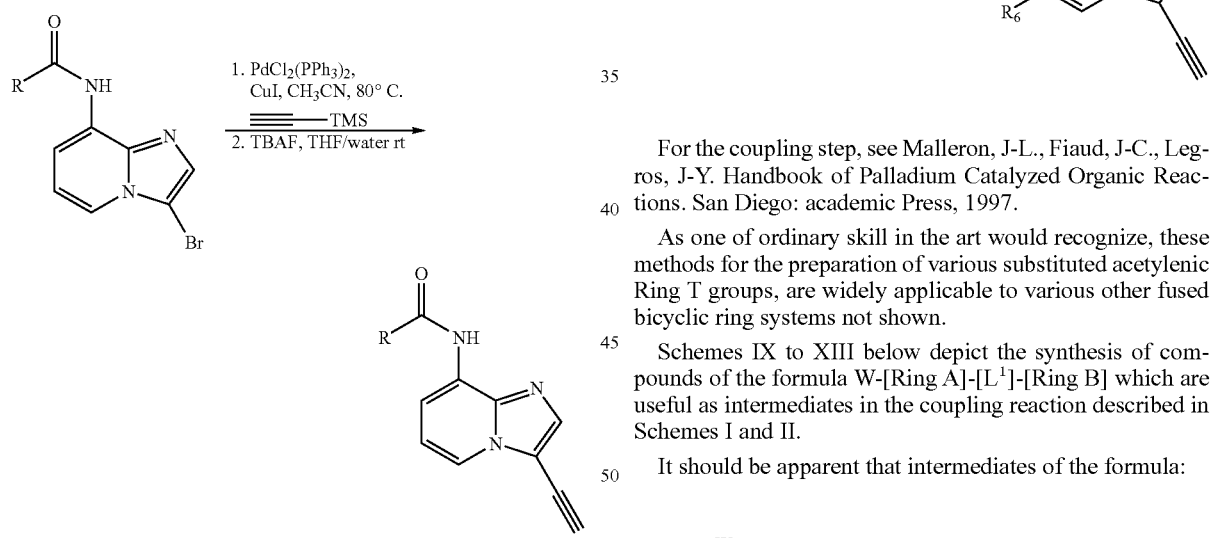

Scheme VII:
Preparation of C-8 substituted 3-Ethynylimidazo[1,2-a]pyridines

Scheme VIII:
Preparation of C-6 and C-8 Substituted 3-Ethynylimidazo[1,2-a]pyridines.

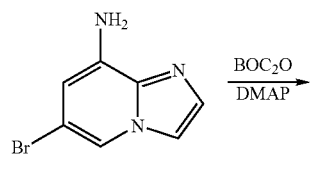

WO2004026867

For the coupling step, see Malleron, J-L., Fiaud, J-C., Legros, J-Y. Handbook of Palladium Catalyzed Organic Reactions. San Diego: academic Press, 1997.

As one of ordinary skill in the art would recognize, these methods for the preparation of various substituted acetylenic Ring T groups, are widely applicable to various other fused bicyclic ring systems not shown.

Schemes IX to XIII below depict the synthesis of compounds of the formula W-[Ring A]-[L$^1$]-[Ring B] which are useful as intermediates in the coupling reaction described in Schemes I and II.

It should be apparent that intermediates of the formula:

are of particular interest as their coupling reaction with the 'top' heteroaryl rings produces compounds of the present invention. The variable groups A, L$^1$ and B are as previously defined and are optionally substituted as described herein, and W is I or an alternative reactive group permitting the desired coupling reaction.

Illustrative such intermediates include among others those of those following structures:

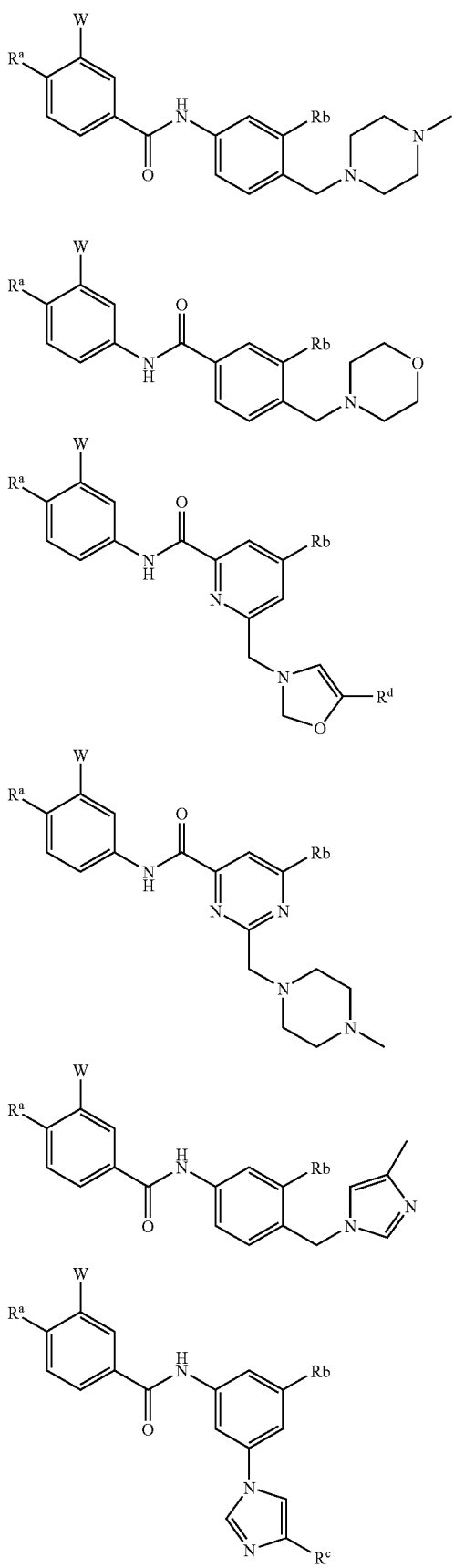

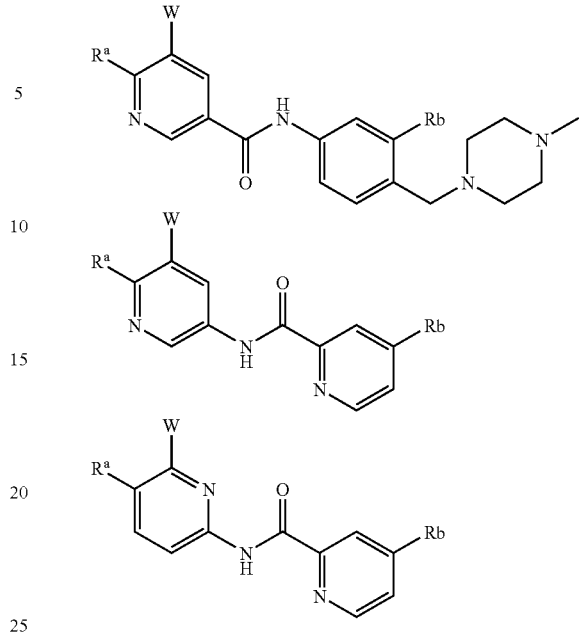

wherein the previously defined variables, e.g., $R^a$, $R^b$, $R^c$ and $R^d$, are as previously defined. For instance, $R^a$ in some embodiments is chosen from F or alkyl, e.g., Me, among others, and $R^b$ in some embodiments is chosen from Cl, F, Me, t-butyl, —$CF_3$ or —$OCF_3$ among others. Those and other compounds of the formula W-[Ring A]-[$L^1$]-[Ring B] with the various permitted substituents are useful for preparing the corresponding compounds of the invention as are defined in the various formulae, classes and subclasses disclosed herein.

Some illustrative synthetic routes for the preparation of reagents and representative intermediates are presented below:

Scheme IX describes an illustrative synthesis of W-[Ring A]-[$L^1$]-[Ring B] in which Rings A and B are phenyl and $L^1$ is NHC(O).

Scheme IX

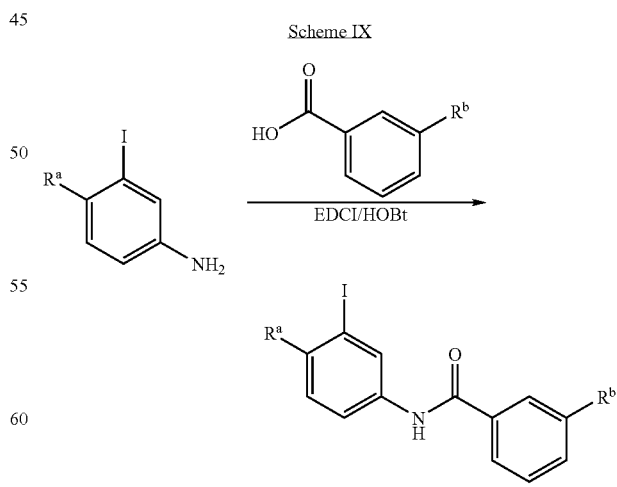

Scheme X depicts the synthesis of a variant of the foregoing in which Ring B is a 2-pyridine and $L^1$ is C(O)NH (i.e., in the other orientation).

Scheme X

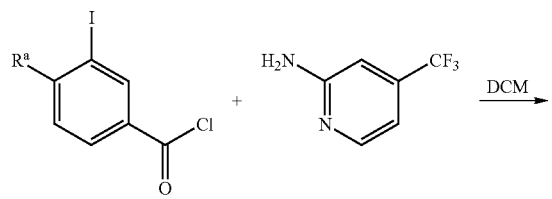

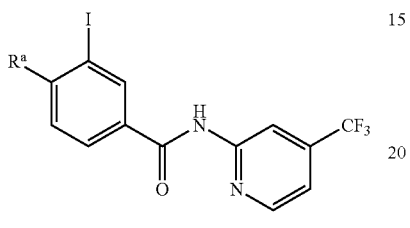

Schemes XI and XII, below, illustrate the synthesis of W-[Ring A]-[$L^1$]-[Ring B] in which Rings A and B are phenyl and Ring C is a heteroaryl ring. These intermediates are useful for making compounds of formula II.

More specifically, Scheme XI describes the preparation of intermediates in which Ring C is an imidazole ring.

Scheme XI

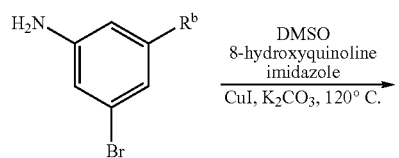

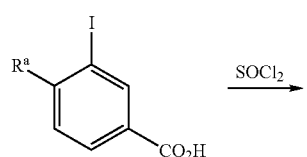

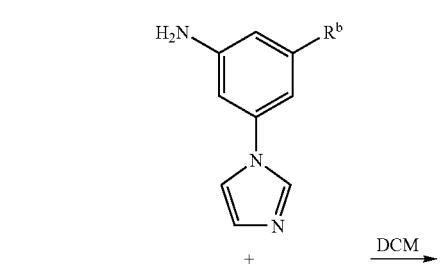

-continued

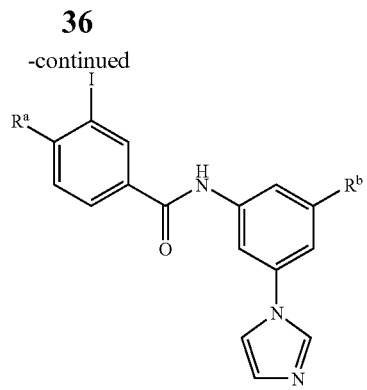

Scheme XII describes the preparation of intermediates in which Ring C is a pyrrole or an oxazole ring.

Scheme XII

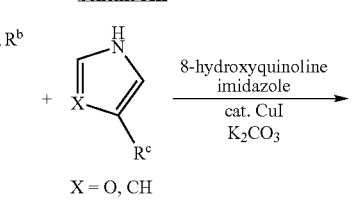

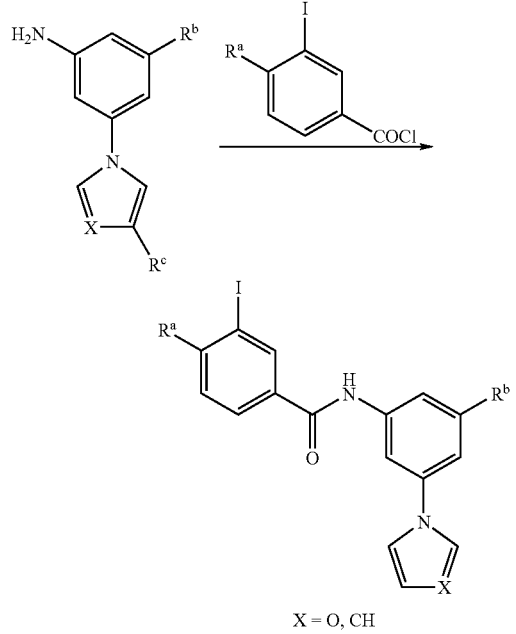

X = O, CH

Scheme XIII illustrates the synthesis of W-[Ring A]-[$L^1$]-[Ring B] in which Rings A and B are phenyl and an $R^b$ substituent is -$L^2$-[Ring D]. These intermediates are useful for making compounds of formula III in which Ring D is a 5 or 6-membered heterocycle, containing one or two heteroatoms.

Scheme XIII

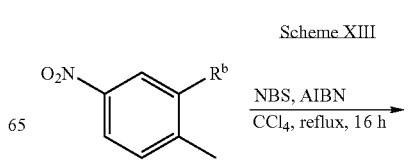

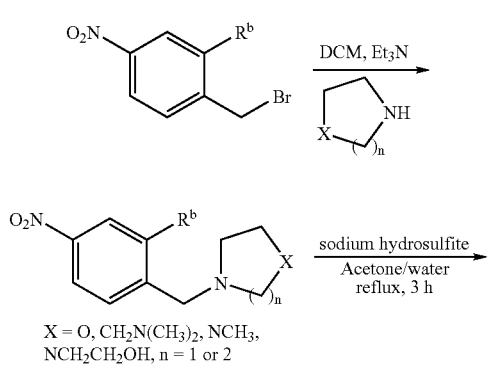

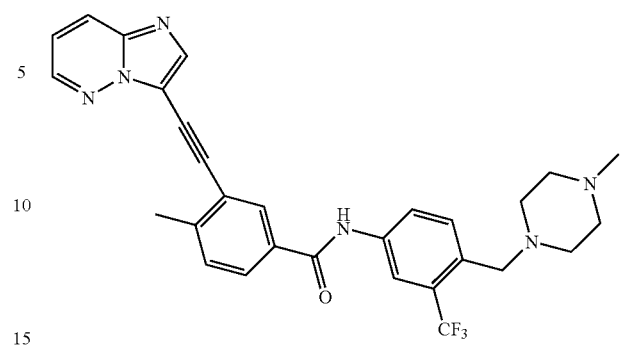

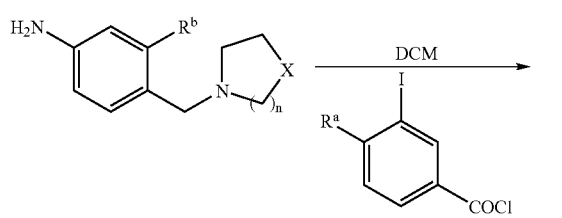

In this scheme, non limiting examples of substituents $R^b$ on Ring B are halo, e.g., Cl; lower alkyl groups, e.g., isopropyl; and substituted lower alkyl groups, e.g. —$CF_3$; and non limiting examples of Ring D are N,N-dimethylpyrrolidine, N-(2-hydroxyethyl)piperazine, and N-methylpiperazine.

Intermediates W-[Ring A]-[$L^1$][Ring B], such as those presented in the various synthetic schemes above, can be reacted with an acetylenic Ring T using the Sonogashira coupling conditions described in the general Scheme I.

An example is depicted below in Scheme XIV, in which Ring T moiety can be further derivatized after the Sonogashira coupling step, to generate various interesting substituted analogs of this invention.

Scheme XIV

Alternatively, the W-[Ring A]-[$L^1$]-[Ring B] can be reacted under Sonogashira conditions with trimethylsilylacetylene, prior to the coupling with an iodo- or a bromo-activated Ring T as otherwise described in the general Scheme II.

An example is depicted in Scheme XV:

Scheme XV

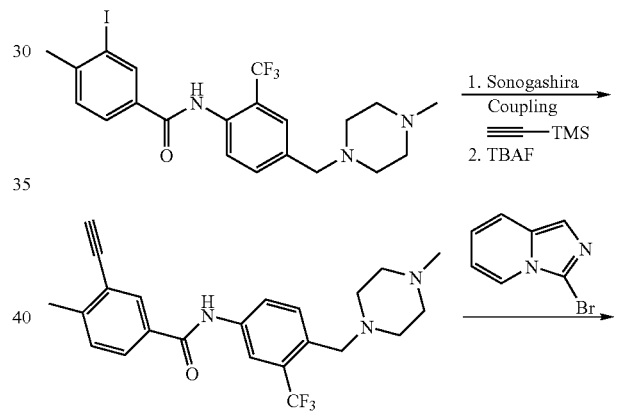

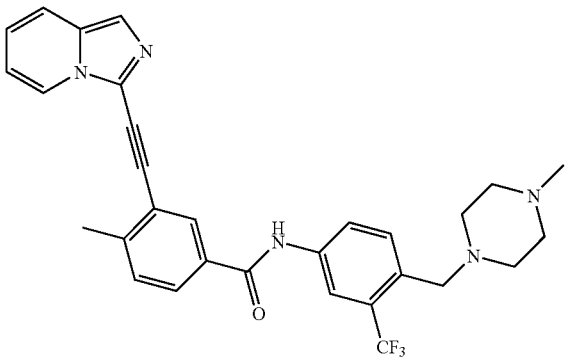

In other embodiments, the steps can be carried out in a different order. For example, the Sonogashira Coupling reaction can be used to Ring T to Ring A prior to linking that portion to Ring B and/or [Ring B]-[$L^2$]-[Ring D] and/or [Ring B]-[Ring C] as shown in Scheme XVI.

Scheme XVI

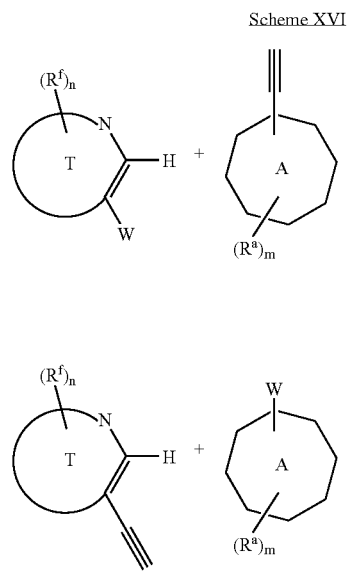

In a non-limiting example in which Ring A and Ring B are phenyl and $L^1$ is CONH, Scheme XVII describes Sonogashira Coupling of an acetylenic Ring T with 3-iodo-4-methylbenzoic acid (a Ring A moiety) to generate a [Ring T]-[Ring A] intermediate which then undergoes an amide coupling with an optionally substituted Ring B moiety:

Scheme XVII

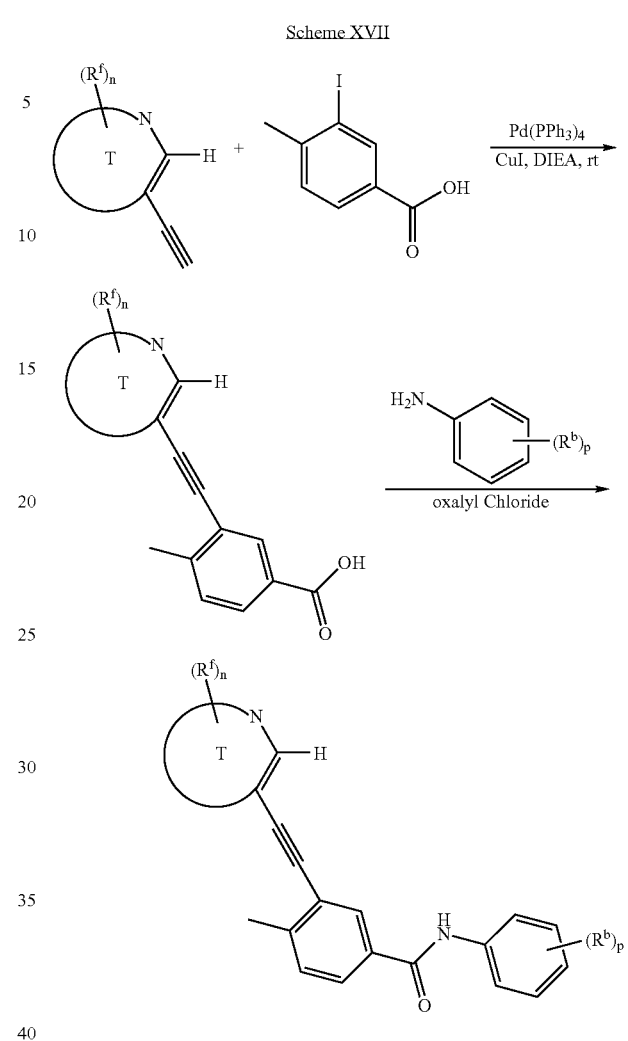

This approach is illustrated in Scheme XVIII which depicts the coupling of an acetylenic Ring T (i.e., 3-ethynylimidazo[1,2-b]pyridazine) with a substituted W-[Ring A] (i.e., 3-iodo-4-methylbenzoic acid), followed by an amide coupling of the resultant [Ring T]-[Ring A]-COOH intermediate with a $H_2N$-[Ring B]-L2-[Ring C] moiety (i.e., 4-((4-methylpiperazin-1-yl)methyl)-3-(trifluoromethylaniline):

Scheme XVIII

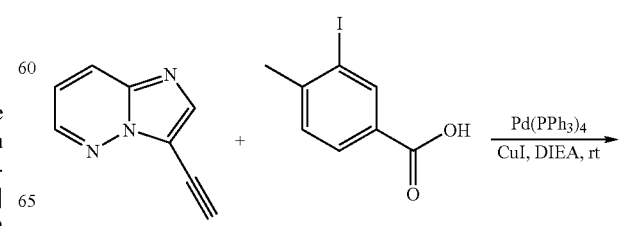

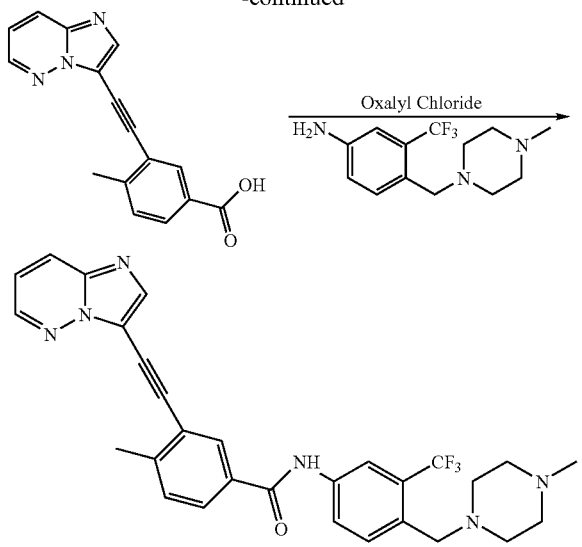

Alternatively, as another illustration of the practitioner's range of assembly options, the 3-iodo-4-methylbenzoic acid Ring A intermediate can be reacted in a Sonogashira reaction with trimethylsilylacetylene, which after silyl deprotection, can a second Sonogashira coupling reaction with an activated Ring T as illustrated in Scheme XIX.

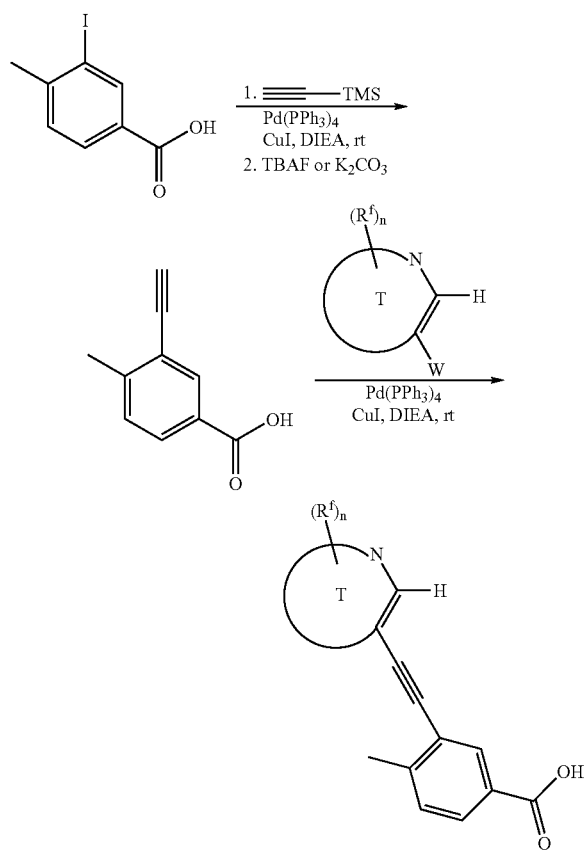

With synthetic approaches such as the foregoing, combined with the examples which follow, additional information provided herein and conventional methods and materials, the practitioner can prepare the full range of compounds disclosed herein.

5. Uses, Formulations, Administration

Pharmaceutical Uses; Indications

This invention provides compounds having biological properties which make them of interest for treating or ameliorating diseases in which kinases may be involved, symptoms of such disease, or the effect of other physiological events mediated by kinases. For instance, a number of compounds of this invention have been shown to inhibit tyrosine kinase activity of Src and abl, among other tyrosine kinases which are believed to mediate the growth, development and/ or metastasis of cancer. A number of compounds of the invention have also been found to possess potent in vitro activity against cancer cell lines, including among others K-562 leukemia cells. Observed potencies have been as much as 10-fold more powerful than Gleevec in conventional antiproliferation assays with K562 cells.

Such compounds are thus of interest for the treatment of cancers, including both primary and metastatic cancers, including solid tumors as well as lymphomas and leukemias (including CML, AML and ALL), and including cancers which are resistant to other therapies, including other therapies involving the administration of kinase inhibitors such as Gleevec, Tarceva or Iressa.

Such cancers include, among others, cancers of the breast, cervix, colon and rectum, lung, ovaries, pancreas, prostate, head and neck, gastrointestinal stroma, as well as diseases such as melanoma, multiple myeloma, non-Hodgkin's lymphoma, melanoma, gastric cancers and leukemias (e.g., myeloid, lymphocytic, myelocytic and lymphoblastic leukemias) including cases which are resistant to one or more other therapies, including among others, Gleevec, Tarceva or Iressa.

Resistance to various anticancer agents can arise from one or more mutations in a mediator or effector of the cancer (e.g., mutation in a kinase such as Src or Abl) which correlate with alteration in the protein's drug binding properties, phosphate binding properties, protein binding properties, autoregulation or other characteristics. For example, in the case of BCR-Abl, the kinase associated with chronic myeloid leukemia, resistance to Gleevec has been mapped to a variety of BCR/Abl mutations which are linked to a variety of functional consequences, including among others, steric hindrance of drug occupancy at the kinase's active site, alteration in deformability of the phosphate binding P loop, effects on the conformation of the activation loop surrounding the active site, and others. See e.g. Shah et al, 2002, Cancer Cell 2, 117-125 and Azam et al, 2003, Cell 112, 831-843 and references cited therein for representative examples of such mutations in Bcr/ Abl which correlate with drug resistance. See also the following references for additional background information on BCR/Abl, its mechanistic role in CML and drug-resistance-conferring mechanisms and mutations: Kurzrock et al., Philadelphia chromosome-positive leukemias: from basic mechanisms to molecular therapeutics, Ann Intern Med. 2003 May 20; 138(10):819-30; O'Dwyer et al., Demonstration of Philadelphia chromosome negative abnormal clones in patients with chronic myelogenous leukemia during major cytogenetic responses induced by imatinib mesylate. Leukemia. 2003 March; 17(3):481-7; Hochhaus et al., Molecular and chromosomal mechanisms of resistance to imatinib (STI571) therapy, Leukemia. 2002 November; 16(11):2190-6; O'Dwyer et al., The impact of clonal evolution on response to imatinib mesylate (STI571) in accelerated phase CML. Blood. 2002 Sep. 1; 100(5): 1628-33; Braziel et al., Hematopathologic and cytogenetic findings in imatinib mesylate-treated chronic myelogenous leukemia patients: 14 months' experience. Blood. 2002 Jul. 15; 100(2):435-41; Corbin et al., Analysis of the structural basis of specificity of inhibition of the Abl kinase by STI571, J Biol Chem. 2002 Aug. 30; 277 (35):32214-9; Wertheim et al., BCR-ABL-induced adhesion defects are tyrosine kinase-independent. Blood. 2002 Jun. 1; 99(11):4122-30; Kantarjian et al., Hematologic and cytogenetic responses to imatinib mesylate in chronic myelogenous leukemia, N Engl J Med. 2002 Feb. 28; 346(9):645-52, Erratum in: N Engl J Med 2002 Jun. 13; 346(24): 1923; Hochhaus et al., Roots of clinical resistance to STI-571 cancer therapy. Science. 2001 Sep. 21; 293(5538):2163; Druker et al., Activity of a specific inhibitor of the BCR-ABL tyrosine kinase in the blast crisis of chronic myeloid leukemia and acute lymphoblastic leukemia with the Philadelphia chromosome. N Engl J Med. 2001 Apr. 5; 344(14):1038-42, Erratum in: N Engl J Med 2001 Jul. 19; 345(3):232; Mauro et al., Chronic myelogenous leukemia. Curr Opin Oncol. 2001 January; 13(1):3-7, Review; Kolibaba et al., CRKL binding to BCR-ABL and BCR-ABL transformation. Leuk Lymphoma. 1999 March; 33(1-2):119-26; Bhat et al., Interactions of p62(dok) with p210(bcr-abl) and Bcr-Abl-associated proteins. J Biol Chem. 1998 Nov. 27; 273(48):32360-8; Senechal et al., Structural requirements for function of the Crkl adapter protein in fibroblasts and hematopoietic cells. Mol Cell Biol. 1998 September; 18(9):5082-90; Kolibaba et al., Protein tyrosine kinases and cancer. Biochim Biophys Acta. 1997 December 9; 1333(3):F217-48, Review; Heaney et al., Direct binding of CRKL to BCR-ABL is not required for BCR-ABL transformation. Blood. 1997 Jan. 1; 89(1):297-306; Hallek et al., Interaction of the receptor tyrosine kinase p145c-kit with the p210Obcr/abl kinase in myeloid cells. Br J Haematol. 1996 July; 94(1):5-16; Oda et al., The SH2 domain of ABL is not required for factor-independent growth induced by BCR-ABL in a murine myeloid cell line. Leukemia. 1995 Feb.; 9(2):295-301; Carlesso et al., Use of a temperature-sensitive mutant to define the biological effects of the p210BCR-ABL tyrosine kinase on proliferation of a factor-dependent murine myeloid cell line. Oncogene. 1994 January; 9(1):149-56.

Again, we contemplate that compounds of this invention, both as monotherapies and in combination therapies, will be useful against leukemias and other cancers, including those which are resistant in whole or part to other anticancer agents, specifically including Gleevec and other kinase inhibitors, and specifically including leukemias involving one or more mutations in BCR/Abl, within or outside the kinase domain, including but not limited to those noted in any of the foregoing publications. See in particular Azam et al. and references cited therein for examples of such mutations in BCR/Abl, including, among others, mutations in the drug binding cleft, the phosphate binding P loop, the activation loop, the conserved VAVK of the kinase beta-3 sheet, the catalytic alpha-1 helix of the small N lobe, the long alpha-3 helix within the large C lobe, and the region within the C lobe downstream of the activation loop.

Pharmaceutical Methods

The method of the invention comprises administering to a subject in need thereof a therapeutically effective amount of a compound of the invention.

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like.

The compound, or a composition containing the compound, may be administered using any amount and any route of administration effective for killing or inhibiting the growth of tumors or other forms of cancer.

The anticancer compounds of the invention are preferably formulated in dosage unit form for ease of administration and uniformity of dosage. The expression "dosage unit form" as used herein refers to a physically discrete unit of anticancer agent appropriate for the patient to be treated. As is normally the case, the total daily usage of the compounds and compositions of the present invention will be decided by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; drugs used in combination or coincident with administration of the compound of this invention; and like factors well known in the medical arts.

Furthermore, after formulation with an appropriate pharmaceutically acceptable carrier in a desired dosage, the compositions of this invention can be administered to humans and other animals orally, rectally, parenterally, intracisternally, intravaginally, intraperitoneally, topically (as by transdermal patch, powders, ointments, or drops), sublingually, bucally, as an oral or nasal spray, or the like.

The effective systemic dose of the compound will typically be in the range of 0.01 to 500 mg of compound per kg of patient body weight, preferably 0.1 to 125 mg/kg, and in some cases 1 to 25 mg/kg, administered in single or multiple doses. Generally, the compound may be administered to patients in need of such treatment in a daily dose range of about 50 to about 2000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repititions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

The amount of compound which will be effective in the treatment or prevention of a particular disorder or condition will depend in part on well known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the compound of this invention may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the compound of this invention is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

Regarding the Compounds

Compounds of present invention can exist in free form for treatment, or where appropriate, as a pharmaceutically acceptable salt or other derivative. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the isolation and purification of the compounds of the invention, or separately by reacting the free base or free acid of a compound of the invention with a suitable base or acid, respectively. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methane-sulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluene-sulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Additionally, as used herein, the term "pharmaceutically acceptable ester" refers preferably to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. Obviously, esters can be formed with a hydroxyl or carboxylic acid group of the compound of the invention.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed in vivo to yield the parent compound of the above formula, for example by hydrolysis in blood. See, e.g., T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Assocn. and Pergamon Press, 1987, both of which are incorporated herein by reference.

Compositions

Compositions are provided which comprise any one of the compounds described herein (or a prodrug, pharmaceutically acceptable salt or other pharmaceutically acceptable derivative thereof, and one or more pharmaceutically acceptable carriers or excipients. These compositions optionally further comprise one or more additional therapeutic agents. Alternatively, a compound of this invention may be administered to a patient in need thereof in combination with the administration of one or more other therapeutic regimens (e.g. Gleevec or other kinase inhibitors, interferon, bone marrow transplant, farnesyl transferase inhibitors, bisphosphonates, thalidomide, cancer vaccines, hormonal therapy, antibodies, radiation, etc). For example, additional therapeutic agents for conjoint administration or inclusion in a pharmaceutical composition with a compound of this invention may be another one or more anticancer agents.

As described herein, the compositions of the present invention comprise a compound of the invention together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Formulations

This invention also encompasses a class of compositions comprising the active compounds of this invention in association with one or more pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A typical daily dose is in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner.

While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the socalled emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w. Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. Pharmaceutically acceptable carriers, adjuvants and vehicles that may be used in the pharmaceutical compositions of this invention include, but are not limited to, ion exchangers, alumina, aluminum stearate, lecithin, selfemulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of compounds of the formulae described herein.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening, flavoring and/or coloring agents may be added. The pharmaceutical compositions may comprise formulations utilizing liposome or microencapsulation techniques, various examples of which are known in the art.

The pharmaceutical compositions may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

Combinations

While the compounds of the invention can be administered as the sole active pharmaceutical agent, they can also be used in combination with one or more other compounds of the invention or with one or more other agents. When administered as a combination, the therapeutic agents can be formulated as separate compositions that are administered at the same time or sequentially at different times, or the therapeutic agents can be given as a single composition.

The phrase "combination therapy", in referring to the use of a compound of this invention together with another pharmaceutical agent, means the coadministration of each agent in a substantially simultaneous manner as well as the administration of each agent in a sequential manner, in either case, in a regimen that will provide beneficial effects of the drug combination. Coadministration includes inter alia the simultaneous delivery, e.g., in a single tablet, capsule, injection or other dosage form having a fixed ratio of these active agents, as well as the simultaneous delivery in multiple, separate dosage forms for each agent respectively.

Thus, the administration of compounds of the present invention may be in conjunction with additional therapies known to those skilled in the art in the prevention or treatment of cancer, such as radiation therapy or cytostatic agents, cytotoxic agents, other anti-cancer agents and other drugs to amerliorate symptoms of the cancer or side effects of any of the drugs.

If formulated as a fixed dose, such combination products employ the compounds of this invention within the accepted dosage ranges. Compounds of this invention may also be administered sequentially with other anticancer or cytotoxic agents when a combination formulation is inappropriate. The invention is not limited in the sequence of administration; compounds of this invention may be administered prior to, simulateously with, or after administration of the other anticancer or cytotoxic agent.

Currently, standard treatment of primary tumors consists of surgical excision, when appropriate, followed by either radiation or chemotherapy, and typically administered intravenously (IV). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention includes antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, CibaGeigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5fluorouracil, N-(21-furanidyl) fluorouracil, Daiichi Seiyaku FO-152, isopropyl pyrrolizine, Lilly LY-1 88011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D 384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G M, Chinoin GYKI-17230, hepsulfam, ifosfamide, iproplatin, lomustine, mafosfamide, mitolactolf Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN II, Ajinomoto AN3, Nippon Soda anisomycins, anthracycline, azino-mycin-A, bisucaberin, Bristol-Myers BL-6859, Bristol-Myers BMY-25067, Bristol-Myers BNY-25551, Bristol-Myers BNY-26605 IBristolMyers BNY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko, DC89-AI, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AI, esperamicin-Alb, Erbamont FCE21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of (xcarotene, (X-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1F Henkel APD, aphidicolin glycinate, asparaginase, Avarol, baccharin, batracylin, benfluron, benzotript, Ipsen-Beaufour BIM-23015, bisantrene, BristoMyers BNY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, WarnerLambert CI-937, Warner-Lambert CI-941, Warner-Lambert C1958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704t gallium nitrate, genkwadaphnin, Chugai GLA-43, Glaxo GR-63178, grifolan NMF5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU 1121 Lilly LY-186641, NCI (US) MAP, marycin, Merrel Dow MDL-27048, Medco MEDR-340, merbarone, merocyanlne derivatives, methylanilinoacridine, Molecular Genetics MGI136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, WarnerLambert PD-11707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM Alternatively, the present compounds may also be used in co-therapies with other antineoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon1, interferon alpha, natural, interferon beta, interferon beta-Ia, interferon beta-Ib, interferon gamma, natural interferon gamma-Ia, interferon gamma-Ib, interleukin-I beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinidel filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM iodine 131 MAb (Techniclone), polymorphic epithelial mucin-yttrium 90 MAb (Antisoma), marimastat, menogaril, mitumomab, motexafin, gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

The following representative examples contain important additional information, exemplification and guidance which can be adapted to the practice of this invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein. The contents of those cited references are incorporated herein by reference to help illustrate the state of the art. In addition, for purposes of this invention, the chemical elements are identified in accordance with the Periodic Table of the Elements, CAS version, Handbook of Chemistry and Physics, 75$^{th}$ Ed., inside cover. Additionally, general principles of organic chemistry, as well as specific functional moieties and reactivity, are described in "Organic Chemistry", Thomas Sorrell, University Science Books, Sausalito: 1999, and "Organic Chemistry", Morrison & Boyd (3d Ed), the entire contents of both of which are incorporated herein by reference.

EXAMPLES

Some of the compounds described in the following examples have been converted into an HCl salt. The general procedure for generating HCl salts is described below:

To the final product was added just enough MeOH saturated with HCl (g) to dissolve, cooled to 0° C. for 0.5-1 h, filtered, washed solid with ice cold MeOH then Et$_2$O, and the resulting solid dried in a vacuum desiccator to provide in most cases the tris HCl salt.

Example 1

N-(3-(1H-imidazol-1-yl)-5-(trifluoromethyl)phenyl)-3-(imidazo[1,2-a]pyrazin-3-ylethynyl)-4-methylbenzamide

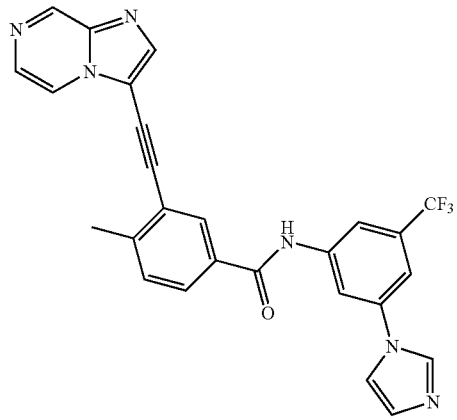

Imidazo[1,2-a]pyrazine: A solution of aminopyrazine (1 g, 10.5 mmol) and chloroacetaldehyde (50% wt in H$_2$O; 1.98 g, 12.6 mmol) in 1.6 mL of EtOH was heated at 90° C. in a sealed tube for 5 h. Upon cooling to ambient temperature, the reaction mixture was concentrated and diluted with dichloromethane (DCM). The organic layer washed with saturated aqueous NaHCO$_3$ then dried over MgSO$_4$ and concentrated. The crude product was purified by silica gel flash chromatography (eluted with 10% MeOH/DCM) to provide 0.8 g of product.

3-((Trimethylsilyl)ethynyl)imidazo[1,2-a]pyrazine: A mixture of 3-bromoimidazo[1,2-a]pyrazine (0.15 g, 0.76 mmol; prepared according to J. Bradac, et al. *J. Org. Chem.* (1977), 42, 4197-4201), 0.09 g (0.91 mmol) of ethynyltrimethylsilane, 0.044 g (0.038 mmol) of Pd(PPh$_3$)$_4$, 0.014 g (0.076 mmol) of CuI, and 0.26 mL (1.52 mmol) of diisopropylethylamine in 3.8 mL of DMF was heated at 50° C. overnight under an atmosphere of N$_2$. Upon cooling to ambient temperature, the reaction mixture was concentrated and the crude product was purified by silica gel flash chromatography (eluted with 50% EtOAc/hexanes) to provide 0.15 g of product: 216 m/z (M+H).

3-Ethynylimidazo[1,2-a]pyrazine: To a solution of 3-((Trimethylsilyl)ethynyl)imidazo [1,2-a]pyrazine (0.15 g, 0.7 mmol) in 3.5 mL of THF was added 1.05 mL (1.05 mmol) of tetrabutylammonium fluoride (1.0M in THF) at ambient temperature. The solution was stirred for 15 min, concentrated, and the crude product purified by silica gel flash chromatography (eluted with 50% EtOAc/hexanes) to provide 0.078 g of product.

3-(1H-imidazol-1yl)-5-(trifluoromethyl)aniline: A mixture of 3-Amino-5-bromobenzotrifluoride (4.0 g, 0.0167 mol), 8-hydroxy quinoline (0.362 g, 0.0025 mol), CuI (0.476 g, 0.025 mol), imidazole (1.36 g, 0.0199 mol), and potassium carbonate (2.52 g, 0.0183 mol) in 17 mL of DMSO (degassed with argon for ~10 min) was heated at 120° C. under an atmosphere of argon for 15 h; the HPLC indicated no starting material. A 14% aqueous solution of ammonium hydroxide was added to the cooled mixture and this was stirred for 1 h at ambient temperature. Water (50 mL) and EtOAc (200 mL) were added and the aqueous layer was extracted with EtOAc (3×30 mL). The combined organic layers were dried over Na₂SO₄ and concentrated. The crude product was purified by silica gel flash chromatography (eluted with EtOAc/hexanes) to provide 2.51 g of product.

N-(3-(1H-imidazol-1-yl)-5-(trifluomethyl)phenyl)-3-iodo-4-methylbenzamide: To 3-Iodo-4-methylbenzoic acid (3.07 g, 0.0117 mol) was added thionyl chloride (10 mL) and refluxed for 2 h. The excess thionyl chloride was carefully removed and the resulting acid chloride was dried in vacuo for 2 h. The residue was then dissolved in DCM (anhydrous, 25 mL) and cooled on ice. To the cooled solution was added 3-(1H-imidazol-1-yl)-5-(trifluoromethyl)aniline 5 (3.46 g, 0.0152 mol) in DCM followed by the dropwise addition of diisopropylethylamine (8.2 mL, 0.047 mol). This was stirred at ambient temperature for 21 h. The white solid that separated was filtered and washed with water and dried to provide 4.65 g of product. Additional product could be obtained from the filtrate following concentration and purification by silica gel flash chromatography in EtOAc/hexanes.

N-(3-(1H-imidazol-1-yl)-5-(trifluoromethyl)phenyl)-3-(imidazo[1,2-a]pyrazin-3-ylethynyl)-4-methylbenzamide: A mixture of 3-Ethynylimidazo[1,2-a]pyrazine (0.075 g, 0.52 mmol), 0.245 g (0.52 mmol) of N-(3-(1H-imidazol-1-yl)-5-(trifluoromethyl)phenyl)-3-iodo-4-methylbenzamide, 0.030 g (0.026 mmol) of Pd(PPh₃)₄, 0.007 g (0.039 mmol) of CuI, and 0.14 mL (0.78 mmol) of diisopropylethylamine in 3.0 mL of DMF was stirred at ambient temperature overnight under an atmosphere of N₂. The reaction mixture was concentrated and the crude product was purified by silica gel flash chromatography (eluted with 10% EtOAc/hexanes, then 100% EtOAc, then 10% MeOH/EtOAc) to provide 0.090 g of product as a solid: 487 m/z (M+H).

Alternative Synthesis of N-(3-(1H-imidazol-1-yl)-5-(trifluoromethyl)phenyl)-3-(imidazo[1,2-a]pyrazin-3-ylethynyl)4-methylbenzamide 3-((Trimethylsilyl)ethynyl)imidazo[1,2-a]pyrazine can be prepared as described previously. In one variation, the reaction can also be carried out in THF instead of DMF. The crude product can also be purified by silica gel pad chromatography (eluted with ethyl acetate/hexane) and a brief treatment with activated charcoal (Darco) can be carried out to help further reduce contamination with the homo coupling product.

3-Ethynylimidazo[1,2-a]pyrazine: To a solution of 3-((trimethylsilyl)ethynyl) imidazo[1,2-a]pyrazine (1.39 mol) in 10× volume of Ethyl acetate and 1.5× volume of Methanol is added two and a half equivalents of potassium carbonate at ambient temperature and the solution stirred for 1 hour. Potassium carbonate is filtered off and the organic stream is washed with water and with saturated sodium chloride solution (two or more times). Aqueous phases can be combined and re-extracted with ethyl acetate. Organic streams can then be combined and concentrated under vacuum to about 0.5 L. Solids can be allowed to precipitate out upon concentration. Slurry is cooled, e.g. to about −5° C., stored overnight, filtered, and washed with about 0.3 L of cold ethyl acetate. The solids can then be dried under vacuum.

3-(imidazo[1,2-a]pyrazin-3-ylethynyl)-4-methylbenzoic acid can be prepared in a manner similar to that described above for the Sonogashira reaction. 3-Ethynylimidazo[1,2-a]pyrazine and 3-iodo-4-methylbenzoic acid are used as coupling partners. Alternatively, the solvent (DMF) can be replaced by ethyl acetate and the base (Hunig base) can be replaced by triethylamine. The product can be isolated by filtration of the crude reaction mixture. The filter cake is washed sequentially with a solvent such as ethyl acetate and then water, then dried in a vacuum oven. Further purification can be achieved by slurrying the solids in water adjusted to pH 3 with the addition of concentrated HCl. After filtration and water wash, the product can be dried in a vacuum oven.

N-(3-(1H-imidazol-1-yl)-5-(trifluoromethyl)phenyl)-3-(imidazo[1,2-a]pyrazin-3-ylethynyl)-4-methylbenzamide: 3-(imidazo[1,2-a]pyrazin-3-ylethynyl)-4-methylbenzoic acid (18 mmol) is dissolved in methylene chloride (100 mL). To this solution is added 3 equivalents of 4-methylmorpholine (NMM) followed by 1.05 equivalents of oxalyl chloride. After stirring at ambient temperature for 30 minutes, 0.8 equivalents of 3-(1H-imidazol-1-yl)-5-(trifluoromethyl)aniline (prepared as above) is added along with 5 mole % of DMAP. After initially stirring at ambient temperature, the mixture is brought to reflux and stirred overnight. After 16 h an additional 0.2 equivalents of the aniline is added, bringing the total charge to 1 equivalent. The mixture can then be stirred for an additional 2 h, quenched with water, and the layers separated. The aqueous layer can be extracted with methylene chloride (2×50 mL) and the combined extracts can be washed with water. The combined methylene chloride layers can then be evaporated and the residue dissolved in 100 mL of ethyl acetate (20 mL). After standing for 1 h, the product is allowed to crystallize. The mixture is cooled, e.g. to 0° C., filtered, and the solid product is washed with cold ethyl acetate.

N-(3-(1H-imidazol-1-yl)-5-(trifluoromethyl)phenyl)-3-(imidazo[1,2-a]pyrazin-3-ylethynyl)-4-methylbenzamide mono hydrochloride salt N-(3-(1H-imidazol-1-yl)-5-(trifluoromethyl)phenyl)-3-(imidazo[1,2-a]pyrazin-3-ylethynyl)-4-methylbenzamide (0.94 mmol) can be suspended in MeCN (10 ml) and heated with stirring to a temperature of 45 to 55° C. (hot plate temperature). Hydrochloric acid (1.1 eq 1M solution in EtOH) is added to obtain dissolution. Within a few minutes, a precipitate is allowed to form. The suspension can be cooled to ambient temperature and then filtered and washed with MeCN (1×1.5 ml liquors+1×1.5 ml fresh). The solid can be dried at 50° C. under vacuum to constant weight.

Example 2

3-(Imidazo[1,2-a]pyrazin-3-ylethynyl)-4-methyl-N-(4-((4-methylpiperazin-1-yl)methyl)-3-(trifluoromethyl)phenyl)benzamide

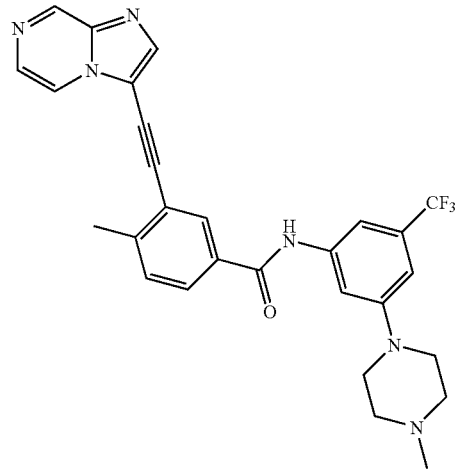

The title compound was synthesized from 3-ethynylimidazo[1,2-a]pyrazine and 3-iodo-4-methyl-N-(4-((4-methylpiperazin-1-yl)methyl)-3-(trifluoromethyl)phenyl)benzamide in a manner similar to that described for Example 1, The product was obtained as a solid: 533 m/z (M+H).

1-(Bromomethyl)-4-nitro-2-(trifluoromethyl)benzene: A suspension of 2-methyl-5-nitrobenzotrifluoride (3.90 g, 19 mmol), N-bromosuccinimide (NBS, 3.56 g, 20 mmol), 2,2'-azobis(2-methylpropionitrile) (AIBN, 94 mg, 0.6 mmol) in CCl$_4$ (40 mL) was refluxed under N$_2$ for 16 h. HPLC indicated ca. 50% conversion. More NBS (10 mmol) and AIBN (0.6 mmol) was added, and the mixture was refluxed for another 14 h. HPLC indicated ca. 80% conversion. The reaction mixture was cooled down, and the solid was filtered off and washed with EtOAc. The combined filtrate was washed with aq. NaHCO$_3$, dried over Na$_2$SO$_4$, filtered, concentrated on rotovap and further dried under vacuum. 1H NMR shows the ratio of desired product to unreacted 2-methyl-5-nitrobenzotrifluoride is 75:25, This material was not purified but used directly in the next step.

1-Methyl-4-(4-nitro-2-(trifluoromethyl)benzyl)piperazine: To a solution of crude 1-(bromomethyl)-4-nitro-2-(trifluoromethyl)benzene (13.33 mmol, 75% pure) in DCM (10 mL) was added Et$_3$N (1.4 mL, 10 mmol) and 1-methylpiperazine (1.1 mL, 10 mmol). Afetr stirring for 3 h at rt, aq. NaHCO$_3$ was added, and the mixture was extracted with DCM. The combined organic layer was dried over Na$_2$SO$_4$, filtered, concentrated, and the resulting residue was purified by silica gel chromatography (eluted with 10% MeOH/DCM) to provide 2.21 g of product as a pale yellow oil.

4-((4-Methylpiperazin-1-yl)methyl)-3-(trifluoromethyl) aniline: A suspension of 1-methyl-4-(4-nitro-2-(trifluoromethyl)benzyl)piperazine (1.23 g, 4 mmol) and sodium hydrosulfite (7.0 g, 85% pure from Aldrich, 40 mmol) in acetone and water (1:1, 20 mL) was refluxed for 3 h. Upon cooling, the volatile components (mainly acetone) were removed on rotavap, and the resulting mixture was subjected to filtration. The solid was thoroughly washed with EtOAc. The combined filtrate was extracted with n-BuOH (4×), and the combined organic layer was washed with saturated aq. NaHCO$_3$, dried (Na$_2$SO$_4$), filtered, concentrated, and the resulting residue was purified by silica gel chromatography (eluted with 5% MeOH/DCM, MeOH was pre-saturated with ammonia gas) to provide 0.71 g of product as a pale yellow solid.

3-Iodo-4-methyl-N-(4-((4-methylpiperazin-1-yl)methyl)-3-(trifluoromethyl)phenyl) Benzamide: 3-Iodo-4-methylbenzoyl chloride (0.48 g, 1.7 mmol), prepared from the reaction of 3-iodo-4-methylbenzoic acid and SOCl$_2$ (as previously described), was added to a solution of 4-((4-methylpiperazin-1-yl)methyl)-3-(trifluoromethyl)aniline (0.47 g, 1.7 mmol), N,N-diisopropylethylamine (0.26 g, 2.0 mmol), and a catalytic amount of DMAP in THF (10 mL). After stirring at rt for 2 h, the reaction was quenched with water. EtOAc was added and the layers separated. The combined organic layers were concentrated to dryness and purified by silica gel chromatography (eluted with 5% MeOH/DCM, MeOH was pre-saturated with ammonia gas), to provide 0.51 g of product as an off-white solid.

Alternative synthesis of 3-(Imidazo[1,2-a]pyrazin-3-ylethynyl)4-methyl-N-(4-((4-methylpiperazin-1-yl)methyl)-3-(trifluoromethyl)phenyl)benzamide: 3-(Imidazo[1,2-a]pyrazin-3-ylethynyl)-4-methyl-N-(4-((4-methylpiperazin-1-yl)methyl)-3-(trifluoromethyl) phenyl)benzamide and its mono hydrochloride salt can be prepared in an alternative synthesis similar to that described in Example 1 from 3-(imidazo[1,2-a]pyrazin-3-ylethynyl)-4-methylbenzoic acid and 4-((4-methylpiperazin-1-yl)methyl)-3-(trifluoromethyl) aniline (as prepared above).

Example 3

N-(3-(2-((dimethylamino)methyl)-1H-imidazol-1-yl)-5-(trifluoromethyl)phenyl)-3-(imidazo[1,2-a]pyrazin-3-ylethynyl)-4-methylbenzamide

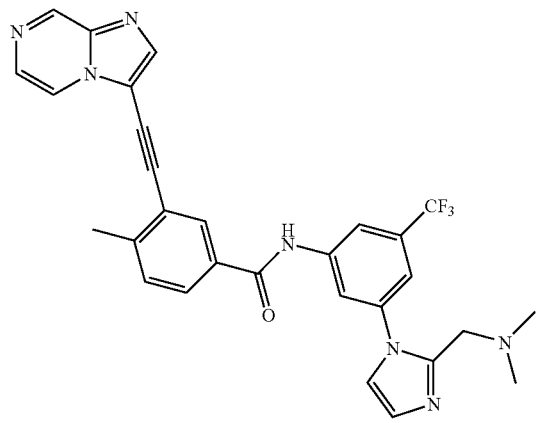

The title compound was synthesized from 3-ethynylimidazo[1,2-a]pyrazine and N-(3-(2-((dimethylamino)methyl)-1H-imidazol-1-yl)-5-(trifluoromethyl)phenyl)-3-iodo-4-methylbenzamide in a manner similar to that described for Example 1. The product was obtained as a solid: 544 m/z (M+H).

1-(1H-imidazol-2-yl)-N,N-dimethylmethanamine: To a two-necked round-bottomed flask equipped with a reflux condenser and a pressure-equalizing addition funnel, was added 2-imidazolecarboxaldehyde (6 g, 62.5 mmol) in MeOH (60 mL). To this suspension (ambient temperature) was added a solution of dimethylamine (40% aqueous, 60 mL) at a fast dropping rate (20 min). After the addition was complete, solid sodium borohydride (7 g, 186.8 mmol,) was CAUTIOUSLY added portionwise over 45 min. Foaming occurred after each portion, and the internal temperature was allowed to maintain ~50° C. without external cooling. The reaction mixture was then heated to 65° C. for 3 h and allowed to cool to ambient temperature for overnight. The reaction contents were concentrated in vacuo and the resultant residue was taken up in EtOAc (2×30 mL) washed with brine and with CHCl$_3$ (4×100 mL). The EtOAc extract was discarded. The CHCl$_3$ extract was dried over (NaSO$_4$), filtered, and concentrated in vacuo to give 3.7 g of the desired product as a waxy solid.

3-(2-((Dimethylamino)methyl)-1H-imidazol-1yl)-5-(trifluoromethyl)aniline: 3-Amino-5-bromobenzotrifluoride (6 g, 25 mmol) and 1-(1H-imidazol-2-yl)-N,N-dimethylmethanamine (3.7 g, 29.6 mmol) were dissolved in anhydrous DMSO (25 mL). To this was added CuI (0.95 g, 7.5 mmol), 8-hydroxy quinoline (0.72 g, 7.5 mmol) and K$_2$CO$_3$ (6.9 g, 50 mmol). The mixture was stirred vigorously and degassed with N$_2$ for 15 minutes. The flask was then equipped with a condenser and heated at 120° C. for 18 h. The resultant heterogeneous mixture was cooled to rt, poured into 14% aq. NH$_4$OH (100 mL) and extracted with EtOAc (3×300 ml). The combined extracts were dried over NaSO$_4$ and concentrated in vacuo. The residue was chromatograhed over silica gel eluting with MeOH/DCM (5:95) to furnish 3.5 g of the desired product as a tan colored material: 285 m/z (M+H).

N-(3-(2-((dimethylamino)methyl)-1H-imidazol-1-yl)-5-(trifluoromethyl)phenyl)-3-iodo-4-methylbenzamide: 3-Iodo-4-methylbenzoyl chloride (2.2 g, 7.88 mmol), dissolved in anhydrous THF (13 mL), was added dropwise to a solution of 3-(2-((dimethylamino)methyl)-1H-imidazol-1-yl)-5-(trifluoromethyl)aniline (1.5 g, 5.5 mmol), DIPEA (2.1 mL, 11.8 mmol) in THF (30 mL) at ~5° C. The resultant solution was stirred at ambient temperature overnight. The solvent was removed in vacuo and the crude residue was redissolved in $CH_2Cl_2$ and washed with 1 N NaOH. The organic layer was then washed with water, and brine then dried over $NaSO_4$ before being concentrated in vacuo. The brown colored residue was then triturated in a mixture of hexanes/DCM to precipitate 1.4 g of the desired product as an off-white powder: 529 m/z (M+H).

Alternative Synthesis of N-(3-(2-((dimethylamino)methyl)-1H-imidazol-1-yl)-5-(trifluoromethyl)phenyl)-3-(imidazo[1,2-a]pyrazin-3-ylethynyl)-4-methylbenzamide: N-(3-(2-((dimethylamino)methyl)-1H-imidazol-1-yl)-5-(trifluoromethyl)phenyl)-3-(imidazo[1,2-a]pyrazin-3-ylethynyl)-4-methylbenzamide and its mono hydrochloride salt can be prepared in an alternative synthesis similar to that described in Example 1 from 3-(imidazo[1,2-a]pyrazin-3-ylethynyl)-4-methylbenzoic acid and 3-(2-((Dimethylamino)methyl)-1H-imidazol-1-yl)-5-(trifluoromethyl)aniline (as prepared above).

Example 4

3-(Imidazo[1,2-a]pyridin-3-ylethynyl)-4-methyl-N-(3-(4-methyl-1H-imidazol-1-yl)-5-(trifluoromethyl)phenyl)benzamide

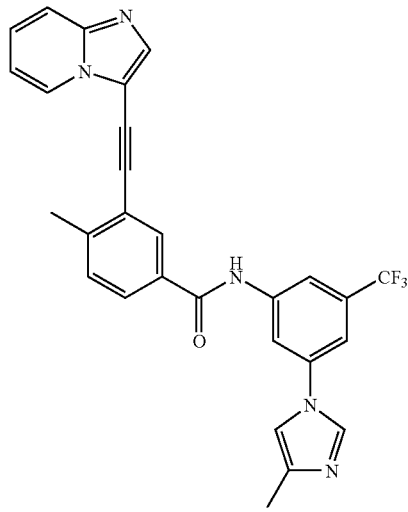

3-Ethynylimidazo[1,2-a]pyridine: To 3-bromoimidazo[1,2-a]pyridine (5 g, 0.0254 mol) in acetonitrile (50 mL) in a sealed tube was added bis(triphenylphosphine) palladium(II) dichloride (0.445 g, 0.634 mmol), CuI (0.17 g, 0.89 mmol), dicyclohexylamine (5.6 mL, 0.028 mol) and ethynyltrimethylsilane (7.2 mL, 0.051 mol). The solution was purged with argon for 15 minutes, sealed and heated at 80° C. for 3 h. At this point the HPLC did not show any starting bromide. The solvents were concentrated and to the residue was added water and dichloromethane (25 mL each). The organic layer was separated and the aqueous layer was repeatedly extracted with dichloromethane (3×20 mL). The combined extracts were dried ($Na_2SO_4$), and concentrated (Rf, 0.47 in 1/1 hexanes/ethyl acetate). The resulting residue was dissolved in THF (100 mL) and treated with tetrabutyl ammonium fluoride monohydrate (8.3 g, 0.032 mol) in water (5 mL) and the mixture was stirred at rt for 2 h. The solvents were concentrated and the resuting residue was partitioned between water (25 mL) and dichloromethane (150 mL). The aquesous layer was extracted with dichloromethane (2×30 mL). The combined extracts were dried ($Na_2SO_4$), and concentrated. The resulting residue was purified by combiflash on silica gel using hexanes/ethyl acetate. The desired product was eluted with 50/50 hexane/ethyl acetate and isolted as an off-white solid: MS (M+H)$^+$ 200.

3-(4-Methyl-1H-imidazol-1yl)-5-(trifluoromethyl) aniline: A suspension of 3-bromo-5-(trifluoromethyl)aniline (4.8 g, 20 mmol), 4-methylimidazole (1.97 g, 24 mmol), potassium carbonate (3.04 g, 22 mmol), CuI (0.57 g, 3 mmol), and 8-hydroxyquinoline (0.44 g, 3 mmol,) in dry DMSO (20 mL) in a pressure tube was degassed by bubbling $N_2$ into the suspension for 10 minutes while stirring. The tube was sealed tightly. The mixture was heated at 120° C. (oil bath temperature) for 15 h. The mixture was cooled down to 45-50° C. and 14% aq. $NH_4OH$ (20 mL) was added. The mixture was maintained at this temperature for 1 h. After cooling to rt, water and ethyl acetate were added. The aqueous layer was extracted with ethyl acetate and the combined organic layers were passed through a short silica gel column to remove most of green/blue Cu salts. The filtrate was dried over sodium sulfate and concentrated on a rotavap. The crude product was recrystallized from EtOAc/hexanes, giving pure pale yellow needles. The mother liquor was concentrated and the residue was purified on silica gel column (5% methanol/methylene chloride), yielding a second crop as pale yellow needles.

3-Iodo-4methyl-N-(3-(4-methyl-1H-imidazol-1-yl)-5-(trifluoromethyl)phenyl) Benzamide: 3-Iodo-4-methylbenzoic acid (2.62 g, 10 mmol) was refluxed in $SOCl_2$ (10 mL) for 1 h. The volatile components were removed on a rotavap and the residue was dissolved in benzene (10 mL), concentrated to dryness on a rotavap and further dried under vacuum. The resulting acyl chloride was added to a solution 3-(4-methyl-1H-imidazol-1-yl)-5-(trifluoromethyl)benzenamine (2.46 g, 10.2 mmol), N,N-diisopropylethylamine (1.56 g, 12 mmol), and a catalytic amount of DMAP in THF (20 mL). After stirring at rt for 2 h, the reaction was quenched with water. EtOAc was added and the layers separated. The combined organic layers were concentrated to dryness and used without purification in next step.

3-(Imidazo[1,2-a]pyridin-3-ylethynyl)-4-methyl-N-(3-(4-methyl-1H-imidazol-1yl)-5-(trifluoromethyl)phenyl)benzamide: To a solution of 3-iodo-4-methyl-N-(3-(4-methyl-1H-imidazol-1-yl)-5-(trifluoromethyl)phenyl)benzamide (0.11 g, 0.22 mmol.) in DMF (1 mL) in a sealed tube was added Pd[(PPh$_3$)$_4$] (0.013 g, 0.011 mmol), CuI (3 mg, 0.016 mmol), diethylisopropylamine (0.057 mL, 0.33 mmol.), followed by 3-ethynylimidazo[1,2-a]pyridine (0.040 g, 0.28 mmol.). The mixture was purged with argon for 15 minutes, sealed and stirred at rt for 28 h. The solvent was concentrated and the residue was taken up in methylene chloride (50 mL). The organic layer was washed with water, dried ($Na_2SO_4$) and evaporated to leave a brown residue which was purified by combiflash (hexane/ethyl acetate/methanol) to yield the desired material: MS (M+H)$^+$ 500.

Alternative Synthesis of 3-(Imidazo[1,2-a]pyridin-3-ylethynyl)-4-methyl-N-(3-(4-methyl-1H-imidazol-1-yl)-5-(trifluoromethyl)phenyl)benzamide: 3-(Imidazo[1,2-a]pyridin-3-ylethynyl)-4-methyl-N-(3-(4-methyl-1H-imidazol-1-yl)-5-(trifluoromethyl)phenyl)benzamide and its mono hydrochloride salt can be prepared in an alternative synthesis similar to that described in Example 1 from 3-(imidazo[1,2-a]pyridin-3-ylethynyl)-4-methylbenzoic acid and 3-(4-Methyl-1H-imidazol-1-yl)-5-(trifluoromethyl)aniline (as prepared above). The 3-(imidazo[1,2-a]pyridin-3-ylethynyl)-4-methylbenzoic acid is prepared in a manner similar to that described in Example 1 using 3-Ethynylimidazo[1,2-a]pyridine and 3-iodo-4-methylbenzoic acid as Sonogashira coupling partners.

Example 5

N-(3-(1H-imidazol-1-yl)-5-(trifluoromethyl)phenyl)-3-(imidazo[1,2-a]pyridin-3-ylethynyl)-4-methylbenzamide

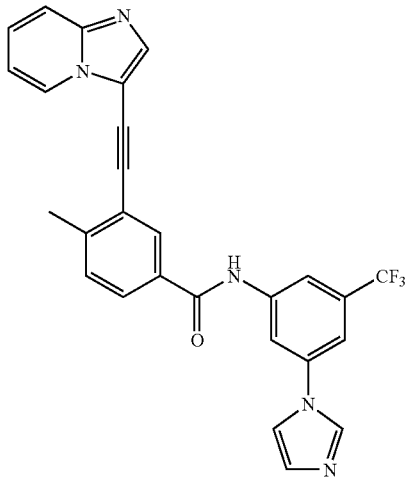

The titled compound was made as for example 1 using N-(3-(1H-imidazol-1-yl)-5-(trifluoromethyl)phenyl)-3-iodo-4-methylbenzamide and 3-ethynylimidazo[1,2-a]pyridine: MS (M+H)$^+$ 486. The titled compound can also be prepared according to the alternative synthesis described in example 1 from 3-(imidazo[1,2-a]pyridin-3-ylethynyl)-4-methylbenzoic acid and 3-(1H-imidazol-1-yl)-5-(trifluoromethyl)aniline (as prepared in Example 1). The 3-(imidazo[1,2-a]pyridin-3-ylethynyl)-4-methylbenzoic acid is prepared in a manner similar to that described in Example 1 using 3-Ethynylimidazo[1,2-a]pyridine and 3-iodo-4-methylbenzoic acid as Sonogashira coupling partners.

Example 6

3-(Imidazo[1,2-a]pyridin-3-ylethynyl)-4-methyl-N-(4-(trifluoromethyl)pyridin-2-yl)benzamide

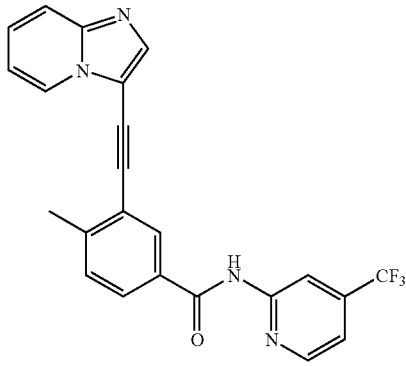

The titled compound was made as for example 1 using 3-iodo-4-methyl-N-(4-(trifluoromethyl)pyridin-2-yl)benzamide and 3-ethynylimidazo[1,2-a]pyridine: MS (M+H)$^+$ 421.39.

Example 7

N-(5-tert-butylisoxazol-3-yl)-3-(imidazo[1,2-a]pyridin-3-ylethynyl)-4-methylbenzamide

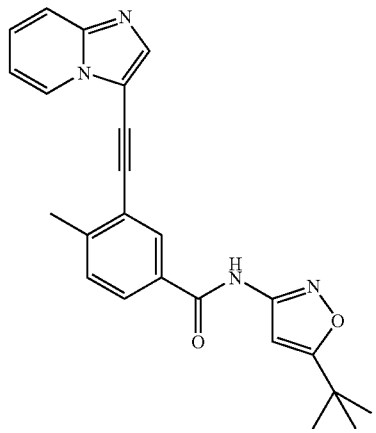

The titled compound was made as for example 1 using N-(5-tert-butylisoxazol-3-yl)-3-iodo-4-methylbenzamide and 3-ethynylimidazo[1,2-a]pyridine: MS (M+H)$^+$ 399.

Example 8

3-(Imidazo[1,2-a]pyridin-3-ylethynyl)-4-methyl-N-(4-((4-methylpiperazin-1-yl)methyl)-3-(trifluoromethyl)phenyl)benzamide

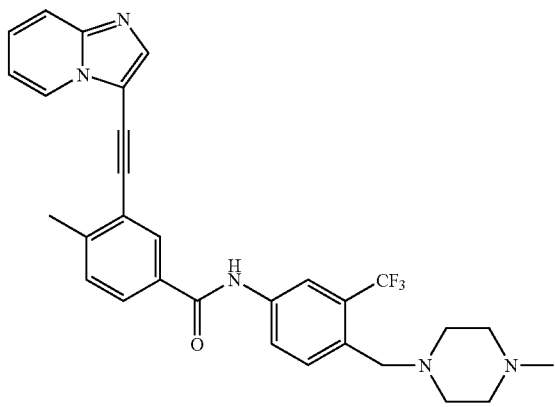

3-Ethynylimidazo[1,2-a]pyridine (37 mg, 0.26 mmol), 3-iodo-4-methyl-N-(4-((4-methylpiperazin-1-yl)methyl)-3-(trifluoromethyl)phenyl)benzamide (103.4 mg, 0.2 mmol), (prepared as in Example 2), Pd[(PPh$_3$)$_4$] (11.6 mg, 5mol %), and CuI (2.9 mg, 7.5 mmol %) was placed in a vial with rubber septum. The mixture underwent 3 cycles of vacuum/filling with N$_2$, and DMF (1.5 ml) and N,N-diisopropylethylamine (53 mL, 0.3 mmol) was added. The mixture was stirred at rt for 16 h, and the reaction was quenched with H$_2$O. EtOAc and more water were added for extraction. The combined organic layer was dried (Na$_2$SO$_4$), filtered, concentrated, and the resulting residue was purified by silica gel chromatography (eluent: 5% MeOH in methylene chloride, MeOH was presaturated with ammonia gas), giving the titled compound as an off-white solid (53%, 56 mg): MS (M+H)+ 532.

Alternative Synthesis of 3-(Imidazo[1,2-a]pyridin-3-yl-ethynyl)-4-methyl-N-(4-((4-methylpiperazin-1-yl)methyl)-3-(trifluoromethyl)phenyl)benzamide: 3-(Imidazo[1,2-a]pyridin-3-ylethynyl)-4-methyl-N-(4-((4-methylpiperazin-1-yl)methyl)-3-(trifluoromethyl) phenyl)benzamide and its mono hydrochloride salt can be prepared in an alternative synthesis similar to that described in Example 1 from 3-(imidazo[1,2-a]pyridin-3-ylethynyl)-4-methylbenzoic acid and 4-((4-methylpiperazin-1-yl)methyl)-3-(trifluoromethyl)aniline (as prepared in example 2). The 3-(imidazo[1,2-a]pyridin-3-ylethynyl)-4-methylbenzoic acid is prepared in a manner similar to that described in Example 1 using 3-Ethynylimidazo[1,2-a]pyridine and 3-iodo-4-methylbenzoic acid as Sonogashira coupling partners.

Example 9

N-(3-(2-((dimethylamino)methyl)-1H-imidazol-1-yl)-5-(trifluoromethyl)phenyl)-3-(imidazo[1,2-a]pyridin-3-ylethynyl)-4-methylbenzamide

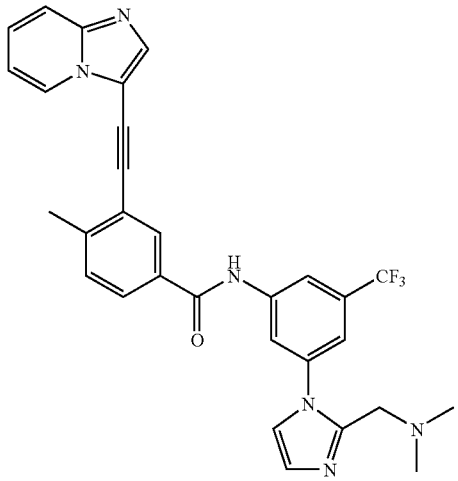

To 3-ethynylimidazo[1,2-a]pyridine (0.032 g, 0.22 mmol) in anhydrous DMF (1.26 mL) was added N-(3-(2-((dimethylamino)methyl)-1H-imidazol-1-yl)-5-(trifluoromethyl)phenyl)-3-iodo-4-methylbenzamide (prepared as in Example 3), Pd(PPh3)4 (0.013 g, 0.011 mmol), CuI (0.0032 mg, 0.0165 mmol) and DIPEA (0.064 mL, 0.44 mmol). The solution was degassed with argon for 15 minutes then stirred overnight at rt. The solvent was removed and the resultant residue was chromatographed over silica gel eluting initially with EtOAc and then with methanol/methylene chloride (5:95) to furnish the desired product: (0.07 g, 59%) MS (M+H)+ 542.

Alternative Synthesis of N-(3-(2-((dimethylamino)methyl)-1H-imidazol-1-yl)-5-(trifluoromethyl)phenyl)-3-(imidazo[1,2-a]pyridin-3-ylethynyl)-4-methylbenzamide: N-(3-(2-((dimethylamino)methyl)-1H-imidazol-1-yl)-5-(trifluoromethyl)phenyl)-3-(imidazo[1,2-a]pyridin-3-ylethynyl)-4-methylbenzamide and its mono hydrochloride salt can be prepared in an alternative synthesis similar to that described in Example 1 from 3-(imidazo[1,2-a]pyridin-3-ylethynyl)-4-methylbenzoic acid and 3-(2-((Dimethylamino)methyl)-1H-imidazol-1-yl)-5-(trifluoromethyl)aniline (as prepared in Example 3). The 3-(imidazo[1,2-a]pyridin-3-ylethynyl)-4-methylbenzoic acid is prepared in a manner similar to that described in Example 1 using 3-Ethynylimidazo[1,2-a]pyridine and 3-iodo-4-methylbenzoic acid as Sonogashira coupling partners.

Example 10

3-((8-Acetamidoimidazo[1,2-a]pyridin-3-yl)ethynyl)-4-methyl-N-(4-(trifluoromethyl)pyridin-2-yl)benzamide

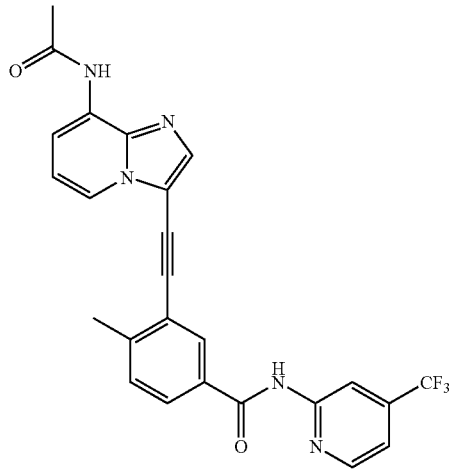

N-(3-Ethynylimidazo[1,2-a]pyridin-8-yl)acetamide: N-(3-Ethynylimidazo[1,2-a]pyridin-8-yl)acetamide was synthesized as for example 1A from N-(3-bromoimidazo[1,2-a]pyridin-8-yl)acetamide (E. Smakula Hand and William W. Paudler, J. Org. Chem., 1978, 43, 2900-2906). The titled compound was isolated as an off-white solid, Rf, 0.6 (hexane/ethylacetate 50/50): MS (M+H)+ 200.

3-((8-Acetamidoimidazo[1,2-a]pyridin-3yl) ethynyl)-4-methyl-N-(4-(trifluoromethyl)pyridin-2yl)benzamide: The titled compound was made as for example 1 using 3-iodo-4-methyl-N-(4-(trifluoromethyl)pyridin-2-yl)benzamide and N-(3-ethynylimidazo[1,2-a]pyridin-8-yl)acetamide: MS (M+H)+ 478.4.

Example 11

N-(3-(1H-imidazol-1-yl)-5-(trifluoromethyl)phenyl)-3-((8-acetamidoimidazo[1,2-a]pyridin-3-yl)ethynyl)-4-methylbenzamide

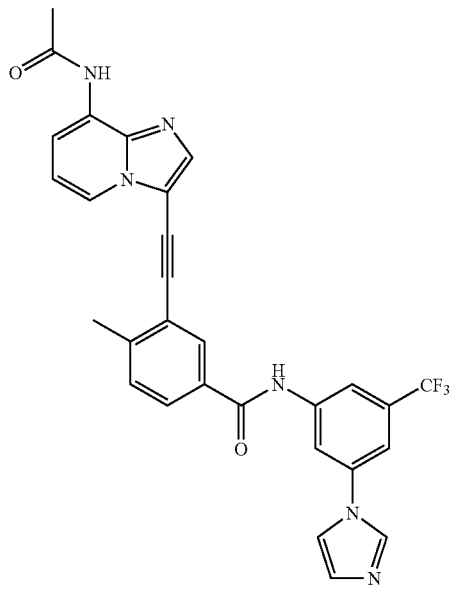

The titled compound was made as for example 10 using N-(3-(1H-imidazol-1-yl)-5-(trifluoromethyl)phenyl)-3-iodo-4-methylbenzamide and N-(3-ethynylimidazo[1,2-a]pyridin-8-yl)acetamide: MS (M+H) 543.

Example 12

4-Methyl-3-((8-(4-(methylsulfonyl)phenylamino)imidazo[1,2-a]pyridin-3-yl)ethynyl)-N-(4-(trifluoromethyl)pyridin-2-yl)benzamide

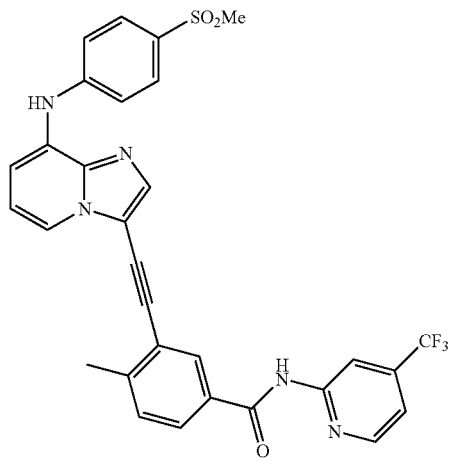

8-(Benzyloxy)-3-bromoimidazo[1,2-a]pyridine: To a solution of 2-amino-3-benzyloxypyridine (25.0 9, 124.9 mmol) and chloroacetaldehyde (50% wt in H₂O; 16.7 mL, 131.2 mmol) in 250 mL of EtOH was heated at reflux in a sealed tube for 19 h. Upon cooling to ambient temperature, the reaction mixture was concentrated and the resulting brown oil added 125 mL 1N NaOH then extracted with dichloromethane (DCM). The combined organic layers were washed with H₂O, dried over Na₂SO₄ and concentrated. Upon concentrating the solution, a tan solid formed which was filtered and dried to provide 25.8 g of crude product.

To a solution of crude 8-(benzyloxy)imidazo[1,2-a]pyridine (8.73 g, 38.9 mmol) in 100 mL of EtOH was added, dropwise, 4.8 mL (46.7 mmol) of a solution of 1:1 Br₂/H₂O at ambient temperature under an atmosphere of N₂. The resulting dark orange suspension was stirred at ambient temperature for 30 min, added 60 mL 1N NaOH, and the reaction mixture extracted with DCM. The combined organic layers were dried over Na₂SO₄ and concentrated. The crude product was purified by silica gel flash chromatography (eluted with 30% EtOAc/hexanes) to provide 7.04 g of product.

8-(Benzyloxy)-3-((trimethylsilyl)ethynyl)imidazo[1,2-a]pyridine: A mixture of 8-(benzyloxy)-3-bromoimidazo[1,2-a]pyridine (10.0 g, 33.0 mmol), 9.39 mL (66.0 mmol) of ethynyltrimethylsilane, 0.580 g (0.825 mmol) of Pd(PPh₃)₂Cl₂, 0.230 g (1.19 mmol) of CuI, and 5.09 mL (36.3 mmol) of diisopropylamine in 100 mL of acetonitrile was heated at reflux for 3 h under an atmosphere of N₂. Upon cooling to ambient temperature, the reaction mixture was concentrated and the crude product was purified by silica gel flash chromatography (eluted with 20-50% EtOAc/hexanes) to provide 6.74 g of product: 321 m/z (M+H).

3-((Trimethylsilyl)ethynyl)imidazo[1,2-a]pyridin-8yltrifluoromethanesulfonate: To a cooled (0° C.) solution of 8-(benzyloxy)-3-((trimethylsilyl)ethynyl)imidazo[1,2-a]pyridine (3.44 g, 10.7 mmol) in 400 mL of DCM, under an atmosphere of N₂, was added via cannulation 100 mL (100 mmol) of boron trichloride (1.0M solution in hexanes). The reaction solution was stirred at 0° C./N₂ for 30 min, to which was added (0° C.) 200 mL H₂O followed by extraction with DCM. The combined organic layers were washed with brine, dried over Na₂SO₄ and concentrated. The crude product was purified by silica gel flash chromatography (eluted with 30% EtOAc/hexanes then 10% MeOH/DCM) to provide 2.32 g of deprotected product: 231 m/z (M+H).

To a cooled (-78° C.) solution of 8-(hydroxy)-3-((trimethylsilyl)ethynyl)imidazo[1,2-a]pyridine (2.32 g, 10.1 mmol) and 1.63 mL (20.1 mmol) of pyridine in 50 mL of DCM, under an atmosphere of N₂, was added 2.03 mL (12.1 mmol) of trifluoromethanesulfonic anhydride via syringe. Upon removing the cooling bath, the reaction solution was stirred at ambient temperature (N₂) for 2 h. The reaction mixture was poured into a stirring solution of 100 mL 1.0N HCl, the layers separated, and the organic layer washed successively with 1.0N HCl, H₂O, saturated aqueous NaHCO₃, and brine. The organic layer was dried over Na₂SO₄ and concentrated. The crude product was filtered through a small plug of silica gel (eluted with 30% EtOAc/hexanes), concentrated, and further dried in vacuo to provide 3.63 g of product: 363 m/z (M+H).

N-(4(Methylsulfonyl)phenyl)-3-((trimethylsiyl)ethynyl)imidazo[1,2-a]pyridin-8-amine: A mixture of 3-((trimethylsilyl)ethynyl)imidazo[1,2-a]pyridin-8-yl trifluoromethanesulfonate (0.329 g, 0.91 mmol), 0.186 (1.09 mmol) of 4-(methylsulfonyl)aniline, 0.083 g (0.091 mmol) of Pd₂(dba)₂, 0.087 g (0.181 mmol) of 2-dicyclohexylphosphino-2',4',6'-triisopropylbiphenyl, and 0.385 g (1.81 mmol) of potassium phosphate in 8 mL of DME was heated at 80° C. in a sealed tube overnight under an atmosphere of N₂. Upon cooling to ambient temperature, the reaction mixture was concentrated and the crude product was purified by silica gel flash chromatography (triethylamine-treated silica gel; eluted with 0-80% EtOAc/hexanes) to provide 0.058 g of product: 384 m/z (M+H).

3-Ethynyl-N-(4-(methylsulfonyl)phenyl)imidazo[1,2-a]pyridin-8-amine: To a solution of N-(4-(methylsulfonyl)phenyl)-3-((trimethylsilyl)ethynyl)imidazo[1,2-a]pyridin-8-amine (0.058 g, 0.15 mmol) in 1.5 mL of THF was added 0.23 mL (0.23 mmol) of tetrabutylammonium fluoride (1.0M in THF) at ambient temperature. The solution was stirred for 15 min, concentrated, and the crude product purified by silica gel flash chromatography (triethylamine-treated silica gel; eluted with 100% DCM then 5% MeOH/DCM) to provide a quantitative yield (0.047 g) of product: 312 m/z (M+H).

4-Methyl-3-((8-(4-(methylsulfonyl)phenylamino)imidazo[1,2-a]pyridin-3-yl)ethynyl)-N-(4-(trifluoromethyl)pyridin-2-yl)benzamide: A mixture of 3-ethynyl-N-(4-(methylsulfonyl) phenyl)imidazo[1,2-a]pyridin-8-amine 5 (0.048 g, 0.154 mmol), 0.069 g (0.170 mmol) of 3-iodo-4-methyl-N-(4-(trifluoromethyl)pyridin-2-yl)benzamide, 0.009 g (0.008 mmol) of Pd(PPh₃)₄, 0.002 g (0.012 mmol) of CuI, and 0.04 mL (0.23 mmol) of diisopropylethylamine in 0.8 mL of DMF was stirred at ambient temperature overnight under an atmosphere of N₂. The reaction mixture was concentrated and the crude product was purified by silica gel flash chromatography (triethylamine-treated silica gel; eluted with 10% EtOAc/hexanes to 100% EtOAc) to provide 0.047 g of product as a solid: 590 m/z (M+H).

Example 13

4-methyl-3-((8-(4-sulfamoylphenylamino)imidazo[1,2-a]pyridin-3-yl)ethynyl)-N-(4-(trifluoromethyl)pyridin-2-yl)benzamide

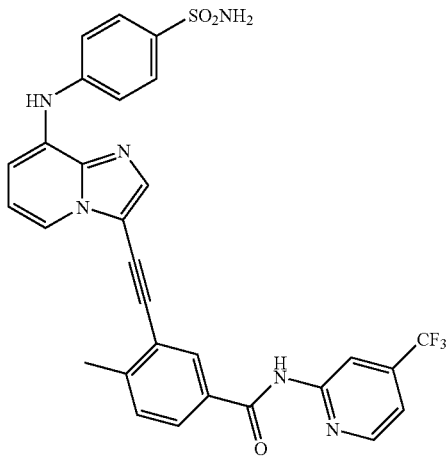

The title compound was synthesized from 3-ethynyl-N-(4-sulfamoylphenyl)imidazo[1,2-a]pyridin-8-amine and 3-iodo-4-methyl-N-(4-(trifluoromethyl)pyridin-2-yl)benzamide in a manner similar to that described for Example 12. The product was obtained as a solid: 591 m/z (M+H).

Example 14

(R)-N-(4-((3-(Dimethylamino)pyrrolidin-1-yl)methyl)-3-(trifluoromethyl)phenyl)-3-(imidazo[1,2-b]pyridazin-3-ylethynyl)4-methylbenzamide

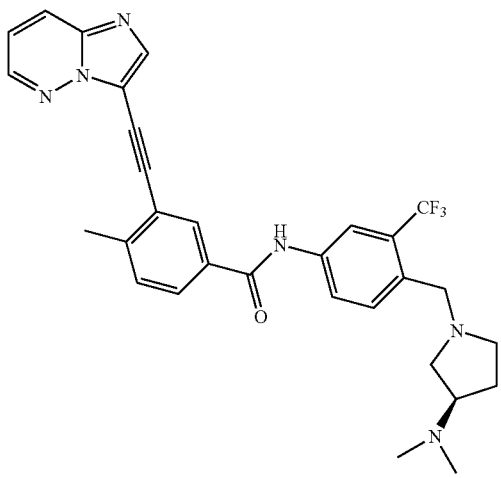

3-((Trimethylsilyl)ethynyl)imidazo[1,2-b]pyridazine: A mixture of 3-bromoimidazo[1,2-b]pyridazine (36.78 g, 0.186 mol; prepared according to Stanovnik, B. et al. *Synthesis* (1981), 12, 987-989), ethynyltrimethylsilane (21.89 g, 0.223 mol), Pd(PPh$_3$)$_4$ (10.73 g, 9.29 mmol), CuI (5.30 g, 0.028 mol), and diisopropylethylamine (32.4 mL, 0.279 mol) in 150 mL of DMF was stirred at ambient temperature, under an atmosphere of N$_2$, for 1 h. The reaction mixture was concentrated and the crude product was purified by silica gel flash chromatography (eluted with 0-5% MeOH/DCM) to provide 28.46 g of product.

3-Ethynylimidazo[1,2-b]pyridazine: To a solution of 3-((trimethylsilyl)ethynyl) imidazo[1,2-b]pyridazine (28.46 g, 0.132 mol) in 200 mL of THF was added 145 mL (0.145 mol) of tetrabutylammonium fluoride (1.0M in THF) at ambient temperature. The solution was stirred for 15 min, concentrated, and the crude product purified by silica gel flash chromatography (eluted with 0-5% MeOH/DCM) to provide 17.84 g of product.

1-(Bromomethyl)-4-nitro-2-(trifluoromethyl)benzene: A suspension of 2-methyl-5-nitrobenzotrifluoride (3.90 g, 19 mmol), N-bromosuccinimide (NBS, 3.56 g, 20 mmol), and 2,2'-azobis(2-methylpropionitrile) (AIBN, 0.094 g, 0.6 mmol) in 40 mL of CCl$_4$ was heated at reflux under N$_2$ for 16 h. HPLC indicated ca. 50% conversion. Additional NBS (10 mmol) and AIBN (0.6 mmol) were added and the mixture was heated at reflux for another 14 h. HPLC indicated ca. 80% conversion. The reaction mixture was cooled to ambient temperature, and the solid was filtered and washed with EtOAc. The combined filtrate was washed with aq. NaHCO$_3$, dried over Na$_2$SO$_4$, filtered, concentrated on rotovap, and further dried under vacuum. $^1$H NMR indicated the ratio of desired product to unreacted 2-methyl-5-nitrobenzotrifluoride to be 75:25. This material was used directly in the next step.

(R)-N,N-Dimethyl-1-(4-nitro-2-(trifluoromethyl)benzyl)pyrrolidin-3-amine: To a solution of crude 1-(bromomethyl)-4-nitro-2-(trifluoromethyl)benzene (17.5 mmol, 75% pure) in 40 mL of DCM was added Et$_3$N (2.69 mL, 19.3 mmol) and (R)-(+)-3-(dimethylamino)pyrrolidine (2.0 g, 17.5 mmol). After stirring overnight at ambient temperature under an atmosphere of N$_2$, the reaction solution was concentrated, added aq. NaHCO$_3$ (100 mL), and the resulting mixture extracted with DCM (4×50 mL). The combined organic layer was dried over Na$_2$SO$_4$, filtered, concentrated, and the resulting residue was purified by silica gel chromatography (eluted with 0-10% MeOH/DCM) to provide 3.35 g of product as a yellow oil.

(R)-1-(4-Amino-2-(trifluoromethy)benzyl)-N,N-dimethylpyrrolidin-3-amine: To a solution of (R)-N,N-dimethyl-1-(4-nitro-2-(trifluoromethyl)benzyl)pyrrolidin-3-amine (1.20 g, 3.79 mmol) in 20 mL of wet EtOH was added 0.26 g of Pd/C (10% Pd on C) and the mixture shaken in a Parr apparatus (pressure reaction vessel purged thoroughly with H$_2$ and pressure regulated at 45 psi throughout) for 2-3 h. The reaction mixture was filtered through a small pad of celite, washed with EtOAc, and the combined organics concentrated to provide a quantitative yield of a light yellow oil. This material was used directly in the next step.

(R)-N-(4-((3-(Dimethylamino)pyrrolidin-1-yl)methyl)-3-(trifluoromethyl)phenyl)-3-iodo-4-methylbenzamide: To a cooled (0° C.) solution of (R)-1-(4-amino-2-(trifluoromethyl)benzyl)-N,N-dimethylpyrrolidin-3-amine (3.79 mmol) in 14 mL DCM, under an atmosphere of N$_2$, was added 3-Iodo-4-methylbenzoyl chloride (1.17 g, 4.17 mmol; CAS#52107-98-9, prepared from the reaction of 3-iodo-4-methylbenzoic acid and SOCl$_2$) followed by dropwise addition of N,N-diisopropylethylamine (2.64 mL, 15.2 mmol). After stirring to ambient temperature over 1.5 h, the reaction mixture was concentrated and the crude product was purified by silica gel chromatography (eluted with 0-8% MeOH/

DCM; MeOH was pre-saturated with ammonia gas), to provide 0.71 g of product as a thick yellow oil.

(R)-N-(4-((3-(dimethylamino)pyrrolidin-1-yl)methyl)-3-(trifluoromethyl)phenyl)-3-(imidazo[1,2-b]pyridazin-3yl-ethynyl)-4-methylbenzamide: A mixture of 3-ethynylimidazo[1,2-b]pyridazine (0.051 g, 0.34 mmol), 0.150 g (0.28 mmol) of (R)-N-(4-((3-(dimethylamino)pyrrolidin-1-yl)methyl)-3-(trifluoromethyl)phenyl)-3-iodo-4-methylbenzamide, 0.016 g (0.014 mmol) of Pd(PPh$_3$)$_4$, 0.004 g (0.021 mmol) of CuI, and 0.09 mL (0.51 mmol) of N,N-diisopropylethylamine in 3.5 mL of DMF was stirred at ambient temperature, under an atmosphere of N$_2$, for 3 days (reaction pushed to completion with additional equivalents of reagents and heating to 80° C). The reaction mixture was concentrated and the crude product was purified by silica gel chromatography (eluted with 0-10% MeOH/DCM; MeOH was pre-saturated with ammonia gas) to provide 0.020 g of product as a solid: 547 m/z (M+H).

Alternative Synthesis of (R)-N-(4-((3-(Dimethylamino)pyrrolidin-1-yl)methyl)-3-(trifluoromethyl)phenyl)-3-(imidazo[1,2-b]pyridazin-3-ylethynyl)-4-methylbenzamide: (R)-N-(4-((3-(Dimethylamino)pyrrolidin-1-yl)methyl)-3-(trifluoromethyl)phenyl)-3-(imidazo[1,2-b]pyridazin-3-ylethynyl)-4-methylbenzamide and its mono hydrochloride salt can be prepared in an alternative synthesis similar to that described in Example 1 from 3-(imidazo[1,2-b]pyridazin-3-ylethynyl)-4-methylbenzoic acid and (R)-1-(4-Amino-2-(trifluoromethyl)benzyl)-N,N-dimethylpyrrolidin-3-amine (as prepared above). The 3-(imidazo[1,2-b]pyridazin-3-ylethynyl)-4-methylbenzoic acid is prepared in a manner similar to that described in Example 1 using 3-Ethynylimidazo[1,2-b]pyridazine and 3-iodo-4-methylbenzoic acid as Sonogashira coupling partners.

Example 15

N-(3-(Imidazo[1,2-b]pyridazin-3-ylethynyl)-4-methylphenyl)-4-((4-methylpiperazin-1-yl)methyl)-3-(trifluoromethyl)benzamide

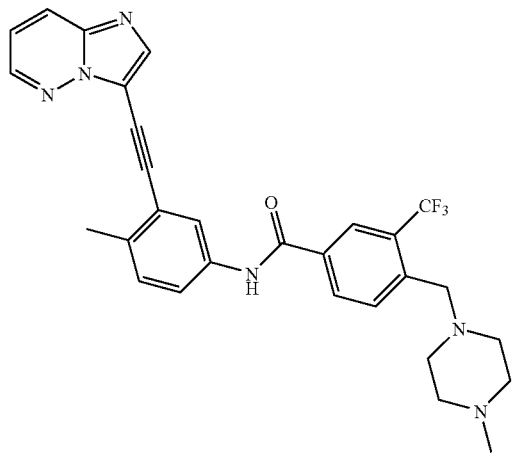

The title compound was synthesized from 3-ethynylimidazo[1,2-b]pyridazine and N-(3-iodo-4-methylphenyl)-4-((4-methylpiperazin-1-yl)methyl)-3-(trifluoromethyl)benzamide in a manner similar to that described for Example 14. The product was obtained as a solid: 533 m/z (M+H).

N-(3-Iodo-4-methylphenyl)-4-((4methylpiperazin-1-yl)methyl)-3-(trifluoromethyl)benzamide: To a flask containing 1.0 g (2.67 mmol) of 4-[(4-methyl-1-piperazinyl)methyl]-3-(trifluoromethyl)-benzoic acid (CAS# 859027-02-4; prepared according to Asaki, T. et al. Bioorg. Med. Chem. Lett. (2006), 16, 1421-1425), 0.62 g (2.67 mmol) of 3-Iodo-4-methylaniline, 0.77 g (4.0 mmol) of N-(3-dimethylaminopropyl)-N'-ethylcarbodiimide hydrochloride (EDAC), and 0.43 g (3.2 mmol) of N-hydroxybenzotriazole monohydrate (HOBt H$_2$O) was added 5 mL of DCM and 5 mL of triethylamine. The solution was stirred at ambient temperature under an atmosphere of N$_2$ for 3 days, concentrated, and the crude product purified by silica gel chromatography (eluted with 100% EtOAc then 10% MeOH/EtOAc), to provide 0.69 g of product as a white solid.

Example 16

3-(Imidazo[1,2-b]pyridazin-3-ylethynyl)-4-methyl-N-(4-((4-methylpiperazin-1-yl)-methy-3-(trifluoromethyl)phenyl)benzamide

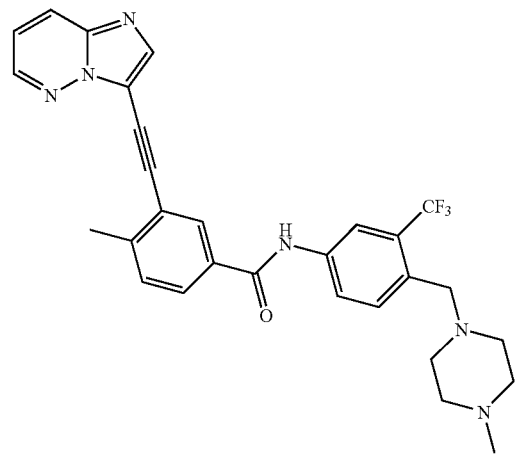

The title compound was synthesized in a manner similar to that described for Example 14, from 3-ethynylimidazo[1,2-b]pyridazine and 3-iodo-4-methyl-N-(4-((4-methylpiperazin-1-yl)methyl)-3-(trifluoromethyl)phenyl)benzamide (Prepared as described in Example 2). The product was obtained as a solid: 533 m/z (M+H).

Alternative Synthesis of 3-(Imidazo[1,2-b]pyridazin-3-ylethynyl)-4-methyl-N-(4-((4-methylpiperazin-1-yl)methyl)-3-(trifluoromethyl)phenyl)benzamide: 3-(Imidazo[1,2-b]pyridazin-3-ylethynyl)-4-methyl-N-(4-((4-methylpiperazin-1-yl)methyl)-3-(trifluoromethyl)phenyl)benzamide and its mono hydrochloride salt can be prepared in an alternative synthesis similar to that described in Example 1 from 3-(imidazo[1,2-b]pyridazin-3-ylethynyl)-4-methylbenzoic acid and 4-((4-methylpiperazin-1-yl)methyl)-3-(trifluoromethyl)aniline (as prepared in example 2). The 3-(imidazo[1,2-b]pyridazin-3-ylethynyl)-4-methylbenzoic acid is prepared in a manner similar to that described in Example 1 using 3-Ethynylimidazo[1,2-b]pyridazine and 3-iodo-4-methylbenzoic acid as Sonogashira coupling partners.

Example 17

N-(3-Chloro-4-((4-methylpiperazin-1-yl)methyl)phenyl)-3-(imidazo[1,2-b]pyridazin-3-ylethynyl)-4-methylbenzamide

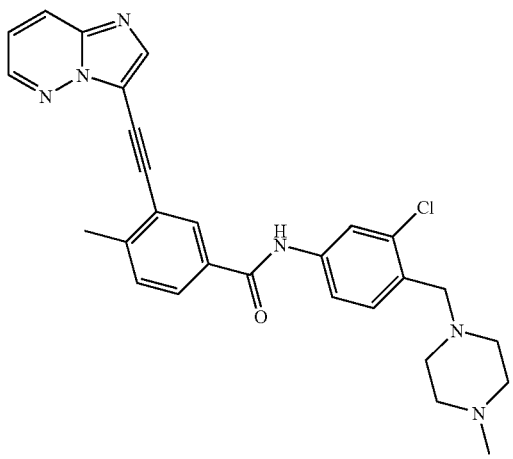

The title compound was synthesized according to Example 14, from 3-ethynylimidazo[1,2-b]pyridazine and N-(3-chloro-4-((4-methylpiperazin-1-yl)methyl)phenyl)-3-iodo-4-methylbenzamide. The product was obtained as a solid: 499 m/z (M+H).

1-(Bromomethyl)-2-chloro-4-nitro-benzene: A suspension of 2-chloro-4-nitrotoluene (10.0 g, 58.3 mmol), N-bromosuccinimide (NBS, 10.9 g, 61.2 mmol), and 2,2'-azobis(2-methylpropionitrile) (AIBN, 0.29 9, 1.75 mmol) in 120 mL of $CCl_4$ was heated at reflux under an atmosphere of $N_2$ for 12 h. The reaction mixture was cooled to ambient temperature, and the solid was filtered and washed with EtOAc. The combined filtrate was washed with aq. $NaHCO_3$, dried over $Na_2SO_4$, filtered, concentrated on rotovap, and further dried under vacuum. $^1H$ NMR indicated the ratio of desired product to unreacted 2-chloro-4-nitrotoluene to be 50:50, This material was used directly in the next step.

1-(2-Chloro-4-nitrobenzyl)-4-methylpiperazine: To a solution of crude 1-(bromomethyl)-2-chloro4-nitro-benzene (29.1 mmol; 50% pure) in 30 mL of DCM was added $Et_3N$ (4.2 mL, 30 mmol) and 1-methylpiperazine (3.4 mL, 30 mmol). After stirring for 3 h at ambient temperature, aq. $NaHCO_3$ was added and the mixture was extracted with DCM. The combined organic layer was dried over $Na_2SO_4$, filtered, concentrated, and the resulting residue was purified by silica gel chromatography (eluted with 5% MeOH/DCM) to provide 6.80 g of product as a dark yellow oil.

3-Chloro-4-((4-methylpiperazin-1-yl)methyl)aniline: To a solution of 1-(2-chloro-4-nitrobenzyl)-4-methylpiperazine (0.96 g, 3.6 mmol) in MeOH/water (4:1, 50 mL) was added 1.80 g (33.7 mmol) of $NH_4Cl$ and 1.47 g (26.3 mmol) of Fe dust and the mixture heated at reflux under an atmosphere of $N_2$ for 2 h (HPLC indicated no progress). To this was added 4 mL of glacial acetic acid and the mixture heated at reflux for an additional 2 h. The reaction mixture was cooled to ambient temperature, filtered, and the filtrate concentrated. The residue was partitioned between EtOAc and saturated aq. $NaHCO_3$, the separated aqueous layer was extracted with EtOAc, and the combined organics washed with brine and dried over $Na_2SO_4$. Upon concentration, the crude product was purified by silica gel chromatography (eluted with 5-7% MeOH/DCM; silica gel deactivated with 1% triethylamine/DCM) to provide 0.53 g of product.

Alternative Synthesis of N-(3-Chloro-4-((4-methylpiperazin-1-yl)methyl)phenyl)-3-(imidazo[1,2-b]pyridazin-3-ylethynyl)-4-methylbenzamide: N-(3-Chloro-4-((4-methylpiperazin-1-yl)methyl)phenyl)-3-(imidazo[1,2-b]pyridazin-3-ylethynyl)-4-methylbenzamide and its mono hydrochloride salt can be prepared in an alternative synthesis similar to that described in Example 1 from 3-(imidazo[1,2-b]pyridazin-3-ylethynyl)-4-methylbenzoic acid and 3-Chloro-4-((4-methylpiperazin-1-yl)methyl)aniline (as prepared above). The 3-(imidazo[1,2-b]pyridazin-3-ylethynyl)-4-methylbenzoic acid is prepared in a manner similar to that described in Example 1 using 3-Ethynylimidazo[1,2-b]pyridazine and 3-iodo-4-methylbenzoic acid as Sonogashira coupling partners.

Example 18

N-(3-Cyclopropyl-4-((4-methylpiperazin-1-yl)methyl)phenyl)-3-(imidazo[1,2-b]pyridazin-3-ylethynyl)-4-methylbenzamide

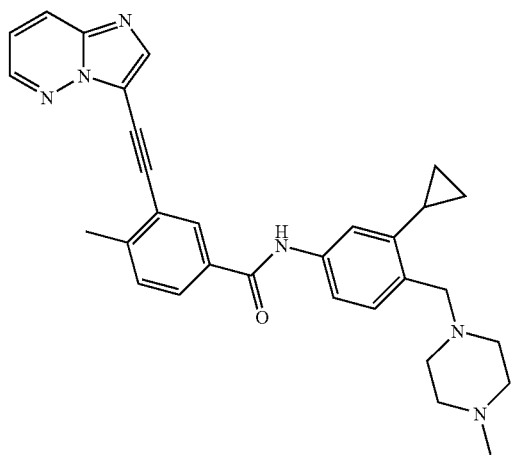

The title compound was synthesized from 3-ethynylimidazo[1,2-b]pyridazine and N-(3-cyclopropyl-4-((4-methylpiperazin-1-yl)methyl)phenyl)-3-iodo-4-methylbenzamide in a manner similar to that described for Example 14 (nitro reduction performed in a manner similar to that described for Example 17; 0.25M in MeOH/10%AcOH). The product was obtained as a solid: 505 m/z (M+H).

1-(2-Cyclopropyl-4-nitrobenzyl)-4-methylpiperazine: A mixture of 1-(2-bromo-4-nitrobenzyl)-4-methylpiperazine (0.94 g, 3.0 mmol), 0.77 g (9.0 mmol) of cyclopropylboronic acid, 0.067 g (0.30 mmol) of $Pd(OAc)_2$, 2.87 g (13.5 mmol) of $K_3PO_4$, and 0.168 g (0.60 mmol) of tricyclohexylphosphine in 18 mL of toluene/water (5:1) was heated at reflux under an atmosphere of $N_2$ for 19 h. The reaction mixture was concentrated and the crude product was purified by silica gel chromatography (eluted with 5% MeOH/DCM; MeOH was presaturated with ammonia gas) to provide 0.80 g of product.

Example 19

3-(Imidazo[1,2-b]pyridazin-3-ylethynyl)-N-(4-((4-methylpiperazin-1-yl)methyl)-3-(trifluoromethyl)phenyl)benzamide

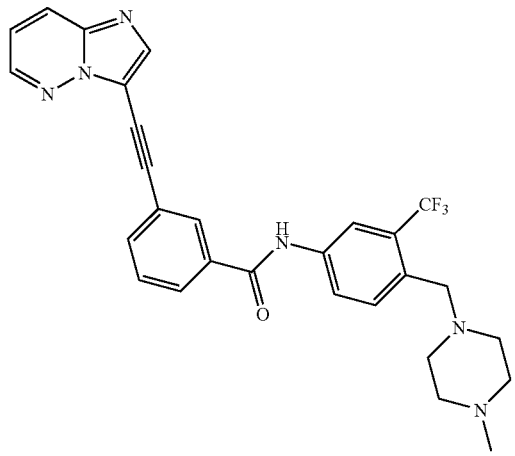

The title compound was synthesized from 3-ethynylimidazo[1,2-b]pyridazine and 3-iodo-N-(4-((4-methylpiperazin-1-yl)methyl)-3-(trifluoromethyl)phenyl)benzamide in a manner similar to that described for Example 14, The product was obtained as a solid: 519 m/z (M+H).

The titled compound can also be prepared according to the alternative synthesis described in example 1 from 3-(imidazo[1,2-b]pyridazin-3-ylethynyl)-4-methylbenzoic acid and 4-((4-methylpiperazin-1-yl)methyl)-3-(trifluoromethyl)aniline (as prepared in example 2). The 3-(imidazo[1,2-b]pyridazin-3-ylethynyl)-4-methylbenzoic acid is prepared in a manner similar to that described in Example 1 using 3-Ethynylimidazo[1,2-b]pyridazine and 3-iodo-4-methylbenzoic acid as Sonogashira coupling partners.

Example 20

N-(4-((4-(2-Hydroxyethyl)piperazin-1-yl)methyl)-3-(trifluoromethyl)phenyl)-3-(imidazo[1,2-b]pyridazin-3-ylethynyl)-4-methylbenzamide

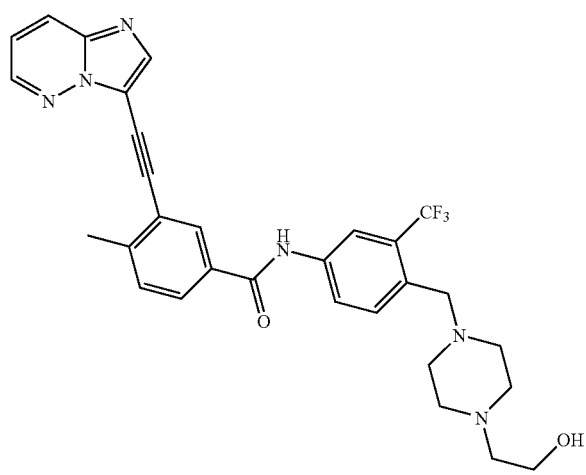

The title compound was synthesized from 3-ethynylimidazo[1,2-b]pyridazine and N-(4-((4-(2-hydroxyethyl)piperazin-1-yl)methyl)-3-(trifluoromethyl)phenyl)-3-iodo-4-methylbenzamide in a manner similar to that described for Example 14, The product was obtained as a solid: 563 m/z (M+H).

Example 21

3-(Imidazo[1,2-b]pyridazin-3-ylethynyl)-4-methyl-N-(4-(piperazin-1-ylmethyl)-3-(trifluoromethyl)phenyl)benzamide

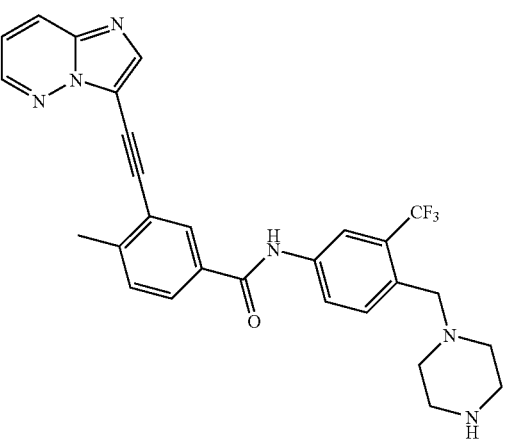

The title compound was synthesized from 3-ethynylimidazo[1,2-b]pyridazine and tert-butyl4-(4-(3-iodo-4-methylbenzamido)-2-(trifluoromethyl)benzyl)piperazine-1-carboxylate in a manner similar to that described for Example 14. Following deprotection using saturated MeOH/HCl (g), the product was obtained as a tris HCl salt: 519 m/z (M+H).

Example 22

Biological Evaluation of Compounds

Compounds of this invention are evaluated in a variety of assays to determine their biological activities. For example, the compounds of the invention can be tested for their ability to inhibit various protein kinases of interest. Some of the compounds tested displayed potent nanomolar activity against the following kinases: Abl, Abl T315I, Src and FGFR. Furthermore, several of these compounds were screened for antiproliferative activity in BaF3 cells transfected with either wild-type Bcr-Abl or the Bcr-Abl T315I mutant and demonstrated activity in the range of 1-100 nM.

The compounds can also be evaluated for their cytotoxic or growth inhibitory effects on tumor cells of interest, e.g., as described in more detail below and as shown above for some representative compounds. See e.g., WO 03/000188, pages 115-136, the full contents of which are incorporated herein by reference.

Some representative compounds are depicted below.

| Compounds of the Invention | T315I cell proliferation (nM) |
|---|---|
| (imidazo[1,2-a]pyrazin-3-yl)-ethynyl-4-methylphenyl-C(O)NH-(3-CF3-4-(piperazin-1-ylmethyl)phenyl) | <1000 |
| 8-(ureido)-imidazo[1,2-a]pyridin-3-yl-ethynyl-4-methylphenyl-C(O)NH-(4-CF3-pyridin-2-yl) | <1000 |
| (imidazo[1,2-a]pyrazin-3-yl)-ethynyl-4-fluorophenyl-C(O)NH-(3-CF3-4-((4-methylpiperazin-1-yl)methyl)phenyl) | <1000 |

| Compounds of the Invention | T315I cell proliferation (nM) |
|---|---|
| (structure: imidazo[1,2-a]pyrazine-alkyne-tolyl-C(O)NH-phenyl(CF3)-CH2-N-piperazine-ethyl) | <1000 |
| (structure: imidazo[1,2-b]pyridazine-alkyne-tolyl-C(O)NH-phenyl(CF3)-CH2-N-piperazine-CH2CH2OH) | <1000 |
| (structure: imidazo[1,2-a]pyridine-alkyne-tolyl-C(O)NH-phenyl(CF3)-CH2-N-methylpiperazine) | <1000 |

-continued

| Compounds of the Invention | T315I cell proliferation (nM) |
|---|---|
| (structure: 8-(ureido)imidazo[1,2-a]pyridine-3-yl alkyne linked to 4-methylbenzamide N-(5-tert-butylisoxazol-3-yl)) | <1000 |
| (structure: imidazo[1,2-a]pyridine-3-yl alkyne linked to 4-methylbenzamide N-[4-((4-(2-hydroxyethyl)piperazin-1-yl)methyl)-3-(trifluoromethyl)phenyl]) | <1000 |
| (structure: imidazo[1,2-a]pyridine-3-yl alkyne linked to 4-chlorobenzamide N-[4-((4-methylpiperazin-1-yl)methyl)-3-(trifluoromethyl)phenyl]) | <1000 |

-continued

| Compounds of the Invention | T315I cell proliferation (nM) |
|---|---|
| (structure) | <1000 |
| (structure) | <1000 |
| (structure) | <1000 |

| Compounds of the Invention | T315I cell proliferation (nM) |
|---|---|
| | <1000 |
| | <1000 |
| | <1000 |
| | <1000 |

| Compounds of the Invention | T315I cell proliferation (nM) |
|---|---|
| 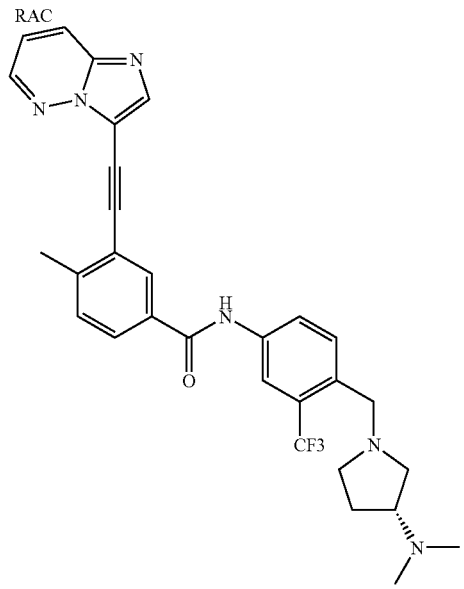 | <1000 |
| 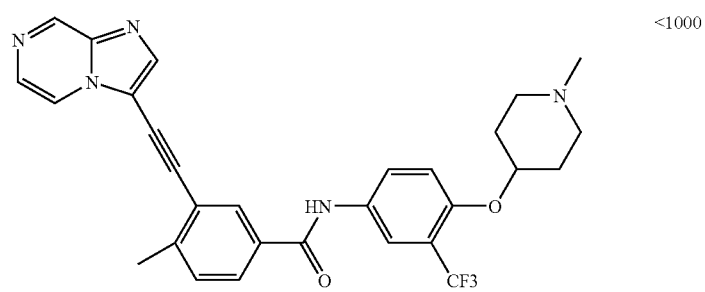 | <1000 |
| 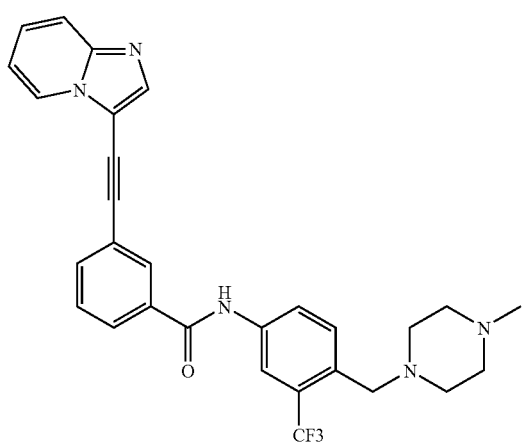 | <1000 |

-continued

| Compounds of the Invention | T315I cell proliferation (nM) |
|---|---|
| (structure) | <1000 |
| (structure) | <1000 |
| (structure) | <1000 |

-continued

| Compounds of the Invention | T315I cell proliferation (nM) |
|---|---|
| (structure) | <1000 |
| (structure) | <1000 |
| (structure) | <1000 |

-continued

| Compounds of the Invention | T315I cell proliferation (nM) |
|---|---|
| (structure) | <1000 |
| (structure) | <1000 |
| (structure) | <1000 |

-continued

| Compounds of the Invention | T315I cell proliferation (nM) |
|---|---|
| (structure) | <1000 |
| (structure) | <1000 |
| (structure) | <1000 |
| (structure) | <1000 |

-continued

| Compounds of the Invention | T315I cell proliferation (nM) |
|---|---|
| (structure) | <1000 |
| (structure) | <1000 |
| (structure) | <1000 |

-continued

| Compounds of the Invention | T315I cell proliferation (nM) |
|---|---|
| [structure] | <1000 |
| [structure] | <1000 |
| [structure] | <1000 |

| Compounds of the Invention | T315I cell proliferation (nM) |
|---|---|
| *(imidazo[1,2-a]pyridin-8-amine-3-yl ethynyl-4-methylphenyl carboxamide with N-(4-trifluoromethylpyridin-2-yl))* | <1000 |
| *(imidazo[1,2-a]pyrazin-3-yl ethynyl-4-methylphenyl carboxamide with N-(3-morpholinomethyl-5-trifluoromethylphenyl))* | <1000 |
| *(imidazo[1,2-a]pyrazin-3-yl ethynyl-4-methylphenyl carboxamide with N-(3-morpholinomethyl-5-trifluoromethylphenyl))* | <1000 |
| *(imidazo[1,2-a]pyrazin-3-yl ethynyl-4-methylphenyl carboxamide with N-(4-(imidazol-1-ylmethyl)-3-trifluoromethylphenyl))* | <1000 |

| Compounds of the Invention | T315I cell proliferation (nM) |
|---|---|
| 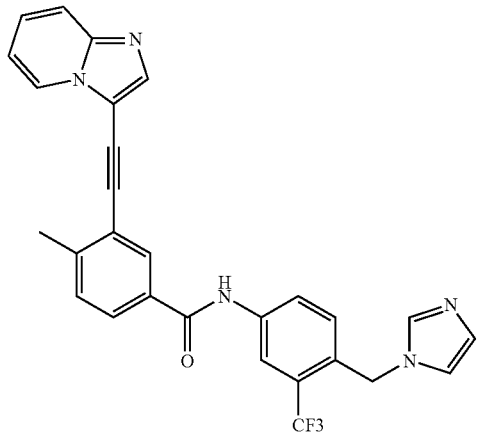 | <1000 |
| 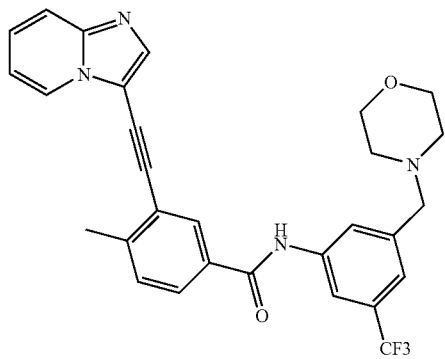 | <1000 |
| 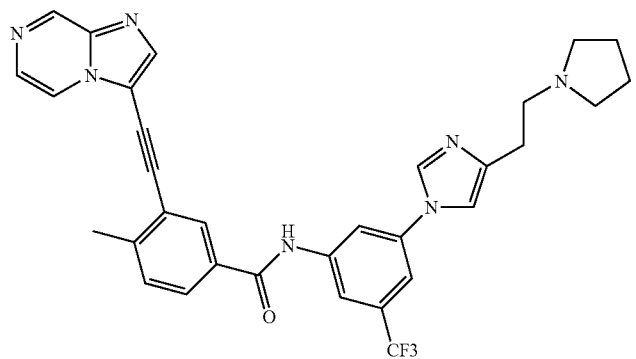 | <1000 |

-continued

| Compounds of the Invention | T315I cell proliferation (nM) |
|---|---|
| | <1000 |
| | <1000 |
| | <1000 |
| | <1000 |

-continued

| Compounds of the Invention | T315I cell proliferation (nM) |
|---|---|
| (structure) | <1000 |
| (structure) | <1000 |
| (structure) | <1000 |

| Compounds of the Invention | T315I cell proliferation (nM) |
|---|---|
| (structure) | <1000 |
| (structure) | <1000 |
| (structure) | <1000 |

-continued
| Compounds of the Invention | T315I cell proliferation (nM) |
|---|---|
| 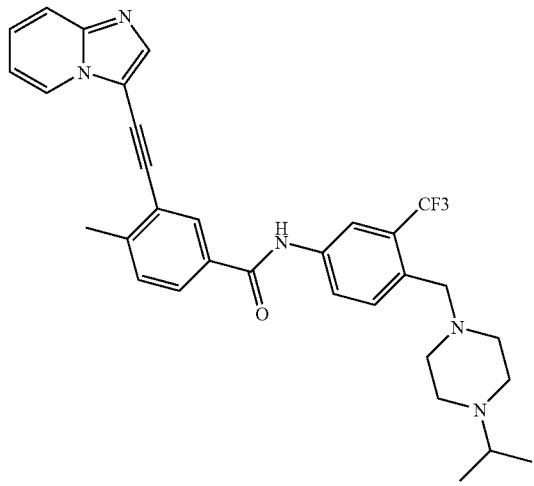 | <1000 |
| 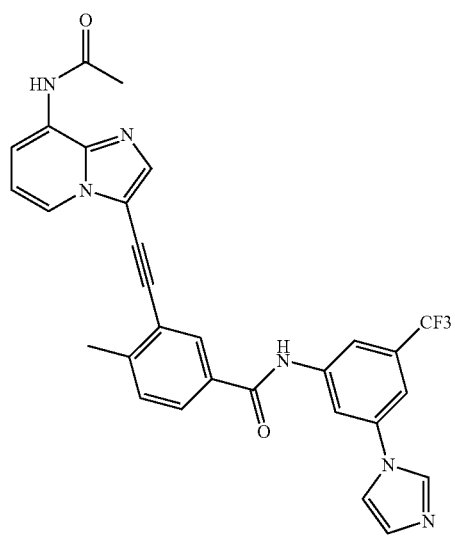 | <1000 |
| 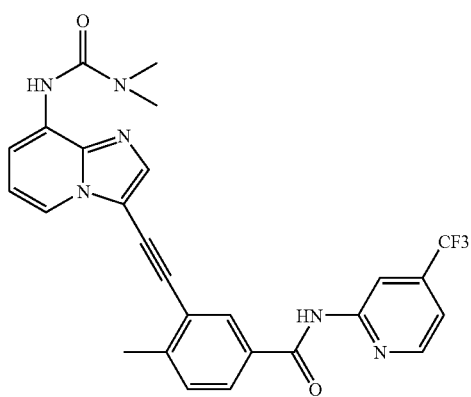 | <1000 |

-continued
| Compounds of the Invention | T315I cell proliferation (nM) |
|---|---|
| 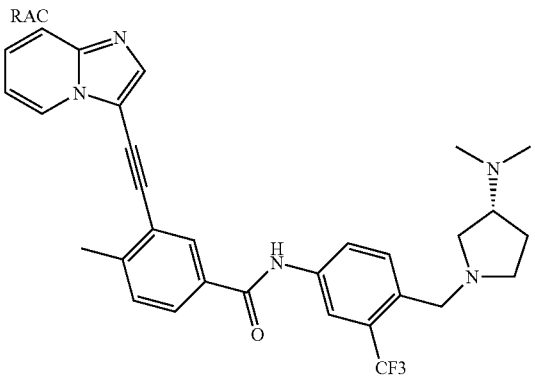 | <1000 |
| 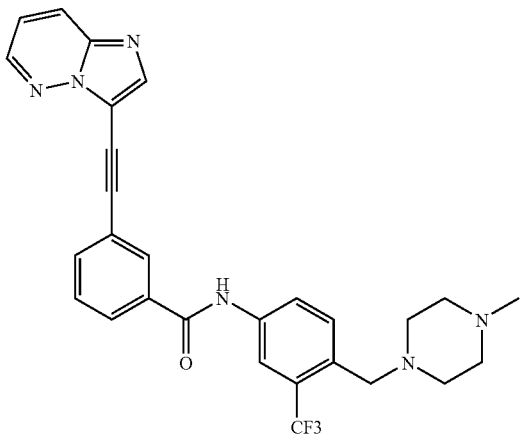 | <1000 |
| 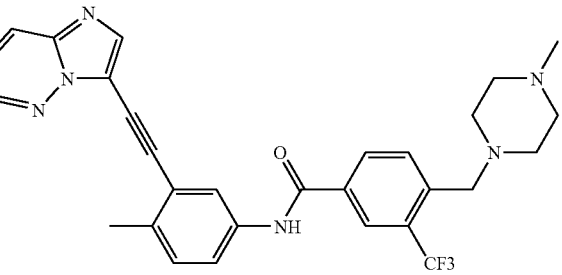 | <1000 |
| 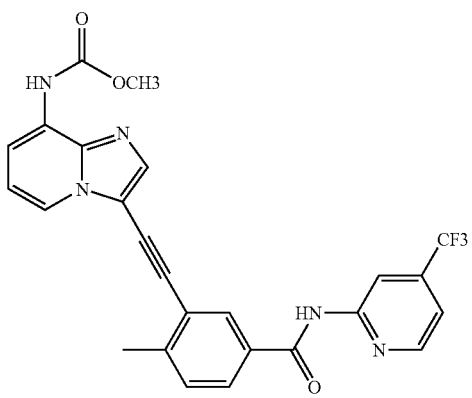 | <1000 |

-continued

| Compounds of the Invention | T315I cell proliferation (nM) |
|---|---|
| (structure) | <1000 |
| (structure) | <1000 |
| (structure) | <1000 |

-continued
| Compounds of the Invention | T315I cell proliferation (nM) |
|---|---|
| 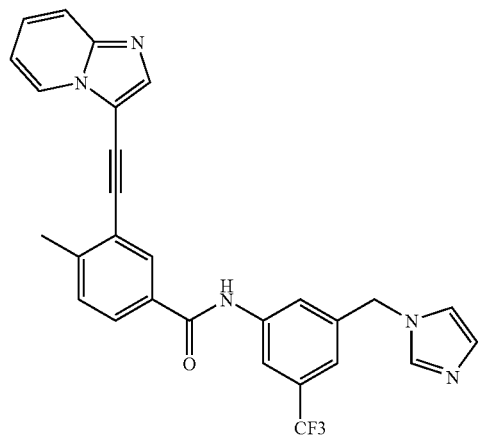 | <1000 |
| 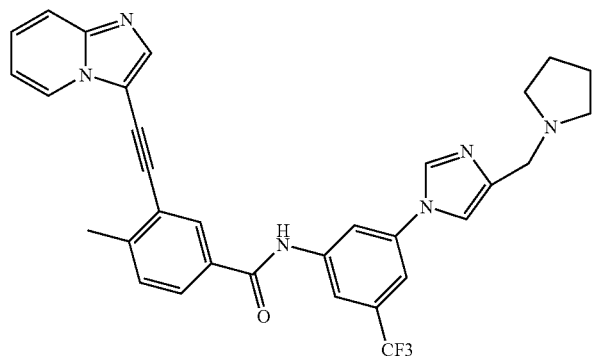 | <1000 |
| 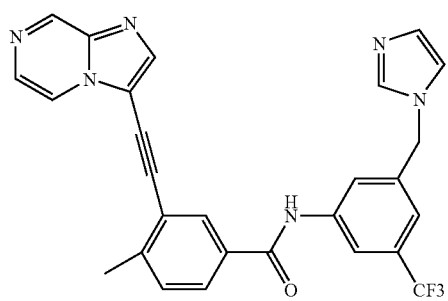 | <1000 |

-continued
| Compounds of the Invention | T315I cell proliferation (nM) |
|---|---|
| 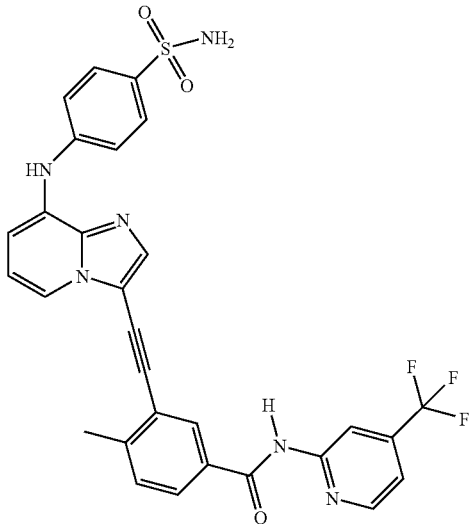 | <1000 |
| 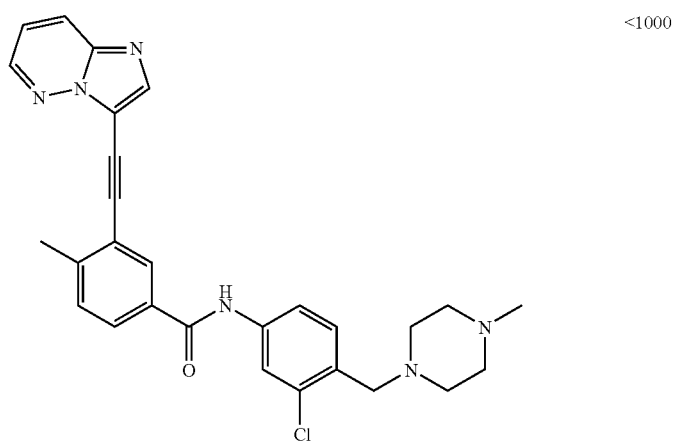 | <1000 |
| 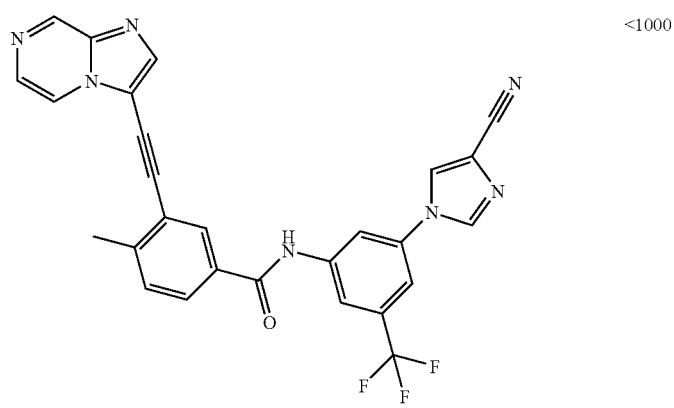 | <1000 |

| Compounds of the Invention | T315I cell proliferation (nM) |
|---|---|
| 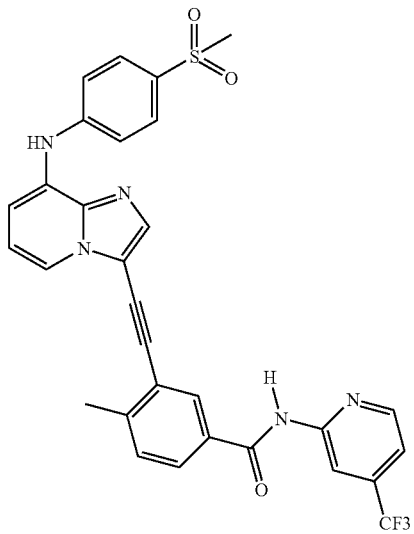 | <1000 |
| 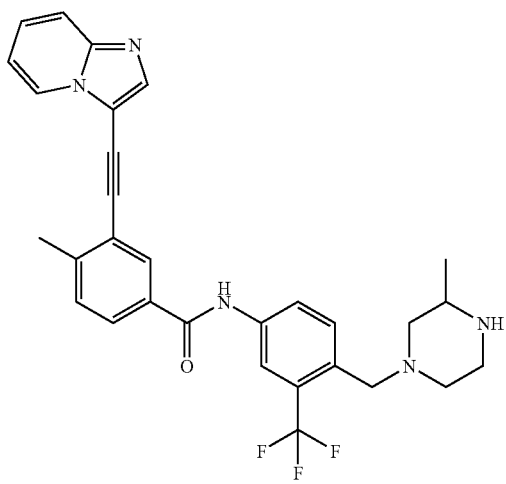 | <1000 |
| 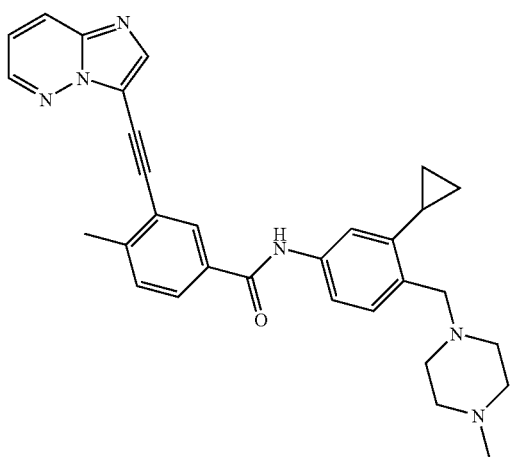 | <1000 |

-continued

| Compounds of the Invention | T315I cell proliferation (nM) |
|---|---|
| [structure: imidazo[1,2-a]pyrazine-ethynyl-pyridine-C(O)NH-phenyl(CF3)-CH2-N(piperazine)-isopropyl] | <1000 |
| [structure: imidazo[1,2-a]pyrazine-ethynyl-(methylphenyl)-C(O)NH-phenyl(CF3)-CH2-N(piperidine)-N(CH3)2] | <1000 |
| [structure: imidazo[1,2-a]pyridine-ethynyl-(methylphenyl)-C(O)NH-phenyl(CF3)-imidazole-CH2-N(CH3)2] | <1000 |

-continued

| Compounds of the Invention | T315I cell proliferation (nM) |
|---|---|
| (structure) | <1000 |
| (structure) | <1000 |
| (structure) | <1000 |

| Compounds of the Invention | T315I cell proliferation (nM) |
|---|---|
| (structure) | <1000 |
| (structure) | <1000 |
| (structure) | <1000 |

-continued

| Compounds of the Invention | T315I cell proliferation (nM) |
|---|---|
| [structure] | <1000 |
| [structure] | <1000 |
| [structure] | <1000 |

-continued
| Compounds of the Invention | T315I cell proliferation (nM) |
|---|---|
| 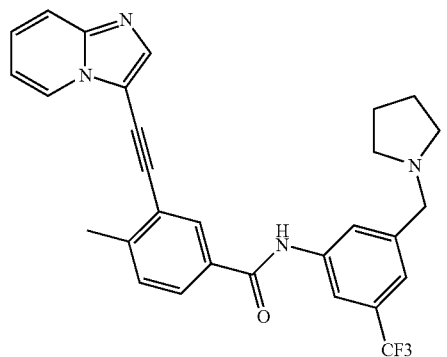 | <1000 |
| 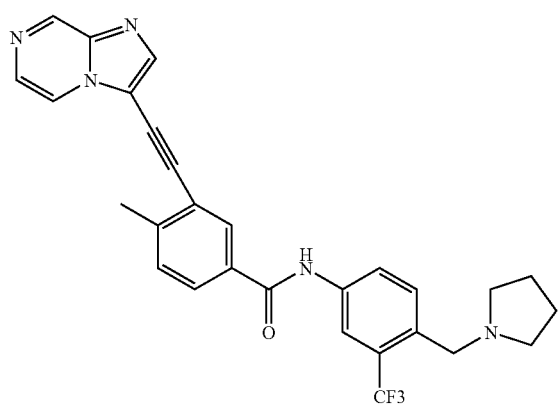 | <1000 |
| 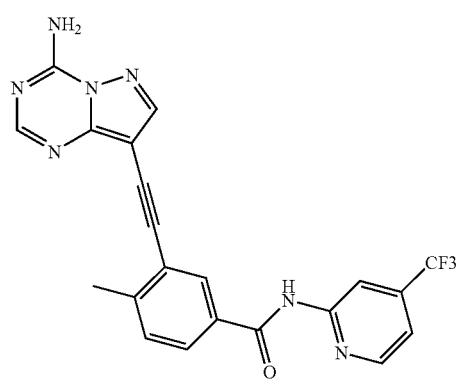 | <1000 |

-continued

| Compounds of the Invention | T315I cell proliferation (nM) |
|---|---|
| (imidazo[1,2-a]pyridin-3-yl-ethynyl attached to 4-methylbenzamide, N-linked to 3-CF3-4-(morpholinomethyl)phenyl) | <1000 |
| (8-acetamido-imidazo[1,2-a]pyridin-3-yl-ethynyl attached to 4-methylbenzamide, N-linked to 4-CF3-pyridin-2-yl) | <1000 |
| RAC (imidazo[1,2-a]pyridin-3-yl-ethynyl attached to 4-methylbenzamide, N-linked to 3-CF3-4-((3-hydroxypyrrolidin-1-yl)methyl)phenyl) | <1000 |

| Compounds of the Invention | T315I cell proliferation (nM) |
|---|---|
| 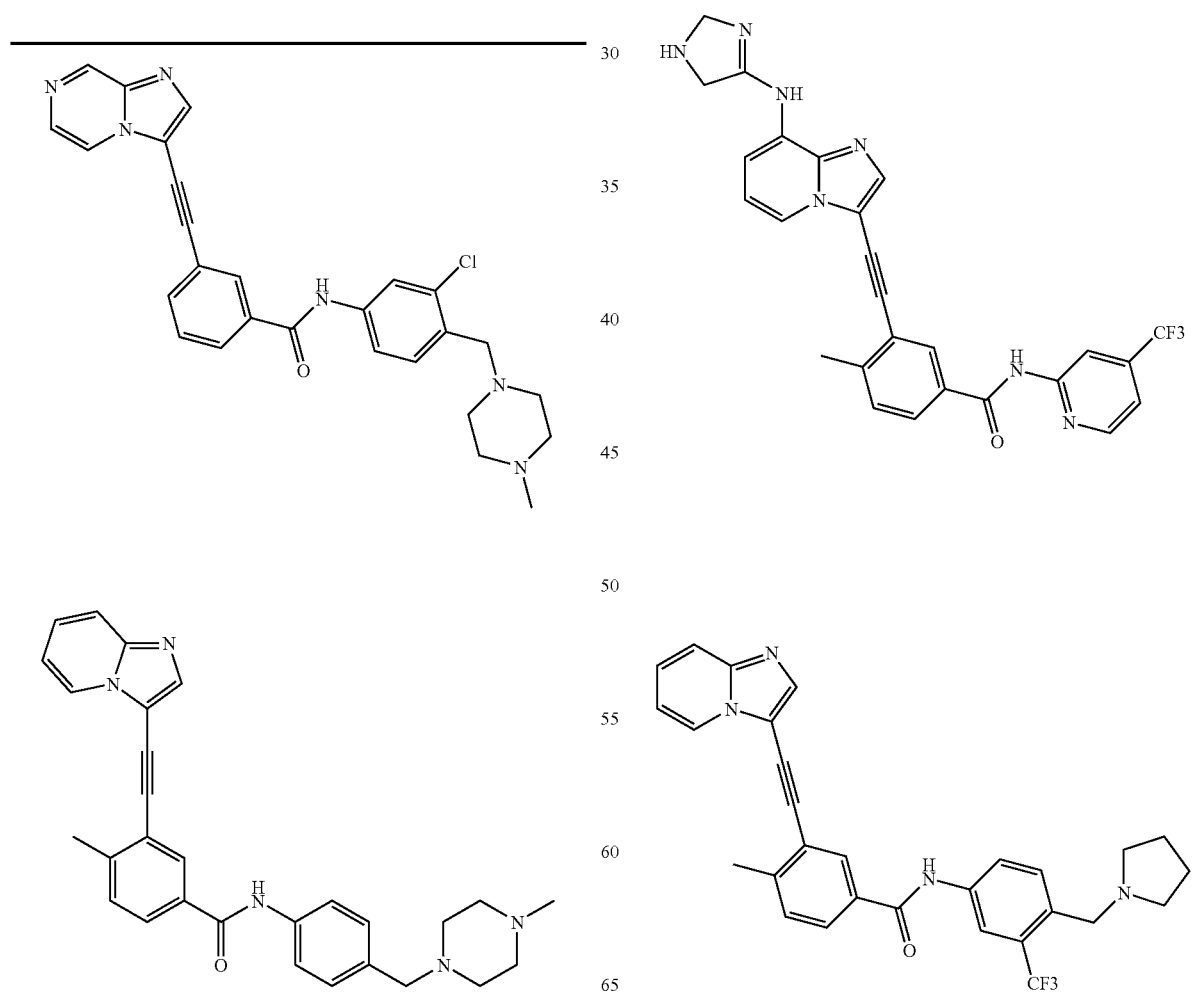 | <1000 |
The compounds listed in the table below also showed inhibitory activity against various protein kinase of interest.

| 137 -continued | 138 -continued |
|---|---|
| 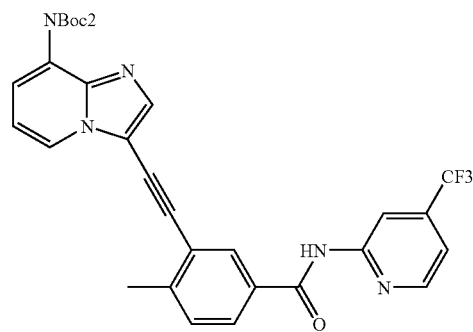 | 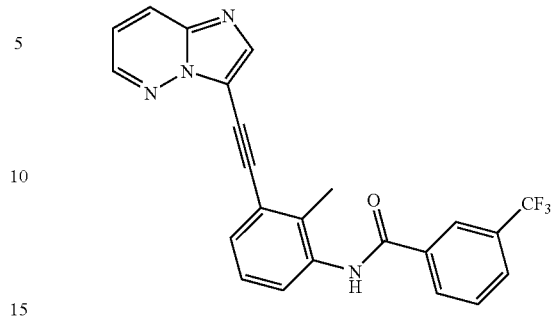 |
| 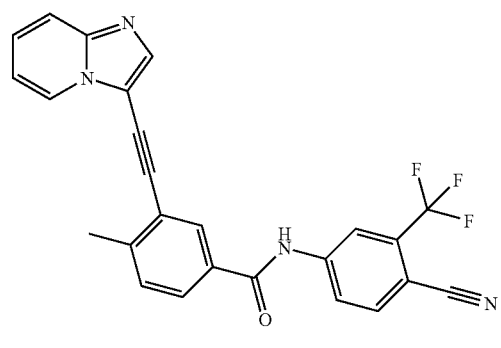 | 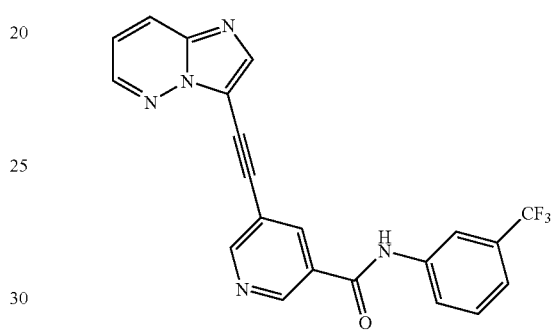 |
| 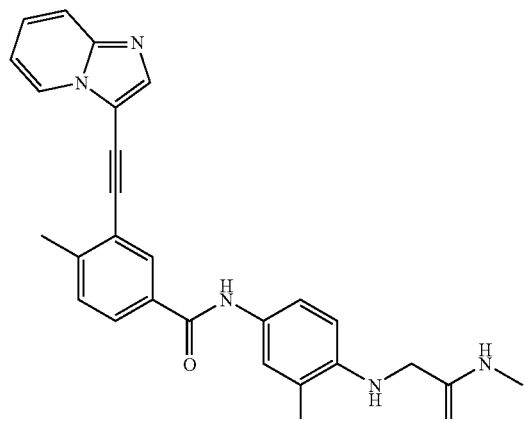 | 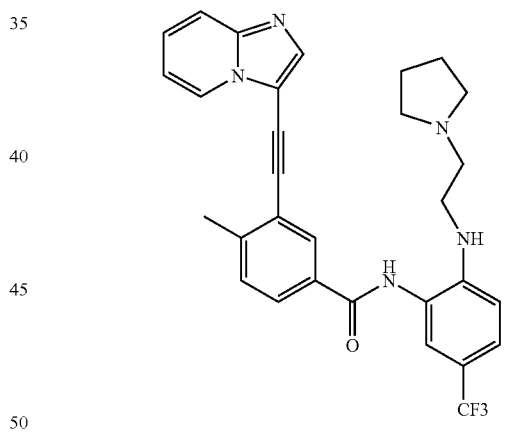 |
| 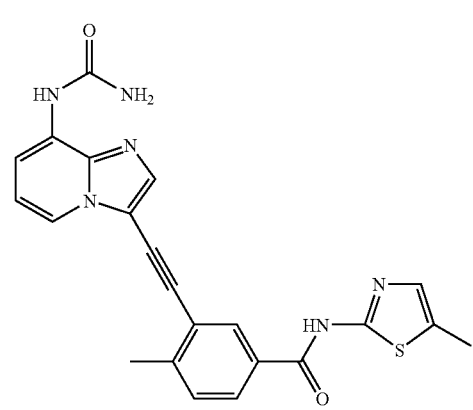 | 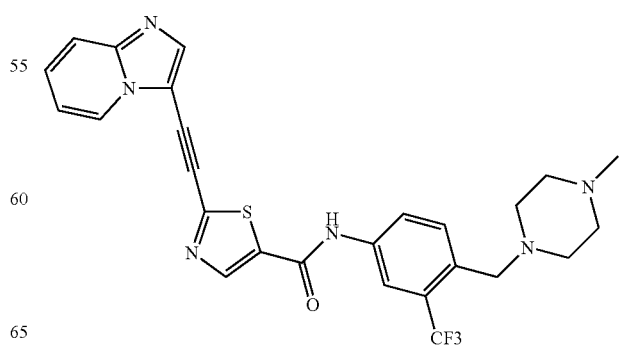 |

139
-continued

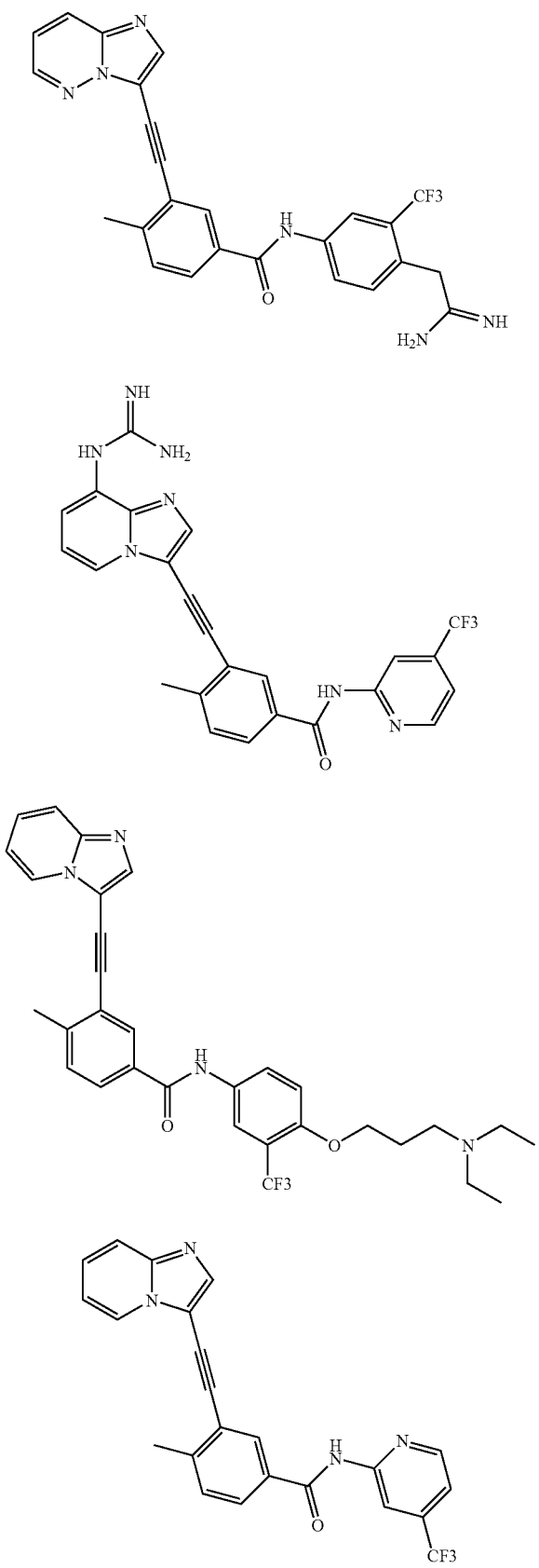

140
-continued

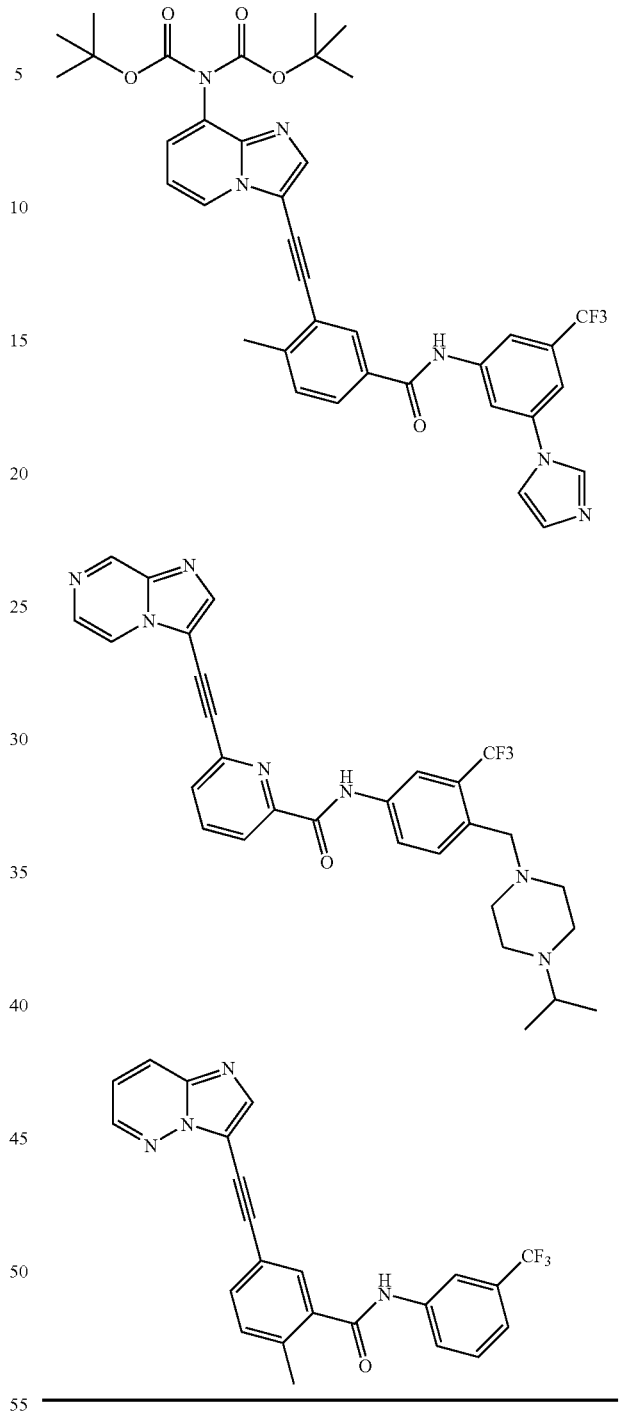

Kinase Inhibition

More specifically, the compounds described herein are screened for kinase inhibition activity as follows. Kinases suitable for use in the following protocol include, but are not limited to: ABl, Lck, Lyn, Src, Fyn, Syk, Zap-70, Itk, Tec, Btk, EGFR, ErbB2, Kdr, Flt1, Flt-3, Tek, c-Met, InsR, and AKT.

Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography as previously described (Lehr et al., 1996; Gish et al., 1995). In some instances, kinases are co-expressed or mixed with purified or partially purified regulatory polypeptides prior to measurement of activity.

Kinase activity and inhibition can be measured by established protocols (see e.g., Braunwalder et al., 1996). In such cases, the transfer of $^{33}PO_4$ from ATP to the synthetic substrates poly(Glu, Tyr) 4:1 or poly(Arg, Ser) 3:1 attached to the bioactive surface of microtiter plates is taken as a measure of enzyme activity. After an incubation period, the amount of phosphate transferred is measured by first washing the plate with 0.5% phosphoric acid, adding liquid scintillant, and then counting in a liquid scintillation detector. The IC50 is determined by the concentration of compound that causes a 50% reduction in the amount of $^{33}p$ incorporated onto the substrate bound to the plate.

In one method, the activated kinase is incubated with a biotinylated substrate peptide (containing tyr) with or without the presence of a compound of the invention. After the kinase assay incubation period, excess kinase inhibitor is added to kill the kinase reaction along with Europium-labeled anti-phosphotyrosine antibody (Eu-Ab) and Allophycocyanin-Streptavidin (SA-APC). The biotinylated substrate peptide (with or without phosphorylated Tyrosine) in solution binds to the SA-APC via Biotin-Avidin binding. The Eu-Ab binds only to substrate with phosphorylated tryrosine. When the solution is excited at 615 nm, there is an energy transfer from the Europium to the APC when they are in close proximity (i.e. attached to the same molecule of biotinylated and phosphorylated substrate peptide). The APC then fluoresces at a wavelength of 665 nm. Excitation and emission take place in a Wallac Victor$^2$ V plate reader where the plate is read fluorometrically and absorbances at 615 and 665 nm are recorded. These data are then processed by an Excel plate processor which calculates IC50s of test compounds by converting the fluorescence into amounts of phosphorylated substrate made and determining the concentration of test compound that would be required to inhibit the development of phosphorylated substrate by 50% (IC50).

Other methods relying upon the transfer of phosphate to peptide or polypeptide substrate containing tyrosine, serine, threonine or histidine, alone, in combination with each other, or in combination with other amino acids, in solution or immobilized (i.e., solid phase) are also useful.

For example, transfer of phosphate to a peptide or polypeptide can also be detected using scintillation proximity, Fluorescence Polarization or homogeneous time-resolved fluorescence. Alternatively, kinase activity can be measured using antibody-based methods in which an antibody or polypeptide is used as a reagent to detect phosphorylated target polypeptide.

For additional background information on such assay methodologies, see e.g., Braunwalder et al., 1996, Anal. Biochem. 234(I):23; Cleaveland et al., 1990, Anal Biochem. 190(2):249 Gish et al. (1995). Protein Eng. 8(6):609 Kolb et al. (1998). Drug Discov. Toda V. 3:333 Lehr et al. (1996). Gene 169(2):27527-87 Seethala et al. (1998). Anal Biochem. 255(2):257 Wu et al. (2000).

IC50 values in the low nanomolar range have been observed for compounds of this invention against various kinases, including Src, ABl and kdr.

Cell-based Assays

Certain compounds of this invention have also been demonstrated cytotoxic or growth inhibitory effects on tumor and other cancer cell lines and thus may be useful in the treatment of cancer and other cell proliferative diseases. Compounds are assayed for anti-tumor activity using in vivo and in vitro assays which are well known to those skilled in the art. Generally, initial screens of compounds to identify candidate anti-cancer drugs are performed in cellular assays. Compounds identified as having anti-proliferative activity in such cell-based assays can then be subsequently assayed in whole organisms for anti-tumor activity and toxicity. Generally speaking, cell-based screens can be performed more rapidly and cost-effectively relative to assays that use whole organisms. For purposes of this invention, the terms "anti-tumor" and "anti-cancer" activity are used interchangeably.

Cell-based methods for measuring antiproliferative activity are well known and can be used for comparative characterization of compounds of this invention. In general, cell proliferation and cell viability assays are designed to provide a detectable signal when cells are metabolically active. Compounds may be tested for antiproliferative activity by measuring any observed decrease in metabolic activity of the cells after exposure of the cells to compound. Commonly used methods include, for example, measurement of membrane integrity (as a measure of cell viability)(e.g. using trypan blue exclusion) or measurement of DNA synthesis (e.g. by measuring incorporation of BrdU or 3H-thymidine).

Some methods for assaying cell proliferation use a reagent that is converted into a detectable compound during cell proliferation. Particularly preferred compounds are tetrazolium salts and include without limitation MTT (3-(4, 5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bernas et al. Biochim Biophys Acta 1451(1):73-81, 1999). Preferred assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55-63, 1983).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

More specifically, the cell proliferation assay we currently perform is using CellTiter 96 AQueous One Solution Cell Proliferation assay kit (Promaga, Cat#G3581). This assay is a colorimetric method for determining the number of alive cells in proliferation or cytotoxicity assays. The assay utilizing terazolium salts detect cell proliferation by detecting the product of the enzymatic conversion of the tetrazolium salts into blue formazan derivatives, which can be measured by the absorbance at 490 nm in a plate reader, Wallac Victor$^2$V (PerkinElmer).

An example of cell-based assay is shown as below. The cell lines used in the assay are Ba/F3, a murine pro-B cell line, which have been stably transfected with full-length wild-type Bcr-Abl or Bcr-Abl with various kinase domain point mutations (including T351I, Y253F, E255K, H396P, M351T etc) constructs. Parental Ba/F3 cell line is used as control. These cell lines were obtained from Brian J. Druker (Howard Hughes Medical Institute, Oregon Health and Science University, Portland, Oreg. USA). Ba/F3 cell expressing Bcr-Abl or Bcr-Abl mutants were maintained in PRMI 1640 growth medium with 200 μM L-gultamine, 10% FCS, penicillin (200 U/ml), and streptomycin (200 μg/ml). Parental Ba/F3 cells were culture in the same medium supplemented with 10 ng/ml IL-3.

Parental Ba/F3 cells (supplemented with IL-3) or Ba/F3 cells expressing WT or mutant Bcr-Abl are plated in duplicate at $1 \times 10^4$ cells/well in 96-well plates with the compounds in different concentrations in the media. The compounds are first dissolved and diluted in DMSO by preparation of 4-fold dilution; next equal volumes of compounds with DMSO are transferred to medium and then transferred to cell plates. The final compound concentrations start from 10 μM to 6 nM. DMSO at same percentage is used as control. After compound was incubated with cells for 3 days, the numbers of active cells are measured using CellTiter 96 AQueous One Solution Cell Proliferation assay kit following the kit instruction. Basically, the tetrazolium salts are added to the incubated cultured cells to allow enzymatic conversion to the detectable product by active cells. Cells are processed, and the optical density of the cells is determined to measure the amount of formazan derivatives. Mean +/− SD are generated from duplicated wells and reported as the percentage absorbance of control. IC50s are calculated in best-fit curves using Micorsoft Excel-fit software.

In addition, a wide variety of cell types may be used to screen compounds for antiproliferative activity, including the following cell lines, among others: COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

While the cell line is preferably mammalian, lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, others may be used as well.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1/EBNA-1.

Other cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem Biol. 6:541-51; incorporated herein by reference) used HeLa cells containing an inducible variant of GFP to detect compounds that inhibited expression of the GFP, and thus inhibited cell proliferation.

Compounds identified by such cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. No. 4,736,866 and U.S. Pat. No. 5,175,383). For a review and discussion on the use of rodent models for antitumor drug testing see Kerbel (Cancer Metastasis Rev. 17:301-304, 1998-99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds see Corbett et al. (Invest New Drugs. 15:207-218, 1997; incorporated herein by reference).

Example 23

Pharmaceutical Compositions

Representative pharmaceutical dosage forms of the compounds of this invention (the active ingredient being referred to as "Compound"), are provided for therapeutic or prophylactic use in humans:

| (a) Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyffolidone (5% w/v paste) | 2.25 |
| Magnesium stearate | 3.0 |

| (c) Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0-76 |

| (d) Capsule | mg/capsule |
|---|---|
| Compound | 10 |
| Lactose Ph. Eur | 488.5 |
| Magnesium | 1.5 |

| (e) Injection I | (50 mg/ml) |
|---|---|
| Compound | 5.0% w/v |
| 1M Sodium hydroxide solution | 15.0% w/v |
| 0.1M Hydrochloric acid (to adjust pH to 7.6) | 4.5% w/v |
| Polyethylene glycol 400 | |
| Water for injection to 100% | |

| (f) Injection II | (10 mg/ml) |
|---|---|
| Compound | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol | 1 mg/ml |
|---|---|
| Compound | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound | 40 mg |
| Ethanol | 300 μl |
| Water | 300 μl |
| 1-Dodecylazacycloheptan one | 50 μl |
| Propylene glycol | to 1 ml |

Note: These formulations may be prepared using conventional procedures well known in the pharmaceutical art. The tablets (a)-(c) may be enteric coated by conventional means, if desired to provide a coating of cellulose acetate phthalate, for example. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

The invention claimed is:

1. A compound of formula:

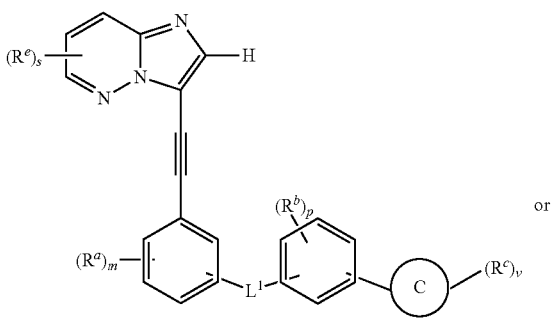

or

147

-continued

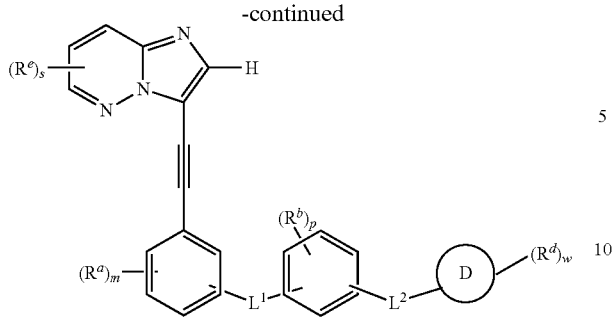

wherein:
L$^1$ is NR$^1$C(O) or C(O)NR$^1$;
Ring D represents a 5- or 6-membered heterocyclic or heteroaryl ring comprising carbon atoms and 1-3 heteroatoms independently selected from O, N and S(O)$_r$;
Ring C is a 5- or 6-membered heterocyclic or heteroaryl ring, comprising carbon atoms and 1-3 heteroatoms independently selected from O, N and S(O)$_r$;
L$^2$ is —(CH$_2$)$_z$—;
each occurrence of R$^a$ is independently selected from the group consisting of halo, alkyl and cycloalkyl;
each occurrence of R$^b$ is independently selected from the group consisting of halo, alkyl and cycloalkyl;
each occurrence of R$^c$ is independently selected from the group consisting of halo, alkyl and cycloalkyl;
each occurrence of R$^d$ is independently selected from the group consisting of halo, alkyl and cycloalkyl and —NR$^2$R$^3$;
each occurrence of R$^e$ is independently selected from the group consisting of halo, alkyl, cycloalkyl, —NR$^2$R$^3$, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocyclyl, —NH(CH$_2$)$_x$-aryl, and —(CH$_2$)$_x$C(O)NH$_2$, wherein x is 0, 1, 2 or 3;
each of R$^1$, R$^2$ and R$^3$ is independently selected from H, alkyl, alkenyl, alkynyl, cycloalkyl, cycloalkenyl, cycloalkynyl, aryl, heterocyclyl, and heteroaryl, or R$^2$ and R$^3$, taken together with the nitrogen atom to which at least one of R$^2$ and R$^3$ is attached, form a 5- or 6-membered heterocyclyl or heteroaryl ring;
each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$, and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;
m is 0, 1, 2, 3, or 4;
p is 0, 1, 2, 3, or 4;
r is 0, 1, or 2;

148 s is 0, 1, 2, or 3;
v is 0, 1, 2, 3, 4, or 5;
w is 0, 1, 2, 3, 4, or 5; and
z is 1, 2, 3 or 4;
or a pharmaceutically acceptable salt thereof.
2. The compound of claim 1 of the formula:

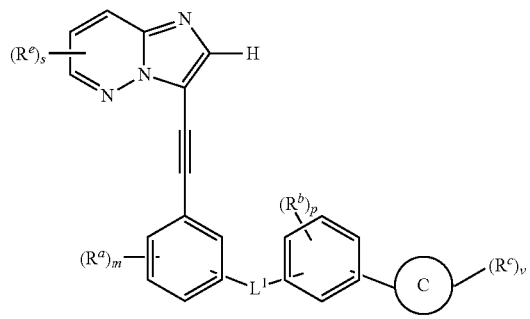

wherein:
L$^1$ is NR$^1$C(O) or C(O)NR$^1$;
Ring C is a 5-or 6-membered heterocyclyl or heteroaryl ring, comprising carbon atoms and 1-3 heteroatoms independently selected from O, N, and S(O)$_r$;
each occurrence of R$^a$ is independently selected from the group consisting of halo, alkyl, and cycloalkyl;
each occurrence of R$^b$ is independently selected from the group consisting of halo, alkyl, and cycloalkyl;
each occurrence of R$^c$ is independently selected from the group consisting of halo, alkyl, and cycloalkyl;
each occurrence of R$^e$ is independently selected from the group consisting of halo, alkyl, cycloalkyl, —NR$^2$R$^3$, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocyclyl, —NH(CH$_2$)$_x$-aryl, and —(CH$_2$)$_x$C(O)NH$_2$, wherein x is 0, 1, 2 or 3;
each of R$^1$, R$^2$ and R$^3$ is independently selected from H, alkyl, alkenyl, alkynyl, cycloalkyl, cycloalkenyl, cycloalkynyl, aryl, heterocyclyl, and heteroaryl, or R$^2$ and R$^3$, taken together with the nitrogen atom to which at least one of R$^2$ and R$^3$ is attached, form a 5- or 6-membered heterocyclyl or heteroaryl ring;
each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$, and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;
m is 0, 1, 2, 3, or 4;
p is 0, 1, 2, 3, or 4;

r is 0, 1, or 2;
s is 0, 1, 2, or 3; and
v is 0, 1, 2, 3, 4, or 5;
or a pharmaceutically acceptable salt thereof.

3. The compound of claim 2 in which Ring C is imidazolyl.

4. The compound of claim 2 of Formula IIc:

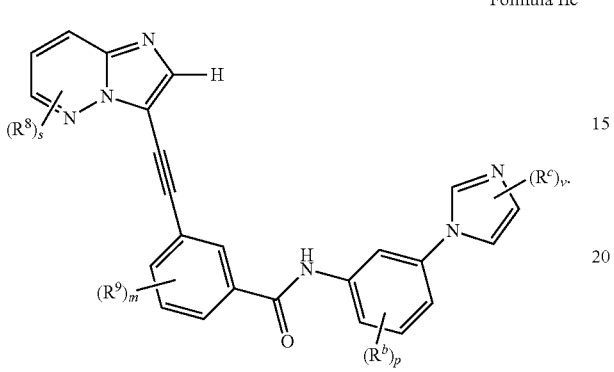

Formula IIc

5. The compound of claim 4 wherein s is 0; m, p and v are 1; $R^a$ and $R^c$ are methyl; and $R^b$ is $CF_3$.

6. The compound of claim 1 of the formula:

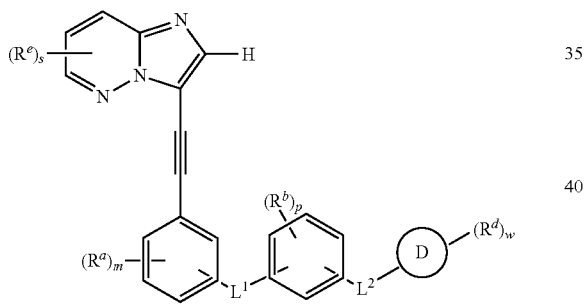

wherein:
L$^1$ is NR$^1$C(O) or C(O)NR$^1$;
Ring D is a 5- or 6-membered heterocyclyl or heteroaryl ring comprising carbon atoms and 1-3 heteroatoms independently selected from O, N, and S(O)$_r$;
L$^2$ is —(CH$_2$)z—;
each occurrence of R$^a$ is independently selected from the group consisting of halo, alkyl, and cycloalkyl;
each occurrence of R$^b$ is independently selected from the group consisting of halo, alkyl, and cycloalkyl;
each occurrence of R$^d$ is independently selected from the group consisting of halo, alkyl, cycloalkyl, and —NR$^2$R$^3$;
each occurrence of R$^e$ is independently selected from the group consisting of halo, alkyl, cycloalkyl, —NR$^2$R$^3$, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocyclyl, —NH(CH$_2$)$_x$-aryl, and —(CH$_2$)$_x$C(O)NH$_2$, wherein x is 0, 1, 2 or 3;

each of R$^1$, R$^2$ and R$^3$ is independently selected from H, alkyl, alkenyl, alkynyl, cycloalkyl, cycloalkenyl, cycloalkynyl, aryl, heterocyclyl, and heteroaryl, or R$^2$ and R$^3$, taken together with the nitrogen atom to which at least one of R$^2$ and R$^3$ is attached, form a 5- or 6-membered heterocyclyl or heteroaryl ring;

each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$, and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;

m is 0, 1, 2, 3, or 4;
p is 0, 1, 2, 3, or 4;
r is 0, 1, or 2;
s is 0, 1, 2, or 3;
w is 0, 1, 2, 3, 4, or 5; and
z is 1, 2, 3 or 4;
or a pharmaceutically acceptable salt thereof.

7. The compound of claim 6 wherein Ring D is piperazinyl.

8. The compound of claim 7 of Formula IIIc:

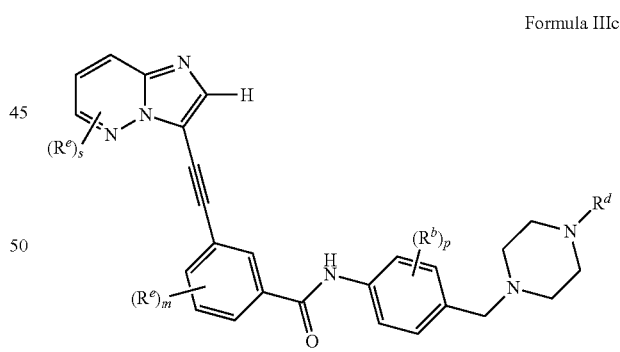

Formula IIIc wherein R$^d$ is a C1-C6 alkyl, unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$.

9. The compound of claim 8 wherein s is 0, m is 1, p is 1, R$^a$ is methyl, R$^b$ is CF$_3$, and R$^d$ is methyl or —CH$_2$CH$_2$OH.

10. A compound of formula:

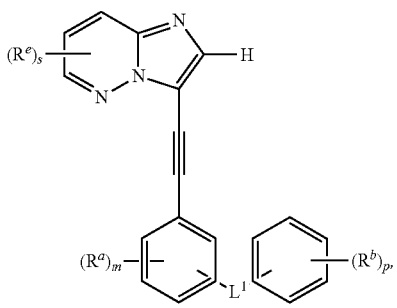

wherein:
L¹ is NR¹C(O) or C(O)NR¹;
each occurrence of R$^a$ is independently selected from the group consisting of halo, alkyl, and cycloalkyl;
each occurrence of R$^b$ is independently selected from the group consisting of halo, alkyl, and cycloalkyl;
each occurrence of R$^e$ is independently selected from the group consisting of halo, alkyl, cycloalkyl, —NR²R³, alkoxy, amino, —NH-alkyl, —C(O)NH-alkyl, —NHC(O)-alkyl, —NHC(O)NH-alkyl, —NHC(NH)-alkyl, —NHC(NH)NH₂, —NH(CH₂)$_x$-heteroaryl, —NH(CH₂)$_x$-heterocyclyl, —NH(CH₂)$_x$-aryl, and —(CH₂)$_x$C(O)NH₂, wherein x is 0, 1, 2 or 3;
each of R¹, R² and R³ is independently selected from H, alkyl, alkenyl, alkynyl, cycloalkyl, cycloalkenyl, cycloalkynyl, aryl, heterocyclyl, and heteroaryl, or R² and R³, taken together with the nitrogen atom to which at least one of R² and R³ is attached, form a 5- or 6-membered heterocyclyl or heteroaryl ring;
each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR²R³, =NNHC(O)R², =NNHCO₂R², and =NNHSO₂R², and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;
m is 0, 1, 2, 3, or 4;
p is 0, 1, 2, 3, 4, or 5; and
s is 0, 1, 2, or 3;
or a pharmaceutically acceptable salt thereof.

11. A composition comprising a compound of claim 10, or a pharmaceutically acceptable salt thereof, and a pharmaceutically acceptable vehicle.

12. The compound, (R)—N—(4((3-(Dimethylamino)pyrrolidin-1-yl)methyl)-3-(trifluoromethyl)phenyl)-3-(imidazo[1,2-b]pyridazin-3-ylethynyl)-4-methylbenzamide.

13. The compound, 3-(Imidazo[1,2-b]pyridazin-3-ylethynyl)-4-methyl-N-(4-((4-methylpiperazin-1-yl)methyl)-3-(trifluoromethyl)phenyl)benzamide.

14. The compound, N-(3-Chloro-4-((4-methylpiperazin-1-yl)methyl)phenyl)-3-(imidazo[1,2-b]pyridazin-3-ylethynyl)-4-methylbenzamide, or a pharmaceutically acceptable salt thereof.

15. The compound, N-(3-(Imidazo[1,2-b]pyridazin-3-ylethynyl)-4-methylphenyl)-4-((4-methylpiperazin-1-yl)methyl)-3-(trifluoromethyl)benzamide.

16. The compound, N-(3-Cyclopropyl-4-((4-methylpiperazin-1-yl)methyl)phenyl)-3-(imidazo[1,2-b]pyridazin-3-ylethynyl)-4-methylbenzamide.

17. The compound, 3-(Imidazo[1,2-b]pyridazin-3-ylethynyl)-N-(4-((4-methylpiperazin-1-yl)methyl)-3-(trifluoromethyl)phenyl)benzamide.

18. The compound, N-(4-((4-(2-Hydroxyethyl)piperazin-1-yl)methyl)-3-(trifluoromethyl)phenyl)-3-(imidazo[1,2-b]pyridazin-3-ylethynyl)-4-methylbenzamide.

19. The compound, 3-(Imidazo[1,2-b]pyridazin-3-ylethynyl)-4-methyl-N-(4-(piperazin-1-ylmethyl)-3-(trifluoromethyl)phenyl)benzamide.

20. The compound, (R)-N-(4-((3-(Dimethylamino)pyrrolidin-1-yl)methyl)-3 -(trifluoromethyl)phenyl)-3-(imidazo[1,2-b]pyridazin-3-ylethynyl)-4-methylbenzamide, or a pharmaceutically acceptable salt thereof.

21. The compound, N-(3-(Imidazo[1,2-b]pyridazin-3-ylethynyl)-4-methylphenyl)-4-((4-methylpiperazin-1-yl)methyl)-3-(trifluoromethyl)benzamide, or a pharmaceutically acceptable salt thereof 22. The compound, 3-(Imidazo[1,2-b]pyridazin-3-ylethynyl)-4-methyl-N-(4-((4-methylpiperazin-1-yl)methyl)-3-(trifluoromethyl)phenyl)benzamide, or a pharmaceutically acceptable salt thereof.

23. The compound, N-(3-Chloro-4-((4-methylpiperazin-1-yl)methyl)phenyl) -3-(imidazo[1,2-b]pyridazin-3-ylethynyl)-4-methylbenzamide.

24. The compound, N-(3-Cyclopropyl-4-((4-methylpiperazin-1-yl)methyl)phenyl)-3-(imidazo[1,2-b]pyridazin-3-ylethynyl)-4-methylbenzamide, or a pharmaceutically acceptable salt thereof.

25. The compound, 3-(Imidazo[1,2-b]pyridazin-3-ylethynyl)-N-(4-((4-methylpiperazin-1-yl)methyl)-3-(trifluoromethyl)phenyl)benzamide, or a pharmaceutically acceptable salt thereof.

26. The compound, N-(4-((4-(2-Hydroxyethyl)piperazin-1-yl)methyl)-3-(trifluoromethyl)phenyl)-3-(imidazo[1,2-b]pyridazin-3-ylethynyl)-4-methylbenzamide, or a pharmaceutically acceptable salt thereof.

27. The compound, 3-(Imidazo[1,2-b]pyridazin-3-ylethynyl)-4-methyl-N-(4-(piperazin-1-ylmethyl)-3-(trifluoromethyl)phenyl)benzamide, or a pharmaceutically acceptable salt thereof.

28. A hydrochloride salt of the compound, (R)-N-(4-((3-(Dimethylamino)pyrrolidin-1-yl)methyl)-3-(trifluoromethyl)phenyl)-3-(imidazo[1,2-b]pyridazin-3-ylethynyl)-4-methylbenzamide.

29. A hydrochloride salt of the compound, 3-(Imidazo[1,2-b]pyridazin-3-ylethynyl)-4-methyl-N-(4-((4-methylpiperazin-1-yl)methyl)-3-(trifluoromethyl)phenyl)benzamide.

30. A hydrochloride salt of the compound, N-(3-Chloro-4-((4-methylpiperazin-1-yl)methyl)phenyl)-3-(imidazo[1,2-b]pyridazin-3-ylethynyl)-4-methylbenzamide.

31. A composition comprising a compound of formula:

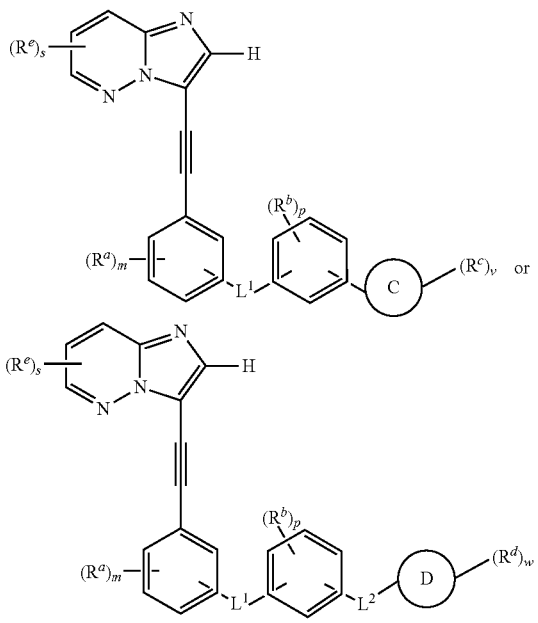

wherein L¹ is NR¹C(O) or C(O)NR¹;
Ring D is a 5- or 6-membered heterocyclyl or heteroaryl ring comprising carbon atoms and 1-3 heteroatoms independently selected from O, N, and S(O)$_r$;
Ring C is a 5-or 6-membered heterocyclyl or heteroaryl ring, comprising carbon atoms and 1-3 heteroatoms independently selected from O, N, and S(O)$_r$;
L² is —(CH$_2$)$_z$—;
each occurrence of R$^a$ is independently selected from the group consisting of halo, alkyl, and cycloalkyl;
each occurrence of R$^b$ is independently selected from the group consisting of halo, alkyl, and cycloalkyl;
each occurrence of R$^c$ is independently selected from the group consisting of halo, alkyl, and cycloalkyl;
each occurrence of R$^d$ is independently selected from the group consisting of halo, alkyl, cycloalkyl, and —NR²R³;
each occurrence of R$^e$ is independently selected from the group consisting of halo, alkyl, cycloalkyl, —NR²R³, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocyclyl, —NH(CH$_2$)$_x$-aryl, and —(CH$_2$)$_x$C(O)NH$_2$, wherein x is 0, 1, 2 or 3;
each of R¹, R² and R³ is independently selected from H, alkyl, alkenyl, alkynyl, cycloalkyl, cycloalkenyl, cycloalkynyl, aryl, heterocyclyl, and heteroaryl, or R² and R³, taken together with the nitrogen atom to which at least one of R² and R³ is attached, form a 5- or 6-membered heterocyclyl or heteroaryl ring;
each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR²R³, =NNHC(O)R², =NNHCO$_2$R², and =NNHSO$_2$R², and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;
m is 0, 1, 2, 3, or 4;
p is 0, 1, 2, 3, or 4;
r is 0, 1, or 2;
s is 0, 1, 2, or 3;
v is 0, 1, 2, 3, 4, or 5;
w is 0, 1, 2, 3, 4, or 5; and
z is 1, 2, 3 or 4;
or a pharmaceutically acceptable salt thereof, and a pharmaceutically acceptable vehicle.

32. The composition of claim 31, wherein said compound is of the formula:

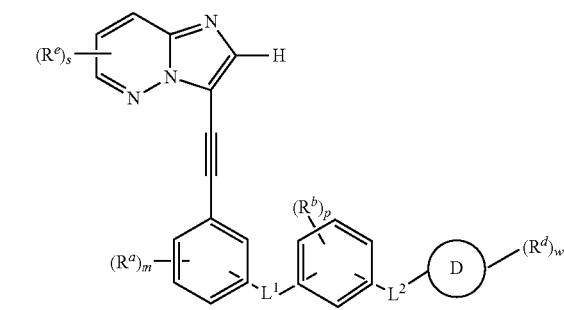

wherein:
Ring D is a 5- or 6-membered heterocyclyl or heteroaryl ring comprising carbon atoms and 1-3 heteroatoms independently selected from O, N, and S(O)$_r$;
L¹ is NR¹C(O) or C(O)NR¹;
L² is —(CH$_2$)$_z$—;
each occurrence of R$^a$ is independently selected from the group consisting of halo, alkyl, and cycloalkyl;
each occurrence of R$^b$ is independently selected from the group consisting of halo, alkyl, and cycloalkyl;
each occurrence of R$^d$ is independently selected from the group consisting of halo, alkyl, cycloalkyl, and —NR²R³;
each occurrence of R$^e$ is independently selected from the group consisting of halo, alkyl, cycloalkyl, —NR²R³, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocyclyl, —NH(CH$_2$)$_x$-aryl, and —(CH$_2$)$_x$C(O)NH$_2$, wherein x is 0, 1, 2 or 3;
each of R¹, R² and R³ is independently selected from H, alkyl, alkenyl, alkynyl, cycloalkyl, cycloalkenyl, cycloalkynyl, aryl, heterocyclyl, and heteroaryl, or R² and R³, taken together with the nitrogen atom to which at least one of R² and R³ is attached, form a 5- or 6-membered heterocyclyl or heteroaryl ring;
each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$, and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;

m is 0, 1, 2, 3, or 4;

p is 0, 1, 2, 3, or 4;

r is 0, 1, or 2;

s is 0, 1, 2, or 3;

w is 0, 1, 2, 3, 4, or 5; and z is 1, 2, 3 or 4;

or a pharmaceutically acceptable salt thereof, and a pharmaceutically acceptable vehicle.

33. The composition of claim 32, wherein said compound comprises a moiety:

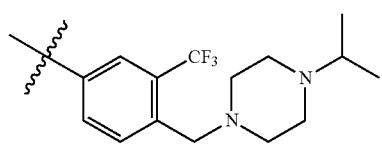

which is selected from the following:

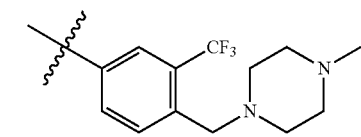

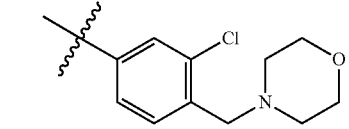

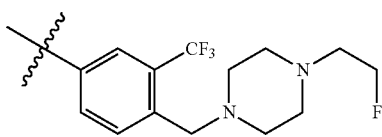

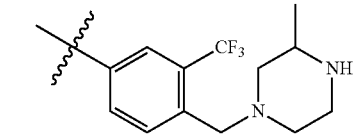

-continued

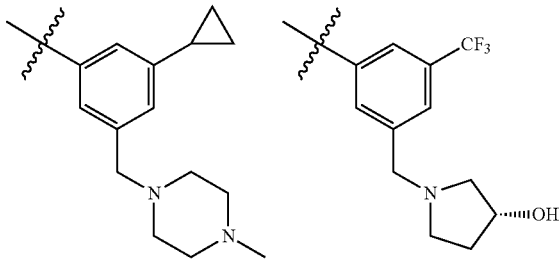

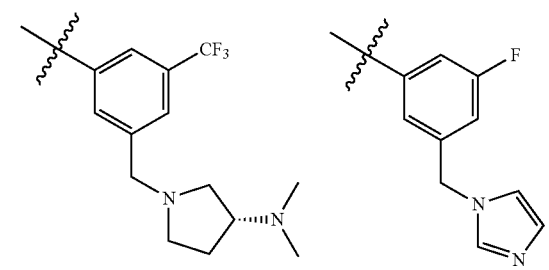

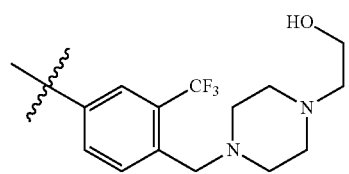

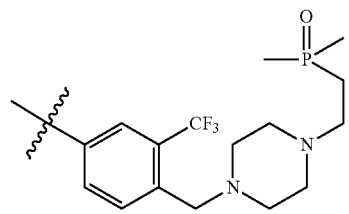

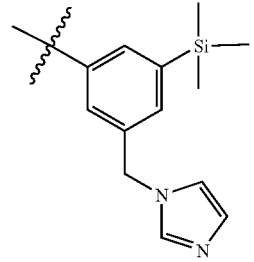

or a pharmaceutically acceptable salt thereof, and a pharmaceutically acceptable vehicle.

34. The composition of claim 32, wherein said compound comprises a moiety:

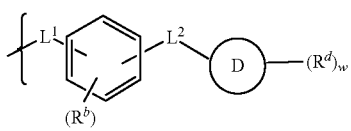

which is selected from the following:

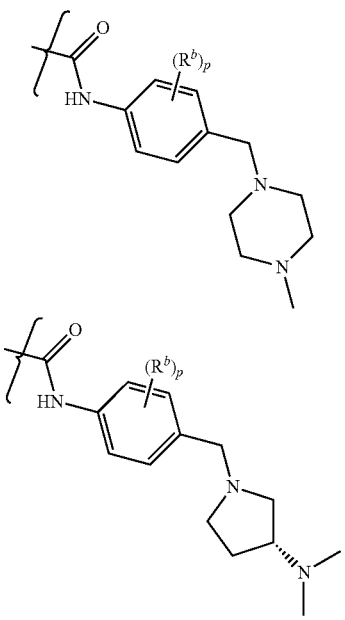

or a pharmaceutically acceptable salt thereof, and a pharmaceutically acceptable vehicle.

35. The composition of claim 32, in which Ring D is a piperazinyl; $R^d$ is C1-C6 alkyl; and w is 1.

36. The composition of claim 31, wherein said compound is of the formula:

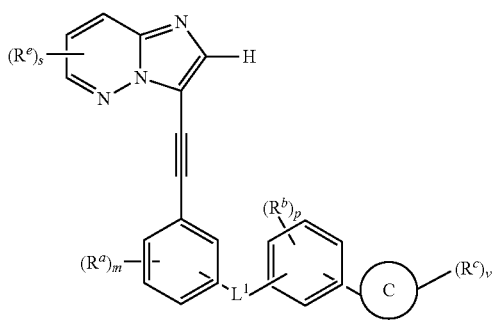

wherein:
L¹ is NR¹C(O) or C(O)NR¹;
Ring C is a 5-or 6-membered heterocyclyl or heteroaryl ring, comprising carbon atoms and 1-3 heteroatoms independently selected from O, N, and $S(O)_r$;
each occurrence of $R^a$ is independently selected from the group consisting of halo, alkyl, and cycloalkyl;
each occurrence of $R^b$ is independently selected from the group consisting of halo, alkyl, and cycloalkyl;
each occurrence of $R^c$ is independently selected from the group consisting of halo, alkyl, and cycloalkyl;
each occurrence of $R^e$ is independently selected from the group consisting of halo, alkyl, cycloalkyl, —NR²R³, alkoxy, amino, —NH-alkyl, —C(O)NH-alkyl, —NHC(O)-alkyl, —NHC(O)NH-alkyl, —NHC(NH)-alkyl, —NHC(NH)NH₂, —NH(CH₂)ₓ-heteroaryl, —NH(CH₂)ₓ-heterocyclyl, —NH(CH₂)ₓ-aryl, and —(CH₂)ₓC(O)NH₂, wherein x is 0, 1, 2 or 3;

each of R¹, R² and R³ is independently selected from H, alkyl, alkenyl, alkynyl, cycloalkyl, cycloalkenyl, cycloalkynyl, aryl, heterocyclyl, and heteroaryl, or R² and R³, taken together with the nitrogen atom to which at least one of R² and R³ is attached, form a 5- or 6-membered heterocyclyl or heteroaryl ring;

each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR²R³, =NNHC(O)R², =NNHCO₂R², and =NNHSO₂R², and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;

m is 0, 1, 2, 3, or 4;
p is 0, 1, 2, 3, or 4;
r is 0, 1, or 2;
s is 0, 1, 2, or 3; and
v is 0, 1, 2, 3, 4, or 5;

or a pharmaceutically acceptable salt thereof, and a pharmaceutically acceptable vehicle.

37. The composition of claim 31, wherein Ring C is imidazolyl.

38. The composition of claim 31, wherein said compound comprises a moiety:

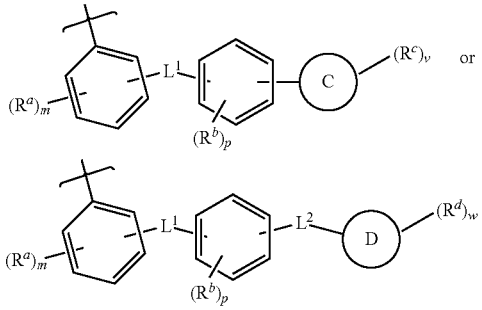

which has one of the following structures:

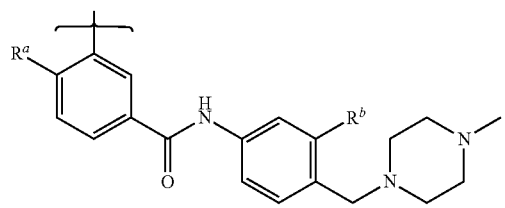

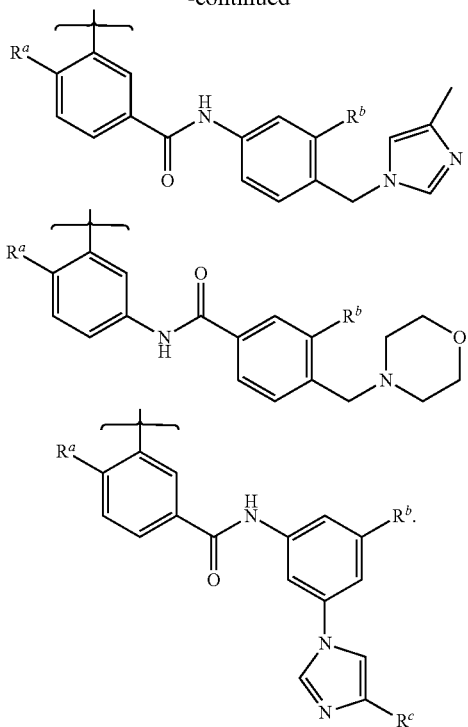

39. A composition comprising a compound of Formula IIc:

Formula IIc:

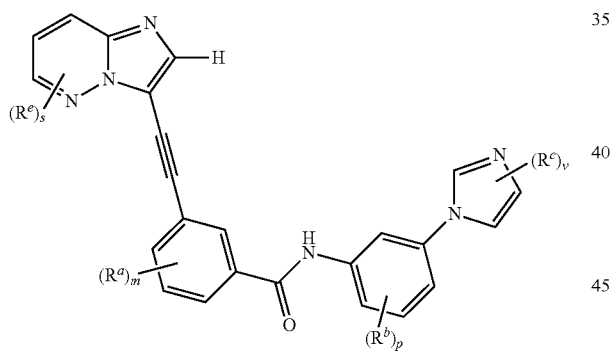

wherein:
  each occurrence of $R^a$ is independently selected from the group consisting of halo, alkyl, and cycloalkyl;
  each occurrence of $R^b$ is independently selected from the group consisting of halo, alkyl, and cycloalkyl;
  each occurrence of $R^c$ is independently selected from the group consisting of halo, alkyl, and cycloalkyl;
  each occurrence of $R^e$ is independently selected from the group consisting of halo, alkyl, cycloalkyl, —NR$^2$R$^3$, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocyclyl, —NH(CH$_2$)$_x$-aryl, and —(CH$_2$)$_x$C(O)NH$_2$, wherein x is 0, 1, 2 or 3;
  each of R$^2$ and R$^3$ is independently selected from H, alkyl, alkenyl, alkynyl, cycloalkyl, cycloalkenyl, cycloalkynyl, aryl, heterocyclyl, and heteroaryl, or R$^2$ and R$^3$, taken together with the nitrogen atom to which at least one of R$^2$ and R$^3$ is attached, form a 5- or 6-membered heterocyclyl or heteroaryl ring;
  each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$, and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;
  m is 0, 1, 2, 3, or 4;
  p is 0, 1, 2, 3, or 4;
  s is 0, 1, 2, or 3; and
  v is 0, 1, 2, 3, 4, or 5;
or a pharmaceutically acceptable salt thereof, and a pharmaceutically acceptable vehicle.

40. The composition of claim 39, wherein s is 0; m, p and v are 1; $R^a$ and $R^c$ are methyl; and $R^b$ is CF$_3$.

41. A composition comprising a compound of Formula IIIc:

Formula IIIc

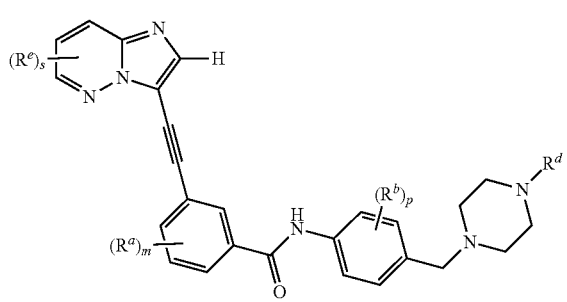

wherein:
  each occurrence of $R^a$ is independently selected from the group consisting of halo, alkyl, and cycloalkyl;
  each occurrence of $R^b$ is independently selected from the group consisting of halo, alkyl, and cycloalkyl;
  $R^d$ is a C1-C6 alkyl group, unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$;
  each occurrence of $R^e$ is independently selected from the group consisting of halo, alkyl, cycloalkyl, —NR$^2$R$^3$, alkoxy, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH (CH$_2$)$_x$-heterocyclyl, —NH(CH$_2$)$_x$-aryl, and —(CH$_2$)$_x$C(O)NH$_2$, wherein x is 0, 1, 2 or 3;

each of R$^2$ and R$^3$ is independently selected from H, alkyl, alkenyl, alkynyl, cycloalkyl, cycloalkenyl, cycloalkynyl, aryl, heterocyclyl, and heteroaryl, or R$^2$ and R$^3$, taken together with the nitrogen atom to which at least one of R$^2$ and R$^3$ is attached, form a 5- or 6-membered heterocyclyl or heteroaryl ring;

each of the alkyl, alkenyl, alkynyl, cycloalkyl, cycloalkenyl, cycloalkynyl, and heterocyclyl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, haloalkoxy, =O, =S, =NH, =NNR$^2$R$^3$, =NNHC(O)R$^2$, =NNHCO$_2$R$^2$, and =NNHSO$_2$R$^2$, and each of the aryl and heteroaryl moieties is unsubstituted or substituted with one or more groups selected from amino, alkylamino, dialkylamino, aminocarbonyl, halogen, alkyl, alkenyl, alkynyl, aryl, heteroaryl, carbocyclyl, heterocyclyl, alkylaminocarbonyl, dialkylaminocarbonyl, alkylaminocarbonyloxy, dialkylaminocarbonyloxy, nitro, cyano, carboxy, alkoxycarbonyl, alkylcarbonyl, hydroxy, alkoxy, acyloxy, and haloalkoxy;

m is 0, 1, 2, 3, or 4;

p is 0, 1, 2, 3, or 4; and s is 0, 1, 2, or 3;

or a pharmaceutically acceptable salt thereof, and a pharmaceutically acceptable vehicle.

42. The composition of claim 41 in which s is 0; m and p are 1; and R$^a$ is CH$_3$, R$^b$ is CF$_3$ and, R$^d$ is CH$_3$ or —CH$_2$CH$_2$OH.

43. The composition of either of claim 39 or 41 in which s is 0.

44. The composition of either of claim 39 or 41, in which s is 1, 2, or 3 and at least one R$^e$ is halo, C1-C6 alkyl, amino, —NH-alkyl, —C(O)NH-alkyl, —NHC(O)-alkyl, —NHC(O)NH-alkyl, —NHC(NH)-alkyl, —NHC(NH)NH$_2$, —NH(CH$_2$)$_x$-heteroaryl, —NH(CH$_2$)$_x$-heterocyclyl, —NH(CH$_2$)$_x$-aryl or —(CH$_2$)$_x$C(O)NH$_2$, in which x is 0, 1, 2 or 3.

45. A composition comprising a hydrochloride salt of the compound of claim 12, and a pharmaceutically acceptable carrier.

46. A composition comprising a hydrochloride salt of the compound of claim 13, and a pharmaceutically acceptable carrier.

47. A composition comprising a hydrochloride salt of the compound of claim 14, and a pharmaceutically acceptable carrier.

48. A composition comprising the compound, (R)-N-(4-((3-(Dimethylamino)pyrrolidin-1-yl)methyl)-3-(trifluoromethyl)phenyl)-3-(imidazo[1,2-b]pyridazin-3-ylethynyl)-4-methylbenzamide, or a pharmaceutically acceptable salt thereof, and a pharmaceutically acceptable carrier.

49. A composition comprising the compound, N-(3-(Imidazo[1,2-b]pyridazin -3-ylethynyl)-4-methylphenyl)-4-((4-methylpiperazin-1-yl)methyl)-3-(trifluoromethyl)benzamide, or a pharmaceutically acceptable salt thereof, and a pharmaceutically acceptable carrier.

50. A composition comprising the compound, 3-(Imidazo[1,2-b]pyridazin-3-ylethynyl)-4-methyl-N-(4-((4-methylpiperazin-1-yl)methyl)-3-(trifluoromethyl)phenyl)benzamide, or a pharmaceutically acceptable salt thereof, and a pharmaceutically acceptable carrier.

51. A composition comprising the compound, N-(3-Chloro-4-((4-methylpiperazin-1-yl)methyl)phenyl)-3-(imidazo[1,2-b]pyridazin-3-ylethynyl)-4-methylbenzamide, or a pharmaceutically acceptable salt thereof, and a pharmaceutically acceptable carrier.

52. A composition comprising the compound, N-(3-Cyclopropyl-4-((4-methylpiperazin-1-yl)methyl)phenyl)-3-(imidazo[1,2-b]pyridazin-3-ylethynyl)-4-methylbenzamide, or a pharmaceutically acceptable salt thereof, and a pharmaceutically acceptable carrier.

53. A composition comprising the compound, 3-(Imidazo[1,2-b]pyridazin-3-ylethynyl)-N-(4-((4-methylpiperazin-1-yl)methyl)-3-(trifluoromethyl)phenyl)benzamide, or a pharmaceutically acceptable salt thereof, and a pharmaceutically acceptable carrier.

54. A composition comprising the compound, N-(4-((4-(2-Hydroxyethyl)piperazin-1-yl)methyl)-3-(trifluoromethyl)phenyl)-3-(imidazo[1,2-b]pyridazin-3-ylethynyl)-4-methylbenzamide, or a pharmaceutically acceptable salt thereof, and a pharmaceutically acceptable carrier.

55. A composition comprising the compound, 3-(Imidazo[1,2-b]pyridazin-3-ylethynyl)-4-methyl-N-(4-(piperazin-1-ylmethyl)-3-(trifluoromethyl)phenyl)benzamide, or a pharmaceutically acceptable salt thereof, and a pharmaceutically acceptable carrier.

* * * * *

UNITED STATES PATENT AND TRADEMARK OFFICE
CERTIFICATE OF CORRECTION

Page 1 of 2

PATENT NO. : 8,114,874 B2
APPLICATION NO. : 11/644849
DATED : February 14, 2012
INVENTOR(S) : Dong Zou et al.

It is certified that error appears in the above-identified patent and that said Letters Patent is hereby corrected as shown below:

On the Title Page,

"(65)        Prior Publication Data

US 2007/0191376 A1        Aug. 16, 2007

(51)    Int. Cl.
        *A61K 31/495*        (2006.01)"

should read

--(65)        Prior Publication Data

US 2007/0191376 A1    Aug. 16, 2007

Related U.S. Application Data

(60)    Provisional application No. 60/754,000, filed on Dec. 23, 2005, provisional application No. 60/753,962, filed on Dec. 23, 2005, provisional application No. 60/756,089, filed on Jan. 3, 2006, provisional application No. 60/798,472, filed on May 8, 2006, provisional application No. 60/833,191, filed on Jul. 25, 2006.

(51)    Int. Cl.
        *A61K 31/495*        (2006.01)--.

Signed and Sealed this
Nineteenth Day of April, 2016

Michelle K. Lee
*Director of the United States Patent and Trademark Office*

CERTIFICATE OF CORRECTION (continued)
U.S. Pat. No. 8,114,874 B2

Specification

Column 1, line 4, insert the following:
--RELATED APPLICATIONS

The present application claims priority under 35 U.S.C. §119(e) to U.S. Provisional Patent Application No. 60/754,000, filed December 23, 2005, U.S. Provisional Patent Application No. 60/753,962 filed December 23, 2005, U.S. Provisional Patent Application No. 60/756,089 filed January 3, 2006, U.S. Provisional Patent Application No. 60/798,472 filed May 8, 2006, and U.S. Provisional Patent Application No. 60/833,191 filed July 25, 2006, the entire contents of each of these applications are hereby incorporated by reference.--.